United States Patent
Landegren et al.

(10) Patent No.: US 11,649,486 B2
(45) Date of Patent: May 16, 2023

(54) DOUBLE-STRANDED CIRCLE PROBES

(71) Applicant: Olink Bioscience AB, Uppsala (SE)

(72) Inventors: Ulf Landegren, Uppsala (SE); Johan Björkesten, Storvreta (SE)

(73) Assignee: NAVINCI DIAGNOSTICS AB, Uppsala (SE)

( * ) Notice: Subject to any disclaimer, the term of this patent is extended or adjusted under 35 U.S.C. 154(b) by 760 days.

(21) Appl. No.: 16/325,247

(22) PCT Filed: Aug. 15, 2017

(86) PCT No.: PCT/EP2017/070654
§ 371 (c)(1),
(2) Date: Feb. 13, 2019

(87) PCT Pub. No.: WO2018/033528
PCT Pub. Date: Feb. 22, 2018

(65) Prior Publication Data
US 2019/0203279 A1 Jul. 4, 2019

(30) Foreign Application Priority Data

Aug. 16, 2016 (GB) .................................... 1614023

(51) Int. Cl.
| | |
|---|---|
| *C12Q 1/6844* | (2018.01) |
| *C12Q 1/6832* | (2018.01) |
| *C12Q 1/6853* | (2018.01) |
| *C12Q 1/6848* | (2018.01) |
| *C12Q 1/6876* | (2018.01) |
| *C12Q 1/6816* | (2018.01) |
| *C12Q 1/6827* | (2018.01) |

(52) U.S. Cl.
CPC ......... *C12Q 1/6844* (2013.01); *C12Q 1/6816* (2013.01); *C12Q 1/6827* (2013.01); *C12Q 1/6832* (2013.01); *C12Q 1/6848* (2013.01); *C12Q 1/6853* (2013.01); *C12Q 1/6876* (2013.01); *C12Q 2525/131* (2013.01); *C12Q 2525/161* (2013.01); *C12Q 2525/301* (2013.01); *C12Q 2525/307* (2013.01); *C12Q 2531/125* (2013.01); *C12Q 2537/163* (2013.01)

(58) Field of Classification Search
CPC .. C12Q 1/6844; C12Q 1/6816; C12Q 1/6832; C12Q 1/6848; C12Q 1/6853; C12Q 1/6876; C12Q 2525/131; C12Q 2525/161; C12Q 2525/301; C12Q 2525/307; C12Q 2531/125; C12Q 2537/163
See application file for complete search history.

(56) References Cited

U.S. PATENT DOCUMENTS

| | | | |
|---|---|---|---|
| 5,854,033 A | 12/1998 | Lizardi | |
| 6,291,187 B1 | 9/2001 | Kingsmore et al. | |
| 6,511,809 B2 | 1/2003 | Baez et al. | |
| 6,558,928 B1 | 5/2003 | Landegren | |
| 6,596,486 B2 | 7/2003 | Frank-Kamenetskii et al. | |
| 6,610,481 B2 | 8/2003 | Koch | |
| 6,686,157 B2 | 2/2004 | Ward et al. | |
| 6,867,028 B2 | 3/2005 | Janulaitis et al. | |
| 7,320,860 B2 | 1/2008 | Landegren et al. | |
| 2001/0041340 A1 | 11/2001 | Kingsmore et al. | |
| 2002/0192649 A1 | 12/2002 | Lizardi | |
| 2003/0059786 A1 | 3/2003 | Ward et al. | |
| 2004/0248103 A1 | 12/2004 | Feaver et al. | |
| 2005/0069939 A1 | 3/2005 | Wang et al. | |
| 2005/0118616 A1 | 6/2005 | Kawashima et al. | |
| 2005/0147973 A1 | 7/2005 | Knott | |
| 2009/0233277 A1 | 9/2009 | Murakami | |

FOREIGN PATENT DOCUMENTS

| | | |
|---|---|---|
| EP | 2369015 A1 | 9/2011 |
| GB | 2382137 A | 5/2003 |
| WO | 92/01813 A1 | 2/1992 |
| WO | 97/00446 A1 | 1/1997 |
| WO | 97/19193 A2 | 5/1997 |
| WO | 97/20948 A1 | 6/1997 |
| WO | 98/38300 A1 | 9/1998 |
| WO | 99/49079 A1 | 9/1999 |

(Continued)

OTHER PUBLICATIONS

Official Action dated May 7, 2020 from corresponding European Application No. 17754692.6.

Dahl, Fredrik et al., Circle-to-circle amplification for precise and sensitive DNA analysis, PNAS, vol. 101, No. 13, pp. 4548-4553 (Mar. 30, 2004).

Dean, Frank B. et al., Rapid Amplification of Plasmid and Phage DNA Using Phi29 DNA Polymerase and Multiply-Primed Rolling Circle Amplification, Genome Research, vol. 11, pp. 1095-1099 (2001).

(Continued)

*Primary Examiner* — Angela M. Bertagna
(74) *Attorney, Agent, or Firm* — Porter Wright Morris & Arthur LLP

(57) ABSTRACT

Nucleic acid probes for detection of a target nucleic acid molecule by an RCA reaction in the presence of the target nucleic acid molecule, comprise a first circular template strand which is capable of acting as a template for RCA, and is protected from RCA in the absence of the target nucleic acid molecule by at least a second protector strand which comprises a region of complementarity to the first template strand and is hybridised thereto to form a double-stranded circular structure containing the first template strand inside the protector strand(s). At least one of the second and/or any further protector strands comprises a target binding site, such that upon binding of the probe to the target nucleic acid molecule the probe is able to undergo a strand displacement reaction which allows RCA of the first template strand. Methods of detecting target analytes use such probes.

26 Claims, 29 Drawing Sheets

Specification includes a Sequence Listing.

(56) References Cited

FOREIGN PATENT DOCUMENTS

| WO | 00/23619 | A1 | 4/2000 | | |
|---|---|---|---|---|---|
| WO | 01/61037 | A1 | 8/2001 | | |
| WO | 01/88190 | A2 | 11/2001 | | |
| WO | 02/057487 | A2 | 7/2002 | | |
| WO | 03/012119 | A2 | 2/2003 | | |
| WO | 03/044229 | A1 | 5/2003 | | |
| WO | 03/044231 | A1 | 5/2003 | | |
| WO | 2004/094456 | A2 | 11/2004 | | |
| WO | 2005/047474 | A2 | 5/2005 | | |
| WO | 2005/070630 | A1 | 8/2005 | | |
| WO | 2005/123963 | A2 | 12/2005 | | |
| WO | 2006/020515 | A1 | 2/2006 | | |
| WO | 2006/076650 | A2 | 7/2006 | | |
| WO | 2006/108422 | A2 | 10/2006 | | |
| WO | 2007/005649 | A2 | 1/2007 | | |
| WO | 2007/044903 | A2 | 4/2007 | | |
| WO | 2009/012220 | A2 | 1/2009 | | |
| WO | 2009/017861 | A2 | 2/2009 | | |
| WO | 2009/037659 | A2 | 3/2009 | | |
| WO | 2010/069064 | A1 | 6/2010 | | |
| WO | 2012/049316 | A1 | 4/2012 | | |
| WO | 2012/104261 | A1 | 8/2012 | | |
| WO | 2012/152942 | A1 | 11/2012 | | |
| WO | WO-2012152942 | A1 * | 11/2012 | ........... | C12Q 1/6841 |
| WO | 2014/076209 | A1 | 5/2014 | | |
| WO | 2014/076214 | A1 | 5/2014 | | |
| WO | WO-2014076214 | A1 * | 5/2014 | ........... | C12Q 1/6853 |
| WO | 2015/071445 | A1 | 5/2015 | | |
| WO | 2016/016450 | A1 | 2/2016 | | |
| WO | 2016/016452 | A1 | 2/2016 | | |

OTHER PUBLICATIONS

Fredriksson, Simon et al., Protein detection using proximity-dependent DNA ligation assays, Nature Biotechnology, vol. 20, pp. 473-477 (May 2002).

Göransson, Jenny et al., A single molecule array for digital targeted molecular analyses, Nucleic Acids Research, vol. 37, No. 1, e7, pp. 1-9 (published online Nov. 25, 2008).

Gullberg, Mats et al., Cytokine detection by antibody-based proximity ligation, PNAS, vol. 101, No. 22, pp. 8420-8424 (Jun. 1, 2004).

Howell, W. Mathias et al., Glycosylases and AP-cleaving enzymes as a general tool for probe-directed cleavage of ssDNA targets, Nucleic Acids Research, vol. 38, No. 7, e99, pp. 1-10 (published online Jan. 15, 2010).

International Search Report from priority application GB 1614023.8 dated May 16, 2017.

Kuhn, Heiko et al., Rolling-circle amplification under topological constraints, Nucleic Acids Research, vol. 30, No. 2, pp. 574-580 (2002).

Lizardi, Paul M. et al., Mutation detection and single-molecule counting using isothermal rolling-circle amplification, Nature Genetics (Nature America Inc.), vol. 19, pp. 225-232 (Jul. 1998).

Nong, Rachel Yuan et al., Unfolding proximity ligation probes for measuring and imaging individual nucleic acid and protein molecules, Acta Universitatis Upsaliensis, pp. 1-15 (Oct. 7, 2011).

Wu, Lucia R. et al., Continuously tunable nucleic acid hybridization probes, Nature Methods, vol. 12, No. 12, pp. 1191-1198 (Dec. 2015).

Olasagasti, Felix et al., Replication of individual DNA molecules under electronic control using a protein nanopore, Nature Nanotechnology, vol. 5, pp. 798-806 (Nov. 2010).

Rashid, Hytham Rashad, Blocking Oligomer Design Update (3/10-3/11) Modifications for the Inhibition of Φ29 (exo +) DNA Polymerase, Department of Biomolecular Engineering, Nanopore Lab, University of California, Santa Cruz, Senior Thesis, pp. 1-20 (2011).

Söderberg, Ola et al., Direct observation of individual endogenous protein complexes in situ by proximity ligation, Nature Methods, vol. 3, No. 12, pp. 995-1000 (Dec. 2006).

Thomas, PhD, David C. et al., Amplification of Padlock Probes for DNA Diagnostics by Cascade Rolling Circle Amplification or the Polymerase Chain Reaction, Arch Pathol Lab Med, vol. 123, pp. 1170-1176 (Dec. 1999).

Wählby, Carolina et al., Sequential Immunofluorescence Staining and Image Analysis for Detection of Large Numbers of Antigens in Individual Cell Nuclei, Cytometry, vol. 47, pp. 32-41 (2002).

Weibrecht, Irene et al., Proximity ligations assays: a recent addition to the proteomics toolbox, Expert Rev. Proteomics, vol. 7, No. 3, pp. 401-409 (2010).

Weibrecht, Irene et al., Visualising individual sequence-specific protein-DNA interactions in situ, New Biotechnology, vol. 29, No. 5, pp. 589-598 (Jun. 2012).

Wu, Zai-Sheng et al., Universal Aptameric System for Highly Sensitive Detection of Protein Based on Structure-Switching-Triggered Rolling Circle Amplification, Anal. Chem., vol. 82, pp. 2221-2227 (2010).

Jarvius, Malin et al., In Situ Detection of Phosphorylated Plateletderived Growth Factor Receptor β Using a Generalized Proximity Ligation Method, Molecular & Cellular Proteomics, vol. 6, pp. 1500-1509 (2007).

Office Action and Search Report from corresponding Chinese Application No. 201780049836.2 dated Jul. 27, 2022 with English Translation of Office Action.

* cited by examiner

Figure 10
Figure 10A
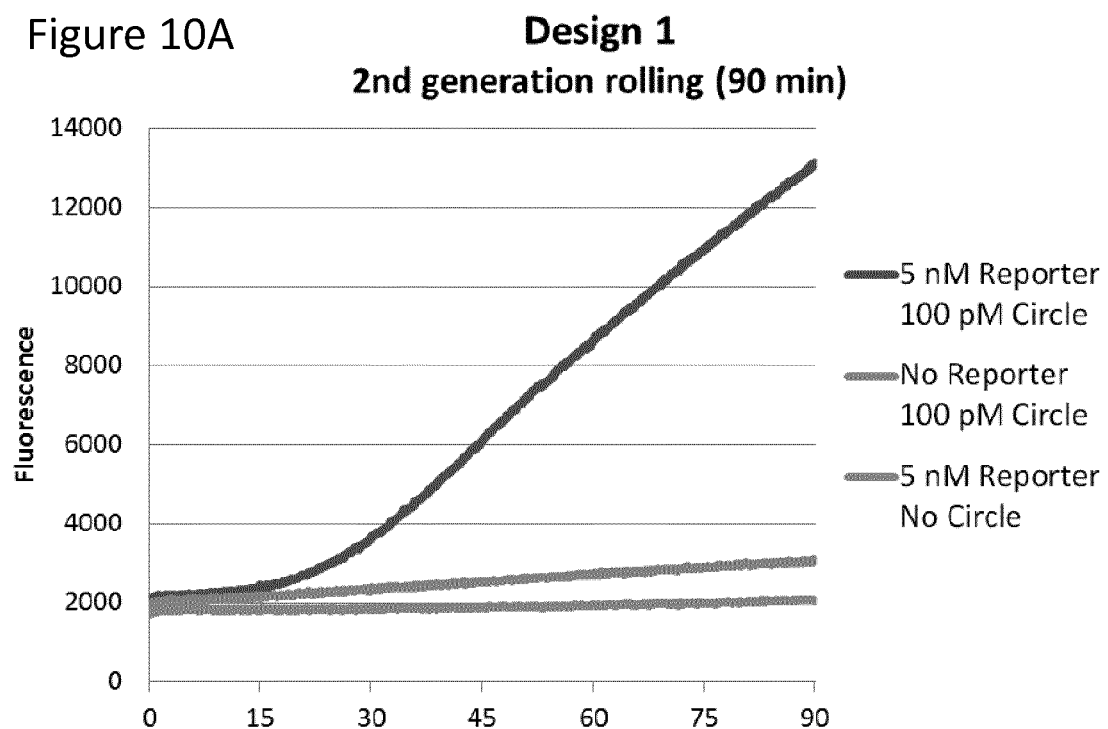
Figure 10B
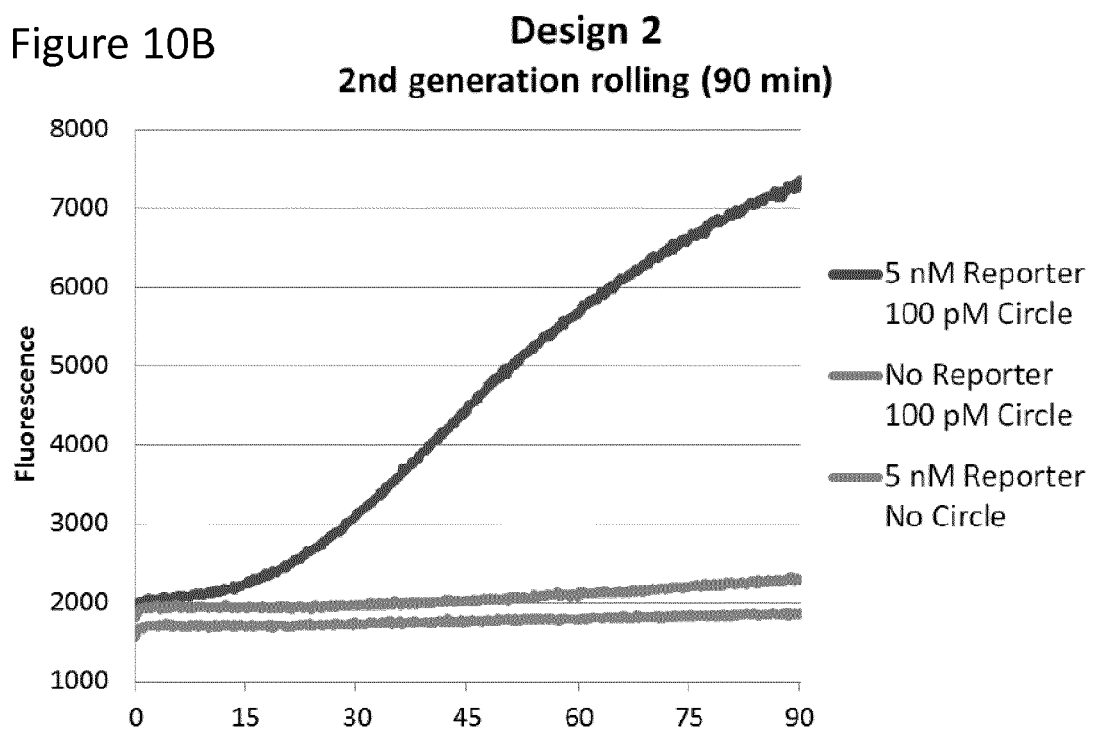

No template, no probe

Template, no probe

No template, probe

Template, probe

Figure 12
Figure 12A
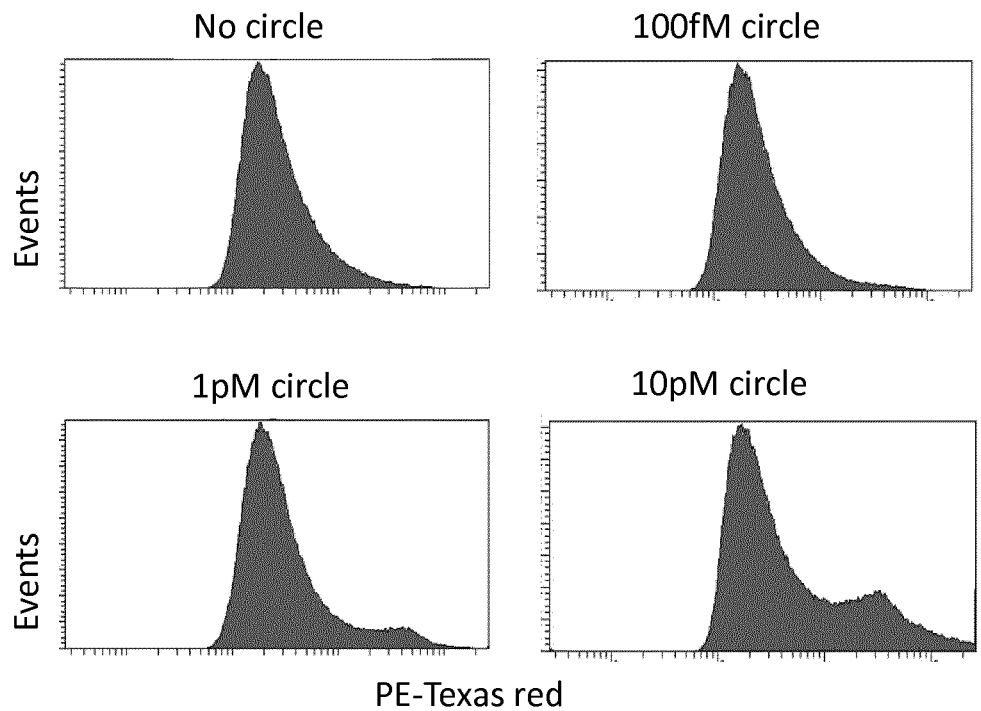
Figure 12B
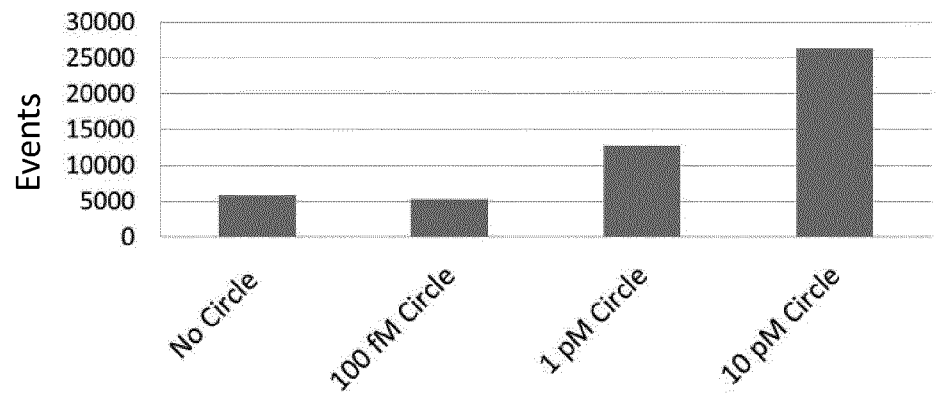

Figure 14
Figure 14A
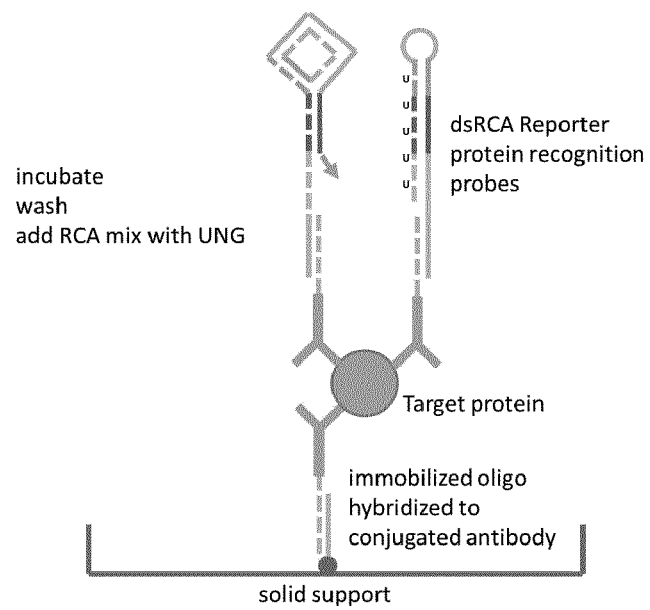
Figure 14B
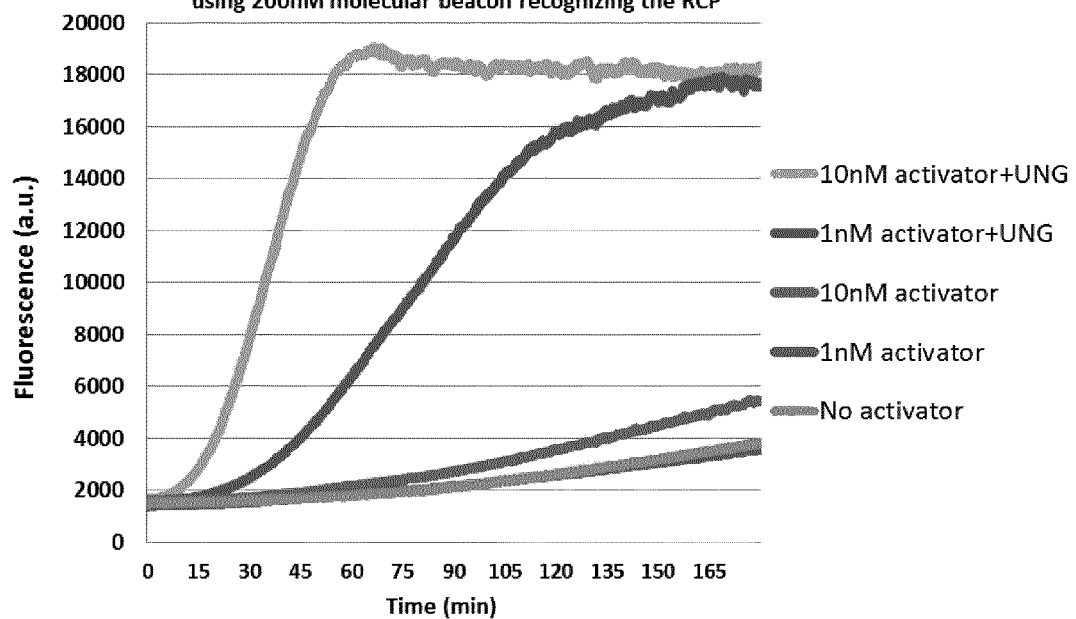

100 pM target (3000 blobs)    10 pM target (501 blobs)

100 pM target no UNG (116 blobs)   No target (8 blobs)

Figure 15B    100 nM compaction oligo 100 pM target    50 pM target

No compaction oligo

SEQUENCE LISTING

<160> NUMBER OF SEQ ID NOS: 5

<210> SEQ ID NO 1
<211> LENGTH: 141
<212> TYPE: DNA
<213> ORGANISM: Artificial Sequence
<220> FEATURE:
<223> OTHER INFORMATION: Protector strand 1

<400> SEQUENCE: 1

```
aacagctagg ccagtaccaa cacacacacc aaaccacaaa ttaacacaac accagaagag    60
aaagagacga caatggttac agaacgagaa agaagaaaga agagaagcgc caggatagtt   120
gtgttaattt gcctagctgt t                                             141
```

<210> SEQ ID NO 2
<211> LENGTH: 134
<212> TYPE: DNA
<213> ORGANISM: Artificial Sequence
<220> FEATURE:
<223> OTHER INFORMATION: Protector strand 2

<400> SEQUENCE: 2

```
ttgtgttgag ttgagtagag aggagagaag agaagaaagt aagaagcgcc tggataagaa    60
gagatgcaaa agagacgaca atggttacag aacgagaaat cagaaagaac tttcttctat   120
tctctcctgc gcca                                                     134
```

<210> SEQ ID NO 3
<211> LENGTH: 64
<212> TYPE: DNA
<213> ORGANISM: Artificial Sequence
<220> FEATURE:
<223> OTHER INFORMATION: Template strand

<400> SEQUENCE: 3

```
cattgtcgct cttttgcatc tctttatcct ggcgcttctc tctttctgat ttctcgtctg    60
taac                                                                 64
```

<210> SEQ ID NO 4
<211> LENGTH: 60
<212> TYPE: DNA
<213> ORGANISM: Artificial Sequence
<220> FEATURE:
<223> OTHER INFORMATION: Target 1

<400> SEQUENCE: 4

```
tgggtgttgt gttaatttgt ggtttggtgt gtgtgttggt actggcctag ctgtttggtt    60
```

<210> SEQ ID NO 5
<211> LENGTH: 58
<212> TYPE: DNA
<213> ORGANISM: Artificial Sequence
<220> FEATURE:
<223> OTHER INFORMATION: Target 2

<400> SEQUENCE: 5

```
cttatccagg cgcttcttac tttcttctct tctctcctct ctactcaact caacacaa      58
```

DOUBLE-STRANDED CIRCLE PROBES

The Sequence Listing submitted herewith, entitled "2017-08-15-sequence-listing_ST25.txt", created Jan. 25, 2019 and having a size of 1545 bytes, is incorporated herein by reference.

The present invention relates generally to the detection of an analyte in a sample by rolling circle amplification (RCA), and in particular to the detection of a nucleic acid molecule (a target nucleic acid) in a sample, which may be the analyte for detection or may be indicative of, or a reporter for, the presence of the analyte in the sample. The invention concerns the provision of a new nucleic acid probe for use in rolling circle amplification assays. The probe comprises a double-stranded circular structure which comprises a circular RCA template and which, in the absence of the target nucleic acid molecule, renders the template unavailable for a RCA reaction, and in particular unavailable for the binding of any molecule capable of priming a RCA reaction. This protects the circular template from an RCA reaction until the probe has bound to the target, thereby improving the specificity of the assay. The present invention also provides methods for using such probes in the detection of an analyte, and kits for the same.

Rolling circle replication (RCR) reactions are well described in the art and have been demonstrated to be useful in a variety of assays for the detection of target nucleic acid molecules in a sample, i.e. for the replication or amplification of a target nucleic acid molecule, wherein the replicated or amplified nucleic acid molecule is detected. Accordingly, rolling circle replication commonly is referred to as rolling circle amplification (RCA), and these terms are used interchangeably herein. RCA methods have been developed in which the rolling circle product is further amplified by a hyperbranch or DNA cascade reaction, as described in WO 97/19193 and WO 97/20948, or by a further RCA reaction. Various methods of amplifying a rolling circle product are also described in WO2014/076214, WO2014/076209 and WO2015/071445.

RCA relates to the synthesis of nucleic acid molecules using a circular single stranded nucleic acid molecule, e.g. a circle oligonucleotide, as rolling circle template (a RCA template) and a strand-displacing polymerase to extend a primer which is hybridised to the template. The primer may in certain assays be provided by a target RNA molecule or a target DNA molecule, but can be any nucleic acid molecule which can hybridise to the circular template. The addition of a polymerase and nucleotides starts the synthesis reaction, i.e. polymerisation. As the rolling circle template is endless, the resultant product is a long single stranded nucleic acid molecule composed of tandem repeats that are complementary to the rolling circle template.

RCA reactions often utilise linear nucleic acid molecules, e.g. oligonucleotides such as padlock probes as described in more detail below, which are manipulated to generate circular nucleic acid molecules, typically by ligating the ends of the nucleic acid molecule together, e.g. using a ligase enzyme. For instance, the ends of the nucleic acid molecule may be brought into proximity to each other by their hybridisation to adjacent sequences on a target nucleic acid molecule which acts as a ligation template. The formation of the circular nucleic acid molecule allows it to be copied in a RCA reaction. This reaction may be initiated by adding a primer to the closed circle or a primer may be generated from the target nucleic acid molecule, i.e. ligation template. The RCA product therefore forms part of the initial primer. This can be particularly advantageous because it may allow localised detection of the target nucleic acid, i.e. in embodiments where the nucleic acid molecule used to prime RCA is immobilised the RCA product will also be immobilised.

The RCA product comprises a string of tandemly repeated complementary copies of the circular template nucleic acid molecule. In certain situations, the product may remain attached to a target analyte, and thus rolling circle amplification is of particular utility in the detection of analytes in an in situ context (though homogeneous detection is possible for "in solution" assays). An RCA reaction may result in a 1000-fold amplification of the circle in an hour, based on a circle consisting of approximately 100 nucleotides (though smaller circles may be amplified more quickly). Thus, RCA of a circular oligonucleotide may result in an RCA product that forms a bundle or "blob" of DNA that can be about 1 µm in diameter. The product (i.e. blob) may be detected by the hybridisation of nucleic acid probes (detection probes) conjugated to fluorescent labels which allows the blob to be visualised by fluorescence microscopy (in heterogeneous assays, i.e. in situ) or flow cytometry (in homogeneous assays). In other embodiments, the RCA products may be reduced to monomers by digestion with a restriction enzyme or a ribozyme, e.g. WO 98/38300 and Dahl F et al., Proc Natl Acad Sci USA. 101(13), 4548-53 (2004), which are then detected.

RCA may be used for the detection of any nucleic acid molecule in a sample and typically has been used to detect directly target nucleic acids in cell and tissue samples, e.g. in situ, i.e. localised, detection of nucleic acid molecules, which is of significant interest both for research and diagnostic purposes. However, RCA assays are not limited to use in heterogeneous formats and may also find utility in homogeneous assays (see e.g. WO 2009/037659).

RCA has also been utilised in methods for the detection of other analytes, i.e. analytes other than nucleic acid molecules, such as cells, viruses, proteins, peptides, small molecules etc. In this respect, a variety of assays have been developed in which a nucleic acid molecule may be used to directly or indirectly tag or label a target analyte in a sample and detection of the nucleic acid molecule serves to indicate the presence of the analyte in the sample. In some methods a new nucleic acid molecule may be generated in a sample (i.e. a nucleic acid molecule that was not present in the original sample and was not one of the components added to the sample), for example through the interaction of one or more analyte-binding molecules when they have bound to the target analyte (e.g. the analyte-binding molecules may carry nucleic acid molecule(s) that interact to generate a new nucleic acid molecule). The detection of the generated nucleic acid molecule is indicative of the analyte in a sample, i.e. the generated nucleic acid molecule acts as a marker or proxy for the target analyte.

Various methods that detect a nucleic acid molecule as a marker or proxy for the target analyte, e.g. protein, are well described in the art. For instance, immuno-PCR, immuno-RCA and proximity probe assays may rely on the detection of a nucleic acid molecule as a substitute for detecting the target analyte directly.

Immuno-PCR involves labelling an antibody for a specific target analyte with a nucleic acid molecule. Typically, the target analyte is captured on a substrate, e.g. with a first antibody and contacted with the antibody:nucleic acid complex. Excess antibody may be washed away before the sample is subjected to a polymerase chain reaction (PCR), which is used to amplify the nucleic acid molecule conjugated to the antibody. Detection of the PCR product is indicative of the presence of the analyte in the sample and proportional to the amount of analyte.

Immuno-RCA relies on the same principles as immuno-PCR. The difference is that a circular (or circularisable) oligonucleotide (RCA template) is hybridised to the nucleic acid molecule conjugated to the antibody (the RCA template may be pre-hybridized or added after the antibody has been allowed to interact with the target analyte). The nucleic acid molecule conjugated to the antibody is used as the primer for RCA. Thus, the RCA product is tethered to the antibody that is interacting with the target analyte, thereby allowing localised detection of the analyte in the sample, e.g. in a cell or tissue sample.

A proximity assay relies on the principle of "proximity probing", wherein an analyte is detected by the binding of multiple (i.e. two or more, generally two or three) probes, which when brought into proximity by binding to the analyte (hence "proximity probes") allow a signal to be generated. Typically, at least one of the proximity probes comprises a nucleic acid domain linked to the analyte-binding domain of the probe, and generation of the signal involves an interaction between the nucleic acid moieties and/or a further functional moiety which is carried by the other probe(s). Thus signal generation is dependent on an interaction between the probes (more particularly by the nucleic acid or other functional moieties/domains carried by them) and hence only occurs when the probes have bound to the analyte, thereby lending improved specificity to the detection system. The concept of proximity probing has been developed in recent years and many assays based on this principle are now well known in the art. For example, proximity ligation assays (PLAs) rely on proximal binding of proximity probes to an analyte to generate a signal from a ligation reaction involving or mediated by (e.g. between and/or templated by) the nucleic acid domains of the proximity probes.

Proximity probes of the art are generally used in pairs, and individually consist of an analyte-binding domain with specificity to the target analyte, and a functional domain, e.g. a nucleic acid domain coupled thereto. The analyte-binding domain can be for example a nucleic acid "aptamer" (Fredriksson et al (2002) Nat Biotech 20:473-477) or can be proteinaceous, such as a monoclonal or polyclonal antibody (Gullberg et al (2004) Proc Natl Acad Sci USA 101:8420-8424). The respective analyte-binding domains of each proximity probe pair may have specificity for different binding sites on the analyte, which analyte may consist of a single molecule or a complex of interacting molecules, or may have identical specificities, for example in the event that the target analyte exists as a multimer. When a proximity probe pair come into close proximity with each other, which will primarily occur when both are bound to their respective sites on the same analyte molecule, the functional domains (e.g. nucleic acid domains) are able to interact, for example, nucleic acid domains may be joined to form a new nucleic acid sequence generally by means of a ligation reaction, which may be templated by a splint oligonucleotide added to the reaction, said splint oligonucleotide containing regions of complementarity for the ends of the respective nucleic acid domains of the proximity probe pair. The new nucleic acid sequence thereby generated serves to report the presence or amount of analyte in a sample, and can be qualitatively or quantitatively detected, for example by real-time, quantitative PCR (q-PCR).

Alternatively, rather than being ligated to each other, the nucleic acid domains of the proximity probes when in proximity may template the ligation of one or more added oligonucleotides to each other, including an intramolecular ligation, to circularise one or more added linear oligonucleotides, for example based on the so-called padlock probe principle, wherein the ends of the added linear oligonucleotide(s) are brought into juxtaposition for ligation by hybridising to a template, here one or more nucleic acid domains of the proximity probes (in the case of a padlock probe the target nucleic acid for the probe). Various such assay formats are described in WO 01/61037.

WO 97/00446 and U.S. Pat. No. 6,511,809 disclose a heterogeneous format for proximity ligation assays, i.e. the analyte is first immobilised to a solid substrate by means of a specific analyte-binding reagent.

Homogeneous proximity ligation assays (i.e., in solution) are disclosed in WO 01/61037, WO 03/044231, WO 2005/123963, Fredriksson et al (2002) Nat Biotech 20:473-477 and Gullberg et al (2004) Proc Natl Acad Sci USA 101: 8420-8424.

Not all proximity assays are based on ligation, and the interaction of nucleic acid domains of proximity probes may comprise an extension reaction—for example the nucleic acid domains may hybridise to one another and one or both of the domains may template the extension of the other. The extension product may then be detected, for example by means of a padlock probe which hybridises to the extension product and which may itself be detected by an RCA reaction.

It will be evident that RCA may be of utility in the specific detection of any nucleic acid molecule in a sample, regardless of whether it is the "original" target analyte in a sample or it is a "proxy" or "marker" for the target analyte generated by the interaction of specific detection molecules, e.g. proximity probes, with the target analyte, e.g. protein. Similarly, RCA may be useful in the detection of amplified nucleic acid molecules. For instance, in samples in which the target nucleic acid molecule is present in particularly low amounts, e.g. rare transcripts, rare viral genomes etc., RCA can be used to enhance the detection of the nucleic acid molecule for detection. In some instances the nucleic acid molecule for detection may itself be a RCA product. Thus, a RCA reaction may be useful to amplify a primary RCA product, i.e. to produce secondary RCA products. Secondary RCA products may also be the target for further RCA reactions, i.e. to produce tertiary RCA products, and so on.

Circular nucleic acid molecules, generated by circularisation of a linear oligonucleotide or provided as a pre-formed circle (pre-circularised), which act as the amplification template for rolling circle amplification, are known to bind in a non-specific manner to single-stranded oligonucleotides present in a sample. A bound oligonucleotide comprising a free 3' end can act as a primer for the initiation of rolling circle amplification, resulting in non-specific initiation of rolling circle amplification. Thus, an RCA product may be generated from the non-specific initiation (priming) of an RCA reaction, which is indistinguishable save for a small region at its 5' end from an RCA product formed as an indicator for the presence of a target nucleic acid in a sample, and this can contribute to the background signal generated during an RCA-based detection assay. This is a particular problem where a pre-circularised nucleic acid molecule is provided in an RCA-based detection assay, as the lack of the requirement for a target-dependent circularisation step allows comparatively higher levels of non-specific initiation of rolling circle amplification to take place.

The ligation of a linear (padlock) probe in RCA-based detection methods is also known to be a source of background signal, as ligation may be templated to a degree by non-specific (i.e. non-target) nucleic acid molecules present in a sample. Thus, where detection is dependent on the formation of a circular nucleic acid template for RCA (i.e. where the formation of a circular nucleic acid template is indicative of the presence of a target analyte in a sample), templating of circularisation by a non-specific nucleic acid molecule may lead to the target-independent generation of a detectable signal, thus increasing background signal generated in the detection method.

Despite the existence of a plurality of methods for the sensitive, rapid and convenient detection or quantification of one or more analytes, e.g. nucleic acid molecules, in a sample, there is a continuous need to develop assays with increased sensitivity, e.g. improved signal to noise ratio. There is also a desire to simplify assays to reduce errors and inefficiencies that arise from a large number of steps, e.g. handling errors, and to reduce costs and reaction times.

Various strategies involving the use of novel probes have been developed in order to improve the signal to noise ratio of an RCA-based detection assay. Probes providing the components necessary for an RCA reaction, which require activation by target-dependent cleaving and/or unfolding before the RCA reaction can take place are provided in WO2014/076214. Further probes which undergo target-dependent cleavage and circularisation are provided in PCT/EP2015/067723, and probes which hybridise to a target nucleic acid molecule and provide a primer for extension using the target nucleic acid molecule as a template prior to templating the circularisation of the resulting extension product are provided in PCT/EP2015/067725. However, there remains a need for probes which can enhance the specificity and sensitivity of an RCA-based detection assay without increasing the complexity or difficulty of performing the assay. This is addressed by the present invention.

The present invention accordingly provides new probes, which are designed to reduce the complexity of a RCA-based assay and which reduce non-specific (target-independent) generation of a RCA product (RCP) in the detection of a target nucleic acid when a probe comprising a pre-formed circular RCA template is used. The new probes comprise a pre-formed circular nucleic acid molecule (the RCA template) and protect it, within a double-stranded structure, from being able to template a RCA reaction until the circle can be released from the double-stranded structure by (or in) the presence of the target nucleic acid molecule. In effect, the double-stranded circular structure prevents the binding of oligonucleotides to the circular RCA template, or the priming of an RCA reaction, until the probe is activated by a strand displacement reaction which involves the binding of the probe to its target molecule (i.e. a target-dependent activation of the probe). Thus, non-specific (i.e. target-independent) RCA is reduced, thereby reducing the background signal (target-independent signal) generated during the course of an RCA-based detection reaction, and increasing both the specificity and sensitivity of the assay.

The present invention accordingly and advantageously allows a pre-formed circular nucleic acid molecule to be used as the template for an RCA reaction, by providing a probe in which the circular nucleic acid molecule is protected from non-specific binding of oligonucleotides present in a sample by at least one 'protector' nucleic acid strand which is hybridised to the circular nucleic acid molecule, and thus which is prevented from giving rise to an unwanted RCA product. The probe itself is not able to undergo a RCA reaction until it has bound to its target. Binding of the probe to a target nucleic acid releases (i.e. makes accessible) the circular nucleic acid template, or a primer-template complex, and allows the initiation of RCA by a primer having a free 3' end, and subsequent amplification of the circular template. Alternatively put, the present invention allows a template for an RCA reaction to be added to a sample as a preformed circular nucleic acid molecule, whilst preventing the accidental, non-specific initiation of RCA by an oligonucleotide present in the sample. This is achieved by providing the circular nucleic acid molecule as a double-stranded circular structure in a probe which also comprises a target binding site. The circle thus only becomes available to act as a template for RCA in the presence of the correct target nucleic acid molecule, and thus non-specific initiation of RCA may be avoided. Furthermore, the present invention allows a target-dependent ligation step (a circularisation step) to generate a RCA template to be dispensed with in the course of a detection assay, further improving the sensitivity of RCA-based detection methods.

At its broadest, the present invention provides a nucleic acid probe for detection of a target nucleic acid molecule by an RCA reaction, wherein said probe is able to undergo a RCA reaction in the presence of the target nucleic acid molecule, said probe comprising:

(i) a first circular template strand which is capable of acting as a template for RCA; and (ii) at least a second protector strand (i.e. one (second) protector strand or two or more (second and third or more) protector strands) which protects the first strand from RCA in the absence of the target nucleic acid molecule, wherein at least one protector strand (i.e. at least one of the second and/or further protector strands) comprises a target binding site;

wherein the second or further (i.e. the second and any further) protector strand(s) comprise a region of complementarity to the first template strand and are hybridised thereto to form a double-stranded circular structure containing the first template strand inside the protector strand(s), thereby inhibiting RCA of the first template strand, and wherein a second and/or further protector strand further comprises at least a first single-stranded region which comprises at least an accessible part of the target binding site which allows the probe to bind to a complementary binding site in the target nucleic acid molecule, such that upon binding of the probe to the target nucleic acid molecule the probe is able to undergo a strand displacement reaction which allows RCA of the first template strand.

Thus, the probe comprises one or more protector strands (or alternatively put, at least one protector strand), and therefore comprises at least two strands, the first template strand and a second protector strand, and optionally one or more further protector strands. At least one of the second, or where present further, protector strands comprises the target binding site.

Where a probe comprises two or more protector strands which each comprise a target binding site, the target binding sites in the two or more protector strands may be the same (i.e. for the same sequence within a target nucleic acid molecule) or may be different (i.e. for different sequences within the same target nucleic acid molecule or for different target nucleic acid molecules).

Thus, where a probe comprises two or more protector strands, each comprising a different target binding site, the respective target binding sites in the two or more protector strands may each be complementary to the separate regions in the same target molecule, and may bind to such regions (i.e. cognate, complementary sequences) in the target molecule. Such regions in the target nucleic acid molecule may, in certain embodiments be located adjacent to one another in the target nucleic acid molecule, or may be near to one another in the target nucleic acid molecule. Alternatively, in other embodiments, the different regions in the target nucleic acid molecule may be spatially separate. Therefore, in such embodiments, the separate regions may be viewed as each forming a part of the binding site, or each being partial binding sites within the target nucleic acid molecule, for the nucleic acid probe of the present invention.

In certain embodiments, in which a probe comprises two or more protector strands, each comprising a different target binding site, wherein each target binding site is for a different target nucleic acid molecule, the different target nucleic acid molecules may be located in proximity to one another.

It will be understood that where the probe comprises two or more protector strands (i.e. a second and one or more further protector strands) they each comprise a region of complementarity to the first template strand. Such a region of complementarity within a second or further protector strand is hybridised to the first template strand, thereby rendering it inaccessible to the binding of other nucleic acid molecules and may thus be viewed as a "protecting region". The second protector strand and/or, where present, one or more of the further protector strands comprises a target binding site (or more particularly comprises at least a first single-stranded region which comprises at least an accessible part of a target binding site, which allows the probe to bind to a complementary binding site in the target nucleic acid molecule).

The protector strand(s) may thus be seen to form, singly (where there is one protector strand) or together (where there are two or more protector strands), an envelope which is complementary to the first template strand, and which is hybridised thereto to form a double-stranded circular structure containing the first template strand inside the envelope. Put another way, the protector strand(s) provide (or together provide) a "circle" around the template in order to prevent non-specific amplification.

Where the probe comprises a single (i.e. one) second protector strand, the envelope may be seen as a loop. Accordingly, in this embodiment the second protector strand forms a loop which is complementary to the first template strand and is hybridised thereto to form a double-stranded circular structure containing the first template strand inside the loop. The loop may be seen as, or to represent, the "protecting region".

Where the probe comprises more than one protector strand (i.e. two or more protector strands), the second and third or more (or second and further) protector strands, when hybridised to the first circular template strand, together form the envelope (i.e. the circle around the template) which protects the first template strand (i.e. within the double-stranded structure). In other words, the second and further protector strands together form a double-stranded circular structure when hybridised to the first circular template strand.

As explained further below, not all of the bases of the first template strand need be based-paired to the protector strand(s) in the double-stranded structure, nor must the regions of complementarity of the protector strand(s) be completely (or absolutely) complementary to the first template strand, as long as there is sufficient hybridisation between the strands for a substantially double-stranded circular structure to form, which is sufficient to render the first circular template strand unable to participate in a RCA reaction.

Thus, at least one second protector strand may be hybridised to the first circular template strand to prevent the non-specific (target-independent) activation of RCA. As noted above, this provides a "circle" around the template which prevents non-specific amplification. It can be seen therefore that the first circular template strand lies (or is provided) inside a double-stranded circular structure. In an embodiment where the probe comprises only a single protector strand the second protector strand may comprise a region of complementarity to the entire first circular template strand. In this way, the second protector strand may form a loop which is complementary to the first template strand, and is hybridised thereto to form a double-stranded circular structure containing the first template strand inside the loop. However, in other embodiments, the probe may comprise two or more (i.e. second and further) protector strands, which combine to form the envelope which protects the first template strand, and thus together may provide the circle around the template. In such embodiments, the envelope may comprise two or more protector strands. In such embodiments, the second and further protector strands may each comprise a region of complementarity to a portion (a part or a region) of the first circular template strand, but the two or more protector strands between them comprise regions of complementarity to the entire first circular template strand (or more particularly, substantially to the entire first circular template strand).

In either case, the first template strand is hybridised to the second protector strand or strands, and is thus protected from giving rise to an unwanted RCA product in the absence of a target nucleic acid molecule.

Thus, in certain embodiments, the probe of the present invention may comprise a single, second, protector strand, and thus a probe of the invention may comprise:
(i) a first circular template strand which is capable of acting as a template for RCA; and
(ii) a second protector strand which protects the first strand from RCA in the absence of the target nucleic acid molecule, and which comprises a target binding site;
wherein the second protector strand forms a loop which is complementary to the first template strand and is hybridised thereto to form a double-stranded circular structure containing the first template strand inside the loop, thereby inhibiting RCA of the first template strand, and wherein the second protector strand further comprises at least a first single-stranded region which comprises at least an accessible part of the target binding site which allows the probe to bind to a complementary binding site in the target nucleic acid molecule, such that upon binding of the probe to the target nucleic acid molecule the probe is able to undergo a strand displacement reaction which allows RCA of the first template strand.

However, in further embodiments, the probe may comprise two or more (i.e. second and third or more) protector strands. Thus, in certain embodiments, the probe may comprise:
(i) a first circular template strand which is capable of acting as a template for RCA; and
(ii) two or more protector strands which protect the first strand from RCA in the absence of the target nucleic acid molecule, wherein at least one of the protector strands comprises a target binding site;
wherein the two or more protector strands form an envelope which is complementary to the first template strand and is hybridised thereto to form a double-stranded circular structure containing the first template strand inside the envelope, thereby inhibiting RCA of the first template strand, and wherein a (which includes that at least one) protector strand further comprises at least a first single-stranded region which comprises at least an accessible part of the target binding site which allows the probe to bind to a complementary binding site in the target nucleic acid molecule, such that upon binding of the probe to the target nucleic acid molecule the probe is able to undergo a strand displacement reaction which allows RCA of the first template strand.

A probe comprising two protector strands is shown in FIG. 21 and in FIG. 26.

The circular nucleic acid molecule (first circular template strand) provided in the probe of the present invention is not capable of interacting with oligonucleotides present in the sample in the absence of the target nucleic acid molecule. Binding of the target nucleic acid molecule "activates" the nucleic acid probe, or allows the probe to be activated, in the sense of allowing or permitting it to undergo a RCA reaction. This means that the probe is able to provide a template, which is accessible for a RCA reaction. Whilst in some embodiments a primer-template complex may be provided by the probe when activated (i.e. the probe provides the primer) the term "able to undergo a RCA reaction" does not require the probe to provide the primer for RCA, merely a template; the primer can be separately provided. In some embodiments, where a separate activator molecule is provided (see further below), the activator may provide the primer.

In particular, binding of the target molecule directly or indirectly induces the probe to undergo a conformational change (in the form of a strand displacement reaction). The probe may therefore be seen to be an "activatable" probe, that is, to be capable of being activated in the presence of a target nucleic acid, and the specificity of the probe (i.e. the target nucleic acid sequence detectable by the probe) is determined by the protector strand, specifically by the target binding site within the protector strand. Whilst activation may be direct i.e. mediated by the target nucleic acid molecule, or indirect i.e. mediated by a further nucleic acid molecule binding to the target nucleic acid probe, that may act as a separate activator molecule, activation may only take place upon binding of the target nucleic acid probe to the target molecule, and is thus dependent upon and indicative of the presence of a target nucleic acid molecule in a sample.

Thus, the present invention may be seen to provide a nucleic acid probe which is activatable in the presence of the target nucleic acid molecule to undergo a RCA reaction, said activation being achieved by an activator (i.e. an activator for the RCA reaction) being either the target nucleic acid molecule or a separate activator molecule binding to the target nucleic acid, said probe comprising:
  (i) a first circular template strand which is capable of acting as a template for RCA; and
  (ii) at least a second protector strand which protects the first strand from RCA in the absence of the target nucleic acid molecule, wherein at least one of the second or further protector strands comprises a target binding site and wherein optionally at least one second or further protector strand comprises a binding site for the separate activator molecule;
wherein the second and where present further protector strands comprise a region of complementarity to the first template strand (e.g. form an envelope which is complementary to the first template strand) and are hybridised thereto to form a double-stranded circular structure containing the first template strand inside the protector strands (e.g. inside the envelope), thereby inhibiting RCA of the first template strand, and wherein a second and/or further protector strand further comprises at least a first single-stranded region which comprises at least an accessible part of the target binding site which allows the probe to bind to a complementary binding site in the target nucleic acid molecule, and wherein optionally a second and/or further protector strand comprises a second single-stranded region which comprises at least an accessible part of the binding site for the separate activator molecule, such that upon binding of the probe to the target nucleic acid molecule the probe is able to undergo a strand displacement reaction mediated by the target nucleic acid molecule or by the separate activator molecule when bound to the target molecule, to allow RCA of the first template strand.

Where there is only one protector strand (only a second protector strand) then both first and second single-stranded regions will be on the same strand. Where there are two or more protector strands, the same (second or further) protector strand may comprise both the first and second single-stranded regions, e.g. a second protector strand may provide both the first and second single-stranded region (see for example FIG. 26). However, in other embodiments a different second or further protecting strand may comprise the (optional) second single-stranded region.

In other embodiments, each (second and/or further) protecting strand may comprise a first and a second single-stranded region, i.e. each strand may comprise a target binding site as hereinbefore described, and may further comprise a binding site for the separate activator molecule.

In one particular embodiment, the present invention accordingly provides a nucleic acid probe which is activatable in the presence of the target nucleic acid molecule to undergo a RCA reaction, said activation being achieved by an activator (i.e. an activator for the RCA reaction) being either the target nucleic acid molecule or a separate activator molecule binding to the target nucleic acid, said probe comprising:
  (i) a first circular template strand which is capable of acting as a template for RCA; and
  (ii) a second protector strand which protects the first strand from RCA in the absence of the target nucleic acid molecule, and which comprises a target binding site and optionally a binding site for the separate activator molecule;
wherein the second protector strand forms a loop which is complementary to the first template strand and is hybridised thereto to form a double-stranded circular structure containing the first template strand inside the loop, thereby inhibiting RCA of the first template strand, and wherein the second protector strand further comprises at least a first single-stranded region which comprises at least an accessible part of the target binding site which allows the probe to bind to a complementary binding site in the target nucleic acid molecule, and optionally a second single-stranded region which comprises at least an accessible part of the binding site for the separate activator molecule, such that upon binding of the probe to the target nucleic acid molecule the probe is able to undergo a strand displacement reaction mediated by the target nucleic acid molecule or by the separate activator molecule when bound to the target molecule, to allow RCA of the first template strand.

In yet another embodiment of an activatable probe, the present invention provides a nucleic acid probe comprising:
  (i) a first circular template strand which is capable of acting as a template for RCA; and (ii) two or more protector strands which protect the first strand from RCA in the absence of the target nucleic acid molecule, wherein at least one of the protector strands comprises a target binding site;

wherein the two or more protector strands form an envelope which is complementary to the first template strand and is hybridised thereto to form a double-stranded circular structure containing the first template strand inside the envelope, thereby inhibiting RCA of the first template strand, and wherein a (which includes that at least one) protector strand further comprises at least a first single-stranded region which comprises at least an accessible part of the target binding site which allows the probe to bind to a complementary binding site in the target nucleic acid molecule, and optionally a (which includes at least one) protector strand (which may be the same or different) further comprises a second single-stranded region which comprises at least an accessible part of the binding site for the separate activator molecule, such that upon binding of the probe to the target nucleic acid molecule the probe is able to undergo a strand displacement reaction mediated by the target nucleic acid molecule or by the separate activator molecule when bound to the target molecule, to allow RCA of the first template strand.

Activation of the probe is required to enable a RCA reaction to proceed, e.g. to provide a template for RCA, and may be performed by the target nucleic acid molecule or by a separate activator molecule binding thereto. In other words, the target nucleic acid molecule may function as the activator of the probe (and hence of the RCA reaction), or the probe activator may be a separate activator molecule which is provided together with the probe, and which in use is recruited by or to the target nucleic acid molecule to induce the strand displacement reaction which activates the probe.

Activation by a separate activator molecule requires it to bind to the target molecule before activation can take place. Accordingly, in either case, in the absence of the target nucleic acid molecule, the probe will not bind to its activator, and thus will not be activated or provide a template, or primer/template complex, for a RCA reaction.

FIGS. 1 and 2, and 3 and 4 respectively depict two different probe designs in which the probe is activated by its target nucleic acid molecule. FIGS. 14, 18, 23, 24, 25 and 26 depict probe designs in which the probe is activated by a separate activator molecule, which is itself recruited by binding to the target molecule. The target molecule thus binds both the probe and the separate activator molecule, and brings them together in proximity, to allow the separate activator molecule to interact with and activate the probe. This is described in more detail below.

The term "recruits" is used herein to mean that the target nucleic acid molecule binds to the separate activator molecule, and thereby brings it into proximity with the probe (which is also bound to the target molecule), allowing it to interact with (i.e. bind to) the probe, and to activate the probe. Thus, the target molecule is capable of binding simultaneously to both the probe and the separate activator molecule, bringing them into proximity and thereby facilitating or enabling their interaction. In other words, the probe is capable of binding simultaneously to both the target molecule and to the separate activator molecule (i.e. the probe has separate and distinct binding sites for the target and separate activator molecules, specifically binding sites which are at least partially accessible for binding, and conversely the target molecule has separate and distinct binding sites for the probe and separate activator molecule).

In this manner, activation of the probe by the separate activator molecule is target-dependent.

Binding of the target nucleic acid molecule to the separate activator molecule may be direct (i.e. the target nucleic acid molecule binds to a portion of the separate activator molecule), or be indirect (i.e. the target nucleic acid molecule binds to the separate activator molecule by an intermediary molecule). Indirect binding mediated by an intermediary molecule may take place where the intermediary molecule is bound to the target nucleic acid molecule, or may take place where the intermediary molecule is situated in proximity to the target nucleic acid molecule, e.g. in a heterogeneous assay format or in an in situ format, in which the target nucleic acid molecule and the intermediary molecule are both bound to a common surface or molecule (i.e. they co-localise). In certain embodiments, the nucleic acid probe and separate activator molecule may thus bind to different molecules, which binding may still result in the activation of the nucleic acid probe as described herein.

The activator (i.e. the target nucleic acid or a separate activator molecule) binds to the probe via a single-stranded region of the (or one of the) second protector strand(s), and thus comprises a region of complementarity to a sequence in the single-stranded region. In other words, the activator, be it the target molecule or a separate activator molecule, comprises a binding site for the probe (more particularly for a sequence in a single-stranded region of the probe). If the activator is a separate activator molecule it also comprises a binding site for the target molecule (i.e. a region of complementarity to a sequence in the target molecule, which target sequence is distinct to the sequence (binding site) in the target molecule which binds to the probe), or as noted above, for an intermediary molecule situated in proximity thereto.

The probe comprises at least a first single-stranded region comprising at least an accessible part of the target binding site. Where the probe is activated by a separate activator molecule it may also comprise a second single-stranded region comprising at least an accessible part of a binding site for the separate activator molecule (a "separate activator binding site"). The first and second single-stranded regions may be part of a single, or the same, single-stranded part of the probe (i.e. adjacent in the same protector strand). However, as described further below, the first and second single-stranded regions may be spatially separated within a protector strand. In particular they may lie at (or towards) different ends of the second (or one of the) protector strand(s), for example at either end of the double-stranded circular structure. This is depicted for example in FIG. 23. Furthermore, in embodiments of the present invention in which the probe comprises two or more protector strands, the first and second single-stranded regions may be located in the same protector strand, or may be situated in different protector strands, and/or each of the second and/or further protector strands may comprise a first and/or a second single-stranded region.

The single-stranded region(s) of the probe are, or comprise, a part or a portion of the binding site for the activator (i.e. a part or portion of the activator binding site), and the binding site for the activator (be it the target nucleic acid molecule or the separate activator molecule) extends beyond the single-stranded region, i.e. into a region which is at least partially double-stranded or hybridised to a complementary sequence within the probe (e.g. into the double stranded circular structure). Thus, part of the binding site in the probe for the activator (target or separate activator molecule) is accessible for binding by the activator when it is in contact with the probe, but part is not accessible (i.e. in the sense of not immediately accessible), as it is contained in a double-stranded region or structure. The binding site for the activator (i.e. the target nucleic acid or the separate activator molecule) is thus partially single-stranded, and further comprises a double-stranded portion, in which the "activator" binding site portion is hybridised to another part of the probe (a complementary sequence in the first circular template strand and/or a complementary sequence in the same (e.g. second) protector strand or a further protector strand). Hence, when, the activator (target nucleic acid molecule or separate activator molecule) binds to the accessible part of its binding site in the probe, a strand displacement occurs, as the "activator" invades the double-stranded structure (which contains the "inaccessible" part(s) of the "activator" binding site), causing the double-stranded (duplex) part to be opened up, or unfolded, at least in part. In other words, binding of the "activator" to the accessible part of its binding site (in the first or second single-stranded region) allows the "activator" to bind to a further part or portion of the activator binding site (target binding site or binding site for a separate activator molecule), wherein the binding of the activator to the activator binding site displaces a complementary sequence therefrom and activates the probe.

In this way, binding of the activator for the RCA reaction (i.e. the activator of the probe, be it the target or the separate activator molecule) causes a strand displacement reaction to activate the probe, which in turn allows RCA of the first template strand to take place.

Upon binding of the probe to the target molecule or separate activator molecule, the probe undergoes a conformational change comprising at least partially interrupting the Watson-Crick base pairing between a pair of antiparallel nucleotide sequences within the probe, mediated by strand invasion by the target nucleic acid molecule or separate activator molecule (i.e. the activator for the probe). The activator binds to the target nucleic acid molecule via a single-stranded region in a (e.g. second) protector strand and induces strand displacement of a nucleotide sequence hybridised thereto (or to a further protector strand), thereby activating the probe.

The term "accessible" as used herein (e.g. in the context of a binding site for the target or separate activator molecule) thus means simply that that part of the binding site is available for binding when the probe is contacted with the target nucleic acid and/or separate activator molecule. Thus, this part of the binding site is exposed (i.e. single-stranded) and (immediately) available for binding. Conversely, an "inaccessible" part of the binding site means that the activator or target cannot bind to that part until it is rendered available for binding by a strand displacement reaction, e.g. exposed, or released. Accordingly, an inaccessible part of the binding site is protected from binding until the probe is activated.

An accessible part of a binding site may thus be seen as a "toehold", which allows binding to take place.

The different, accessible and inaccessible, parts of a binding site may be seen as different domains of a binding site (e.g. a binding site in the probe for the target or separate activator molecule). The accessible part (i.e. the toehold) of a target binding site or separate activator binding site may be viewed as a first domain (i.e. a first accessible domain) and the binding site may contain one or more further domains which lie in double-stranded part(s) of the probe, including but not necessarily, in the double-stranded circular structure. As described in more detail below, in a simple configuration as shown for example in FIGS. 1 to 4, the probe may comprise a stem-loop structure (more particularly the double-stranded circular structure may be part of a stem-loop structure of the probe), e.g. with the second protector strand forming a stem (alternatively expressed, the loop of the stem-loop structure may be part of the double-stranded structure). However, other stem, or stem-loop structures, may also be present in the probe (see e.g. FIG. 21, 25 or 26). Thus, the probe may comprise one or more stems in addition to the envelope (or loop) structure, with the envelope (or loop) being part of the double-stranded circular structure. The second or other domains of the binding site may lie in a double-stranded region (duplex) of the envelope (i.e. the double-stranded circular structure) and/or the stem of the probe (or of another (i.e. a separate) stem-loop structure within the probe).

Binding of the target or separate activator molecule to the first (accessible) domain of its binding site (in the first or second single-stranded region) is followed by binding to the second and any further (inaccessible) domains of the binding site, which binding displaces the sequences hybridised to the second or further domains and causes the duplex structure to open, or unfold. This opening/unfolding activates the probe, for example by causing the second (or one of the) protector strand(s) to dissociate at least partially from the first circular template strand, exposing a single-stranded region of the first circular template strand, thereby allowing a primer for RCA to bind (e.g. as shown in FIGS. 3 and 4, 21 or 23), or by allowing a primer/template complex to form when the duplex structure is unfolded (e.g. as shown in FIGS. 1 and 2).

Where the probe is designed to be activated by a separate activator molecule, the target binding site in the first single stranded region (or a target binding site in a single-stranded region of a second or further protector strand) may simply be designed to be fully accessible i.e. it may have a single accessible domain lying in the (or a) first single-stranded region. This is shown in FIG. 23. More particularly, the first single-stranded region may constitute the target binding site. Thus in such an embodiment, target binding serves simply to recruit the separate activator molecule and does not in itself cause a strand displacement in the probe.

In one embodiment, the (or a) target binding site may only be partially accessible (the first single-stranded region), and part of the target binding site (i.e. further binding domains) may be hybridised to a complementary sequence in another part of the probe, wherein the complementary sequence may be a portion of the binding site in the probe for the separate activator molecule. Such a situation is depicted in FIG. 25, and can be seen to provide a probe for use in methods for homogenous double recognition of the target. Hence, when the target nucleic acid molecule binds to the accessible part of its binding site in the probe (first accessible binding domain), a strand displacement may occur, as the target nucleic acid molecule displaces the sequence hybridised to the target binding site (to a second, initially inaccessible, binding domain), thereby exposing at least the accessible part or portion of the binding site for the separate activator molecule, but without itself activating the probe. In other words, in certain embodiments binding of the target nucleic acid molecule to the accessible part (domain) of its binding site may allow the target nucleic acid molecule to bind to a further part or portion (domain) of the target binding site, wherein the binding of the target nucleic acid molecule to its binding site displaces a complementary sequence therefrom and exposes, or makes accessible, the first domain of the separate activator binding site.

The first domain of the (or a) separate activator binding site may therefore be inaccessible in the absence of the target nucleic acid molecule, and be exposed or become accessible only after the binding of the target nucleic acid molecule to the probe. In such an embodiment, the first domain of the separate activator binding site may be situated within a metastable secondary structure (e.g. a hairpin or a stem loop structure), and only becomes accessible (e.g. through unfolding or opening of the metastable secondary structure) upon binding of the nucleic acid probe to the target nucleic acid molecule. The first domain of the separate activator binding site may therefore be complementary to at least a portion of the target binding site, or in other words, may have homology to at least a portion of the target nucleic acid molecule.

Thus, in certain embodiments, the activation of the probe may require two separate and distinct conformational changes to occur, mediated by separate strand invasion events; a first, mediated by strand displacement by the target nucleic acid molecule (which exposes the second single-stranded region), and a second, mediated by strand displacement by the separate activator molecule (which activates the probe).

In the absence of the target nucleic acid molecule, at least one protector strand is hybridised to the first circular template strand, thereby blocking the binding of nucleic acid molecules to the first circular template strand, and thus preventing initiation of an RCA reaction. The probe structure is also unable itself to prime a RCA reaction in the absence of the target molecule. This is of particular utility as it may prevent the non-specific binding of nucleic acid molecules present in a sample to the RCA template, thereby preventing the non-target specific initiation of RCA. The conformational changes which occur upon binding of the probe to the target nuclei acid molecule (i.e. the activation of the probe via a strand displacement as hereinbefore described) may be seen as releasing the first circular template strand such that RCA using the first template strand may be initiated. In some embodiments, binding of the activator for the RCA reaction may release the amplification template from its circle (from within the double-stranded circular structure). Thus, such releasing may comprise a strand displacement in the double-stranded circular structure, but as shown in FIGS. 1 and 2 this is not necessary, and the first circular template strand may be released for RCA by a primer/template complex being allowed to form, comprising the double-stranded circular structure. This is described in more detail below.

In one embodiment, the activator for the probe is the target nucleic acid molecule, and the first single-stranded region of the second (or of a further) protector strand forms, or comprises, an accessible part (or domain) of the target binding site. In such an embodiment, binding of the target nucleic acid molecule to the first single-stranded region of the probe displaces a complementary sequence hybridised to the target binding site, thereby activating the probe.

In this embodiment, the present invention provides a nucleic acid probe which is activatable by the target nucleic acid molecule to undergo a RCA reaction, said probe comprising:
  (i) a first circular template strand which is capable of acting as a template for RCA; and
  (ii) at least a second protector strand which protects the first strand from RCA in the absence of the target nucleic acid molecule, wherein at least one of the second and/or further protector strands comprises a target binding site;
wherein the second and any further protector strand(s) comprise a region of complementarity to the first template strand (e.g. forms an envelope (e.g. a loop) which is complementary to the first template strand) and are hybridised thereto to form a double-stranded circular structure containing the first template strand inside the protector strand (e.g. inside the envelope, or loop), thereby inhibiting RCA of the first template strand, and wherein a second and/or further protector strand further comprises a first single-stranded region which comprises an accessible part of the target binding site which allows the probe to bind to a complementary binding site in the target nucleic acid molecule, such that upon binding of the probe to the target nucleic acid molecule the probe is able to undergo a strand displacement reaction mediated by the target nucleic acid molecule to allow RCA of the first template strand.

In an alternative embodiment, the activator for the probe is a separate activator molecule, and the probe comprises a second and/or further protector strand, wherein at least one of the second and/or further protector strands comprises a first single-stranded region which forms or comprises part of a target binding site and at least one of the second and/or further protector strands (optionally the same protector strand) comprises a second single-stranded region which forms or comprises part of the binding site for the separate activator molecule. In such an embodiment, the nucleic acid probe binds to the target nucleic acid molecule by the or a first single-stranded region or regions, and binding of a separate activator molecule (recruited by the target nucleic acid molecule) to the second single-stranded region of the probe displaces a complementary sequence hybridised to the binding site for the separate activator molecule, thereby activating the probe.

Thus, in certain embodiments, the probe may comprise two or more protector strands, which comprise first and second single-stranded regions in the same or different protector strands.

In such embodiments, the present invention thus provides a nucleic acid probe which, in the presence of the target nucleic acid molecule, is activatable to undergo a RCA reaction, the activator for said RCA reaction being a separate activator molecule binding to the target nucleic acid, said probe comprising:
  (i) a first circular template strand which is capable of acting as a template for RCA; and
  (ii) at least a second protector strand which protects the first strand from RCA in the absence of the target nucleic acid molecule, and which second and optionally one or more further protector strands comprise a target binding site and a binding site for the separate activator molecule (i.e. which binding sites may be on the same or different protector strands);
wherein the second and where present further protector strand comprise a region of complementarity to the first template strand (e.g. form an envelope (e.g. a loop) which is complementary to the first template strand and is hybridised thereto to form a double-stranded circular structure containing the first template strand inside protector strand(s) (e.g. inside the envelope, or loop), thereby inhibiting RCA of the first template strand, and wherein a second and/or further protector strand further comprises at least a first single-stranded region which comprises the target binding site (more particularly at least an accessible part of the target binding site) which allows the probe to bind to a complementary binding site in the target nucleic acid molecule, and a second or further protector strand (which may be the same or different) also comprises a second single-stranded region which comprises at least an accessible part of the binding site for the separate activator molecule, such that upon binding of the probe to the target nucleic acid molecule the probe is able to undergo a strand displacement reaction mediated by the separate activator molecule when bound to the target molecule, to allow RCA of the first template strand.

A probe of the invention, whether activatable by the target molecule or by a separate activator molecule, but particularly where it is activatable by the target, may comprise a primer, or more particularly a primer sequence, for the RCA reaction. Thus, the primer sequence may be a region, or stretch of nucleotides, in the second protector strand which is either hybridised, or capable of hybridising, to the first circular template strand, and which is able to prime a RCA reaction when the probe is activated. Thus in some embodiments the primer sequence may lie at the 3' end of a protector strand (e.g. of the second protector strand) and may be capable of being extended by a polymerase enzyme when it becomes hybridised to the first circular template strand, which occurs upon activation of the probe. This is depicted in the embodiments shown in FIGS. 3 and 4, 14, 18, 20, 21, 22, 25 and 26. In other embodiments the primer sequence may already be hybridised to the first circular template strand in the double-stranded circular structure of the probe, but may be unable to prime RCA until the probe is activated—for example the probe sequence may not have a hybridised 3' end available for extension until the probe is activated. This is depicted, for example in FIGS. 1 and 2. In such an embodiment, following activation of the probe, the 3' end of a protector strand (e.g. of the second protector strand) is released by the strand displacement, allowing it to be cleaved to leave a 3' end (which contains the primer sequence) hybridised to the first circular template strand and available for extension in a RCA reaction. This is described in more detail below.

In certain embodiments, at least a part of the activator binding site in a protector strand (e.g. in the second protector strand) (the target binding site, or, where present, the binding site for the separate activator molecule) is hybridised to the first circular template strand. In other words, at least a part of the first circular template strand is hybridised to the activator binding site in a protector strand (e.g. in the second protector strand). Binding of the activator for the RCA reaction (either the target nucleic acid molecule or a separate activator molecule) to the activator binding site may thus displace part of the first circular template strand from the activator binding site via strand displacement. Put another way, in certain embodiments the strand displacement reaction displaces part of a (e.g. the second) protector strand from the double-stranded circular structure, thereby exposing a part of the first circular template strand to allow binding of a primer for the RCA reaction. This is depicted in the embodiment shown in FIGS. 3 and 4 where the target is the activator, and in FIGS. 23, 25 and 26 where the activator is a separate activator molecule.

In a particular embodiment, wherein the strand displacement reaction displaces part of a (e.g. the second) protector strand from the double-stranded circular structure and exposes a part of the first circular template strand to allow binding of a primer for the RCA reaction, the probe may comprise within the 3' end region of a (e.g. the second) protector strand a sequence that is complementary to a sequence within the first circular template strand, in particular to the part of the first circular template strand that is exposed following the strand displacement reaction (i.e. a sequence that is homologous to a portion of the a protector strand hybridised to the first circular template strand (e.g. to a portion of the loop of a second protector strand), preferably to a portion of the activator binding site), and that is capable of acting as a primer for RCA of the template strand. Thus, in such an embodiment, the 3' end of a (e.g. the second) protector strand may bind to the first circular template strand following probe activation, thereby to serve as a primer for RCA. Put another way, the 3' end region of a (e.g. the second) protector strand may comprise the RCA primer.

A first single-stranded region of the nucleic acid probe (i.e. which is or comprises at least an accessible portion of the target binding site) may in particular embodiments be situated at an end of a (e.g. the second) protector strand. A first single-stranded region may thus be situated at the 5' end or at the 3' end of a (e.g. the second) protector strand. In an alternative embodiment, the first single-stranded region may be situated at an intermediate position within a (e.g. the second) protector strand.

In certain embodiments, wherein the activator for the RCA reaction (the activator for the probe) is a separate activator molecule and wherein the nucleic acid probe comprises a second single-stranded region which comprises at least an accessible part of the activator binding site, the second single-stranded region may be situated at an end of a (e.g. the second) protector strand. The second single-stranded region may thus be situated at the 5' end or at the 3' end of a (e.g. the second) protector strand. In an alternative embodiment, the second single-stranded region may be situated at an intermediate position within a (e.g. the second) protector strand.

In certain embodiments, wherein the probe comprises a second single-stranded region, first and second single-stranded regions may be separated spatially. In other words, the first and second single-stranded regions of a (e.g. the second) protector strand may be situated at different positions. Thus, first and second single-stranded regions may be situated at different ends (or differently expressed, in different end regions) of a (e.g. the second) protector strand, e.g. a first single-stranded region may be situated in the 3' end region and the second single-stranded region may be situated in the 5' end region of a (e.g. the second) protector strand, or a first single-stranded region may be situated in the 5' end region and the second single-stranded region may be situated in the 3' end region of a (e.g. the second) protector strand. However, in further embodiments a first single-stranded region may be situated in the 3' end region or the 5' end region and the second single-stranded region may be situated at an intermediate position (i.e. an intermediate region) within a (e.g. the second) protector strand, or the first single-stranded region may be situated in an intermediate region within the second protector strand, and the second single-stranded region may be situated in the 3' end region or the 5' end region of a (e.g. the second) protector strand. In yet another embodiment, both the first and second single-stranded regions may be situated in (separate) intermediate regions within a (e.g. the second) protector strand.

As previously mentioned, first and second single-stranded regions may alternatively be situated within different protector strands. For example, a first single-stranded region may be situated within one (e.g. the second) protector strand (i.e. at the 5' or 3' end, or an intermediate position thereof), and the second single-stranded region may be situated within another (i.e. a further) protector strand (i.e. at the 5' or 3' end, or an intermediate position thereof).

In certain embodiments, as noted above, the nucleic acid probe may provide the primer capable of acting as or providing the primer for RCA of the template strand once the probe has been activated.

As already discussed, in certain embodiments the probe may comprise in the 3' end region of a (e.g. the second) protector strand a sequence capable of binding to the template strand following displacement of second protector strand therefrom, thereby providing a primer for rolling circle amplification.

In an alternative embodiment, however, a (e.g. the second) protector strand may comprise a sequence in an intermediate region thereof, from which a primer capable of acting as a primer for RCA may be generated (i.e. a sequence capable of binding to the template strand from which a free 3' end capable of priming RCA may be generated) following activation of the probe. In certain embodiments, the sequence may be within the loop structure of the second protector strand (where one second protector strand is provided), or within the envelope structure of a second protector strand (where two or more second protector strands are provided), or in other words it may be within the double-stranded circular structure of the nucleic acid probe.

A protector strand (e.g. the second protector strand) may therefore comprise a primer sequence in the 3' end region thereof or in an intermediate region thereof, which is capable of acting as or providing a primer for RCA of the template strand once the probe has been activated (or, in other words, when the probe has bound to the target molecule, and optionally to the separate activator molecule, if used).

In certain embodiments, wherein a second protector strand comprises a primer sequence in an intermediate region thereof, the primer may be generated through cleavage (e.g. degradation) of the (e.g. second) protector strand in an activation-dependent manner. The cleavage may conveniently be, or comprise, enzymatic cleavage. Activation of the probe by strand displacement may therefore comprise the probe undergoing a conformational change which results in the generation of a substrate suitable for enzymatic cleavage. In one embodiment, cleavage may be 3' exonuclease degradation of the 3' end of the protector strand following the strand displacement reaction by a component having 3' exonuclease activity. In such an embodiment, the component having 3' exonuclease activity will degrade any single-stranded nucleic acid sequence present within the nucleic acid probe having a free 3' end following activation of the probe, and thus will degrade the 3' end region of a (e.g. the second) protector strand back to the point at which it is hybridised to the first circular template strand. In such a case, degradation of the 3' end of a (e.g. the second) protector strand of the probe will provide a primer to allow RCA of the first template strand. In other embodiments, the primer may be generated through restriction enzyme cleavage or by nickase cleavage.

The nucleic acid probe as defined herein may, in certain embodiments (where the probe comprises a single protector strand), comprise a second protector strand which comprises 5' and 3' end regions (i.e. regions which do not form part of the double-stranded circular structure comprising the loop of the second protector strand) which comprise mutually complementary regions, which are hybridised to each other to form a partially double stranded stem region comprising a duplex between the mutually complementary regions in the 5' and 3' end regions.

The nucleic acid probe may therefore in certain embodiments form a stem loop structure comprising a loop which is complementary to the first template strand and is hybridised thereto to form a double-stranded circular structure containing the first template strand inside the loop, and a partially double-stranded stem region comprising a duplex between the mutually complementary regions in the 5' and 3' end regions, and at least the first single-stranded region. In such embodiments, the strand displacement reaction which occurs upon binding of the probe to the target (and optionally to the separate activator molecule) results in at least partial opening of the stem of the stem-loop structure. In some embodiments there is also at least partial opening of the loop (i.e. the double stranded circular structure comprising the loop).

In certain other embodiments (where the probe comprises two or more (i.e. second and further) protector strands), the nucleic acid probe may comprise protector strands which comprise 5' and 3' end regions (i.e. regions which do not form part of the double-stranded circular structure) which comprise complementary regions to end regions of another protector strand, and which hybridise thereto to form partially double-stranded stem structures, i.e. stem regions comprising a duplex between the 5' and 3' end regions of the respective protector strands. For example the probe may comprise second and third protector strands, as depicted for Example in FIGS. 21 and 26, wherein stem structures (which may be partially double stranded) are formed between the 5' and 3' end regions of the two respective strands. Thus, the probe may be seen to comprise a double-stranded circle structure comprising portions of the second protector strands complementary to the first template strand (i.e. the "protecting regions" or envelope) and one or more stem regions (comprising duplexes formed between complementary regions in the 5' and 3' end regions of separate second protector strands). The stem regions may be partially double stranded. In particular, at least one such stem region is partially double-stranded and comprises a first and/or second single-stranded region.

In such embodiments, the strand displacement reaction which occurs upon binding of the probe to the target (and optionally to the separate activator molecule) results in at least partial opening of the region of duplex of a stem region (i.e. of a stem arm structure), analogously to opening the stem region of a stem-loop structure. In such embodiments, at least partial opening of the envelope (double-stranded circular structure) may also occur, analogously to opening the loop region of a stem loop structure.

It will further be noted from FIGS. 21 and 26 that a 3' end region of one of the protector strands may comprise, or provide, the primer for RCA. In particular, the primer may be provided by the protector strand which does not comprise the first single-stranded region (comprising the target binding site; see e.g. FIG. 21) or which does not comprise the first and second single-stranded regions (comprising the target binding site and binding site for the separate activator molecule respectively; see e.g. FIG. 26). In one particular embodiment, the probe comprises a second protector strand which comprises the first single-stranded region, and optionally the second single-stranded region (where present) and a third protector strand. Preferably, the third protector strand comprises a third single-stranded region which comprises or provides a primer for RCA.

It will be understood from this that the term "end region" does not necessarily imply that the end region lies at the very 5' most or very 3' most end of the strand, and includes any region which is outside (i.e. at an end of) the double-stranded circular structure, and towards the 3' end or 5' end of the second or further protector strand. By corollary, an intermediate region of the second or further protector strand is a region which is in between the 5' and 3' end regions. An intermediate region thus lies in the part of the second or further protector strand which provides, or constitutes, the loop or which contributes to the envelope, in the double-stranded circular structure, i.e. the part of the second or further protector strand which is hybridised to the first circular template strand.

In particular, the mutually complementary regions which form the duplex in the partially double-stranded stem region of the stem or stem-loop structure need not lie at the very 5' and/or 3' end of the second protector strand or further protector strand(s). Indeed, as noted above and discussed further below, the first and/or second single-stranded regions may lie at the 5' and/or 3' ends of the second protector strand or further protector strand(s), and hence of the stem region. Thus the duplex of the stem region may comprise one or two single-stranded "extensions", which may constitute, or comprise, first and/or second single-stranded regions, or the primer for RCA (e.g. as a third single-stranded region). This is depicted for example in FIGS. 3 and 4, 19, and 22. Accordingly, a first and/or the second single stranded region may lie in the 5' end region 5' to the duplex, and/or in the 3' end region 3' to the duplex. In particular, (but not necessarily) they may lie at the 5' and/or 3' ends. In certain embodiments, described further below (e.g. where the probe is provided as part of a proximity probe, as depicted in FIG. 14) there may be a further region (or sequence) lying at the end of single-stranded region (for example a capture or immobilisation sequence, e.g. a sequence which is complementary to an oligonucleotide attached to an antibody or other binding molecule, which allows the probe to hybridise to the oligonucleotide to form an affinity binding probe (e.g. a proximity probe) for a target analyte which is not a nucleic acid molecule).

The 5' end region of a (e.g. the second) protector strand provides the 5' strand of the duplex (i.e. the duplex of a stem), and the 3' end region provides the 3' strand of the duplex. The 5' and/or 3' end regions (i.e. the 5' and/or 3' strands of the duplex) may comprise further or additional single-stranded regions i.e. additional sequences within the 5' and/or 3' end regions which do not hybridise to a complementary sequence in the opposite strand (e.g. sequences within the 5' and/or 3' strands of the duplex and/or 5' to the 5' strand of the duplex and/or 3' to the 3' strand of the duplex).

A first, and if present, the second single-stranded regions of the probe may thus be situated within or at the end of one or other of the strands of the duplex of the stem region. A first single-stranded region and, if present, the second single-stranded region may thus be provided as single-stranded (i.e. unpaired regions) within the partially double-stranded stem region. Thus the partially double-stranded stem region may, in certain embodiments, comprise a duplex between the mutually complementary regions in the 5' and 3' end regions (or complementary regions in the 5' and 3' end regions of two (e.g. second and third) protector strands), and may further comprise first and/or second single-stranded regions. The single stranded region or regions may be situated at an end of one of the strands of the duplex, or may be situated within one of the strands of the duplex as an unpaired and accessible "bulge" region (that is an unpaired single-stranded region within a strand of the duplex, or a loop-type or blister structure). This is depicted in FIGS. 1 and 2. In a particular embodiment, the probe comprises a first and second single-stranded region, wherein the first single-stranded region is situated at the end of one of the strands of the duplex, and the second single-stranded region is situated within one of the strands of the duplex as a bulge (an unpaired loop). Alternatively, the first single-stranded region is situated within one of the strands of the duplex as a bulge (an unpaired loop) and the second single-stranded region is situated at the end of one of the strands of the duplex.

Where the probe contains a partially double-stranded stem region, the target binding site (or optionally sites) may be situated at least partially within the 5' or 3' end region of a (e.g. the second protector) strand, and thus within the partially double-stranded stem region. Analogously, where a separate activator molecule is required for activation of the nucleic acid probe, the binding site for the separate activator molecule may be situated at least partially within the 5' or 3' end region of a (e.g. the second) protector strand, and thus within the partially double-stranded stem region. The target binding site (or, where present, the binding site for the separate activator molecule) may thus be at least partially hybridised to a complementary sequence within the probe (a sequence from the opposite strand of the duplex, and, in certain embodiments, a sequence from the first circular template strand).

As hereinbefore described, binding of the target nucleic acid molecule, or, where present, the separate activator molecule (i.e. the activator for the RCA reaction) to the nucleic acid probe results in a strand displacement reaction. In embodiments wherein the probe comprises a stem loop structure, following binding of the activator for the RCA reaction to the accessible part of the binding site in a single-stranded region (the first or second single-stranded region), the activator displaces the nucleotide sequence hybridised to the (inaccessible part(s) of the) activator binding site (the target binding site, or where present, the binding site for the separate activator molecule) and causes the stem region duplex to at least partially open. Binding of the target nucleic acid molecule or separate activator molecule may further result in the at least partial opening of the loop (i.e. the at least partial displacement of a (e.g. the second) protector strand from the first circular template strand). Such displacement(s) activate the probe, allowing initiation of an RCA reaction.

As described above, a single-stranded region (the first, or if present, the second, single-stranded region), may be situated within a bulge in a strand in the stem region duplex. In a particular embodiment, the first accessible domain of an activator (target or separate activator molecule) binding site is situated within a bulge. The single-stranded region (i.e. the bulge) may be situated in the 5' or in the 3' strand of the double-stranded region. The activator binding site may further comprise second and third domains, which are situated in the duplex of the stem region, either side of the bulge, and are hybridised to complementary sequences within the opposite strand of the duplex. In such an embodiment, binding of the activator to the first domain of the binding site is followed by binding of the activator to the second and third domains of the binding site, which binding displaces the sequences hybridised thereto and opens at least the stem of the stem loop structure.

In a preferred embodiment, as depicted in FIGS. 1 and 2, the first single-stranded region is situated within the bulge, and the bulge (and thus the target binding site) is situated within the 5' end region of a (e.g. the second) protector strand (the 5' strand of the duplex). In such an embodiment, binding of the target nucleic acid molecule to the target binding site via the first single-stranded region situated within the bulge opens at least the stem of the stem loop structure and releases the 3' end region of a (e.g. the second) protector strand. In other words, the 3' end region of a (e.g. the) second protector strand is displaced from its complementary sequence in the 5' end region of a (e.g. the second) protector strand (i.e. either of the same protector strand, or of another protector strand), and is thus rendered single-stranded following unfolding of the duplex. This may render the 3' end of the (e.g. second) protector strand susceptible to cleavage (e.g. 3' exonuclease cleavage), wherein the 3' end of the strand is cleaved (e.g. degraded) to provide a primer for RCA of the first template strand.

Thus, in one embodiment, the present invention provides a nucleic acid probe for detection of a target nucleic acid molecule, wherein said probe is activatable by the target nucleic acid molecule to undergo a RCA reaction, said probe comprising:
  (i) a first circular template strand which is capable of acting as a template for RCA; and
  (ii) a second protector strand which protects the first strand from RCA in the absence of the target nucleic acid molecule, and which comprises (a) a target binding site in the 5' end region thereof, the target binding site comprising first, second and third domains, and (b) a primer sequence in an intermediate region thereof which lies between the 5' and 3' end regions, which primer sequence is capable of providing a primer for RCA of the first circular template strand when the probe has bound to the target nucleic acid molecule;
wherein the 5' and 3' end regions of the second protector strand comprise mutually complementary regions which are hybridised to each other to form a stem-loop structure comprising a loop which is complementary to the first template strand and is hybridised thereto to form a double-stranded circular structure containing the first template strand inside the loop, and a partially double stranded stem region comprising a duplex between the mutually complementary regions, said duplex comprising a (first) single stranded region in a bulge in the 5' strand of the duplex (i.e. the strand comprising the 5' end region), and wherein the first domain of the target binding site lies in the (first) single stranded region of the bulge and is thereby accessible for binding by the target nucleic acid molecule, allowing the probe to bind to a complementary binding site in the target nucleic acid molecule, and wherein the second and third domains lie at either side of the bulge and are hybridised to complementary sequences within the 3' strand of the duplex structure (i.e. the strand comprising the 3' end region), such that when the target nucleic acid molecule binds to the first domain of the target binding site in the probe, it displaces the sequences hybridised to the second and third domains of the target binding site and causes the duplex to open, releasing the 3' end region of the second protector strand, rendering it susceptible to cleavage to generate a primer for RCA of the first circular template strand.

In a further embodiment, the present invention provides a nucleic acid probe for detection of a target nucleic acid molecule, wherein said probe is activatable by the target nucleic acid molecule to undergo a RCA reaction, said probe comprising:
  (i) a first circular template strand which is capable of acting as a template for RCA; and
  (ii) two or more protector strands which protect the first strand from RCA in the absence of the target nucleic acid molecule, wherein one of the protector strands comprises a target binding site in the 5' end thereof, the target binding site comprising first, second and third domains, and another of the protector strands comprises a primer sequence in an intermediate position thereof which lies between the 5' and 3' end regions thereof, which primer sequence is capable of providing a primer for RCA of the first circular template strand when the probe has bound to the target nuclei acid molecule;
wherein the two or more protector strands form an envelope that is complementary to the first template strand and is hybridised thereto to form a double-stranded circular structure containing the first template strand inside it, wherein the 5' and 3' end regions of the two or more protector strands comprise regions of complementarity to another protector strand and are hybridised to each other to form two or more stem regions comprising a duplex between the complementary regions, wherein one said duplex comprises a (first) single stranded region in a bulge in the 5' strand of the duplex (i.e. the strand comprising the 5' end region comprising the target binding site), and wherein the first domain of the target binding site lies in the (first) single stranded region of the bulge and is thereby accessible for binding by the target nucleic acid molecule, allowing the probe to bind to a complementary binding site in the target nucleic acid molecule, and wherein the second and third domains lie at either side of the bulge and are hybridised to complementary sequences within the 3' strand of the duplex (i.e. the strand comprising the 3' end region of another protector strand), such that when the target nucleic acid molecule binds to the first domain of the target binding site in the probe, it displaces the sequences hybridised to the second and third domains of the target binding site and causes the duplex to open, releasing the 3' end region of the other protector strand, rendering it susceptible to cleavage to generate a primer for RCA of the first circular template strand.

In particular, the 3' end region may be removed by cleavage, leaving an intermediate region of the second protector strand hybridised to the first circular template strand having a hybridised 3' end which may be extended in a RCA reaction.

In other embodiments in which the probe comprises a partially double-stranded stem region, the single stranded region (the first or if present, the second, single-stranded region) may be situated at an end of a strand in the duplex. The single-stranded region may thus be situated at the 5' end or the 3' end of a (e.g. the second) protector strand, and thus at the 5' or 3' end of the duplex structure. In a particular embodiment, the single-stranded region is a portion (e.g. a first accessible domain) of the target binding site, and is situated at the 5' end of a (e.g. the second) protector strand. In a further particular embodiment, the single-stranded region is a portion (e.g. a first accessible domain) of a binding site for a separate activator molecule and is situated at the 3' end of a (e.g. the second) protector strand.

In embodiments such as these, the single-stranded region (i.e. comprising or constituting a binding site for the target nucleic acid molecule or for the separate activator molecule) may be seen to represent a first domain of the activator binding site. The activator binding site further comprises a second and third domain, wherein the second domain is situated within the stem of the duplex structure (i.e. adjacent to the first domain and within the duplex structure) and is hybridised to a complementary sequence within the opposite strand of the duplex structure, and the third domain is situated at least partially within the loop region of the second protector strand and is hybridised to a complementary sequence within the first circular template strand. In these embodiments, binding of the activator to the first domain of the activator binding site (the single-stranded region, being a first single-stranded region or a second single-stranded region as defined herein) is followed by binding of the activator to the second and third domains of the activator binding site, which binding displaces the sequences hybridised to the activator binding site and causes the duplex to open, and a (e.g. the second) protector strand to dissociate at least partially from the first circular template strand, exposing a single-stranded region of the first circular template strand. A primer for RCA may bind to said single-stranded region, thereby allowing the initiation of RCA. In one embodiment, the primer is provided from the 3' end of a protector strand (e.g. the second protector strand, if there is one protector strand, or a third protector strand if there are two protector strands etc.). In another embodiment, the primer is provided from the 3' end of the separate activator molecule.

Thus, in one other embodiment, as depicted in FIGS. 3 and 4, the present invention provides a nucleic acid probe for detection of a target nucleic acid molecule, wherein said probe is activatable by the target nucleic acid molecule to undergo a RCA reaction, said probe comprising:
 (i) a first circular template strand which is capable of acting as a template for RCA; and
 (ii) a second protector strand which protects the first strand from RCA in the absence of the target nucleic acid molecule, and which comprises (a) at least an accessible part (i.e. domain) of a target binding site in the 5' end region thereof, the target binding site comprising first, second and third domains, and (b) a primer sequence at the 3' end thereof (more particularly at the 3' end of the 3' end region thereof), which primer sequence is complementary to a sequence within the first circular template strand and is thereby capable of providing a primer for RCA of the first circular template strand when the probe has bound to the target nucleic acid molecule;
wherein the 5' and 3' end regions of the second protector strand comprise mutually complementary regions which are hybridised to each other to form a stem-loop structure comprising a loop which is complementary to the first template strand and is hybridised thereto to form a double-stranded circular structure containing the first template strand inside the loop, and a partially double-stranded stem region comprising a duplex between the mutually complementary regions, and wherein the first domain of the target binding site lies in a single-stranded region situated at the end of the 5' strand of the duplex (i.e. the strand comprising the 5' end region) and is thereby accessible for binding by the target nucleic acid molecule, allowing the probe to bind to a complementary binding site in the target nucleic acid molecule, the second domain is hybridised to a complementary sequence within the 3' strand of the duplex (i.e. the strand comprising the 3' end region), and the third domain is situated at least partially within the loop region of the second protector strand and is hybridised to a complementary sequence within the first template strand, such that when the target nucleic acid molecule binds to the first domain of the target binding site in the probe, it displaces the sequences hybridised to the second and third domains of the target binding site and causes the duplex to open and the second protector strand at least partially to dissociate from the first circular template strand, allowing the 3' end of the second protector strand to bind to its complementary sequence within the first circular template strand thereby to provide a primer for RCA of the first template strand.

In another embodiment, the present invention also provides a nucleic acid probe for detection of a target nucleic acid molecule, wherein said probe is activatable by the target nucleic acid molecule to undergo a RCA reaction, said probe comprising:
 (i) a first circular template strand which is capable of acting as a template for RCA; and
 (ii) two or more (e.g. second and third, and optionally subsequent) protector strands which protect the first strand from RCA in the absence of the target nucleic acid molecule, wherein one of the protector strands (e.g. the second protector strand) comprises at least an accessible part (i.e. domain) of a target binding site in the 5' end region thereof, the target binding site comprising first, second and third domains, and another protector strand (e.g. the third protector strand) comprises a primer sequence at the 3' end thereof (more particularly at the 3' end of the 3' end region thereof), which primer sequence is complementary to a sequence within the first circular template strand and is thereby capable of providing a primer for RCA of the first circular template strand when the probe has bound to the target nucleic acid molecule;
wherein the two or more protector strands form an envelope that is complementary to the first template strand and is hybridised thereto to form a double-stranded circular structure containing the first template strand inside the envelope, and wherein the 5' and 3' end regions of the two or more protector strands comprise regions of complementarity to another protector strand and are hybridised to each other to form two or more stem regions comprising a duplex between the complementary regions, wherein at least one of said stem regions is partially double stranded and wherein the first domain of the target binding site lies in the single-stranded region of said stem region, situated at the end of the 5' strand of said duplex (i.e. the strand comprising the 5' end region), and is thereby accessible for binding by the target nucleic acid molecule, allowing the probe to bind to a complementary binding site in the target nucleic acid molecule, the second domain is hybridised to a complementary sequence within the 3' strand of the duplex (i.e. the strand comprising the 3' end region of another protector strand), and the third domain is situated at least partially within the envelope region of the protector strand and is hybridised to a complementary sequence within the first template strand, such that when the target nucleic acid molecule binds to the first domain of the target binding site in the probe, it displaces the sequences hybridised to the second and third domains of the target binding site and causes the duplex to open and the protector strand to at least partially dissociate from the first circular template strand, allowing the 3' end of the other protector strand to bind to its complementary sequence within the first circular template strand thereby to provide a primer for RCA of the first template strand.

In a further embodiment, as depicted in FIG. 23, the present invention provides a nucleic acid probe for detection of a target nucleic acid molecule, wherein in the presence of the target nucleic acid molecule said probe is activatable by a separate activator molecule, which also binds to the target nucleic acid molecule, to undergo a RCA reaction, said probe comprising:
 (i) a first circular template strand which is capable of acting as a template for RCA; and
 (ii) a second protector strand which protects the first strand from RCA in the absence of the target nucleic acid molecule, and which comprises a target binding site in the 5' end region thereof and at least an accessible part (i.e. domain) of the binding site for the separate activator molecule in the 3' end region thereof, said separate activator binding site comprising first, second and third domains;

wherein the 5' and 3' end regions of the second protector strand comprise mutually complementary regions which are hybridised to each other to form a stem loop structure comprising a loop which is complementary to the first template strand and is hybridised thereto to form a double-stranded circular structure containing the first template strand inside the loop, and a partially double-stranded stem region comprising a duplex between the mutually complementary regions and first and second single-stranded regions at the end of the 5' and 3' strands of the duplex (i.e. the strands comprising the 5' and 3' end regions) respectively comprising the target binding site and the first domain of the separate activator binding site, wherein the target binding site and the first domain of the separate activator binding site are thereby accessible for binding, allowing the probe to bind to a complementary binding site in the target nucleic acid molecule and at the same time (simultaneously or sequentially), to a complementary binding site in a separate activator molecule (more particularly, when the separate activator molecule is bound to the target molecule and thereby brought into proximity to the probe), and wherein the second domain is hybridised to a complementary sequence within the 5' strand of the duplex, and the third domain is situated within the loop region of the second protector strand and is hybridised to a complementary sequence within the first template strand, such that upon binding of the probe to the target molecule the probe and the separate activator molecule are brought into proximity and the binding of the separate activator molecule to the first domain displaces the sequences hybridised to the second and third domains of the separate activator binding site and causes the duplex to open and the second protector strand at least partially to dissociate from the first circular template strand, allowing the 3' end of the separate activator molecule to bind to the first template strand to provide a primer for RCA of the first template strand.

As is clear from the above descriptions, where the probe comprises a stem-loop structure, the ends of the probe may be hybridised to one another, i.e. the duplex region may extend to the ends of the probe. However, in other embodiments, the 3' end, the 5' end, or both the 3' and 5' ends of the probe may be single-stranded, i.e. the ends of the duplex structure may be single-stranded and hence not complementary to one another or capable of hybridisation to one another.

In certain other embodiments, however, the nucleic acid probe does not comprise a partially double-stranded stem region, and instead comprises a double-stranded circular structure, a single-stranded 5' end region and a single-stranded 3' end region. (In certain other embodiments, however, the probe may comprise only a single single-stranded region (i.e. a single-stranded 5' end region or a single-stranded 3' end region.) In one embodiment, the 5' single-stranded end region of the second protector strand comprises an accessible part of the target binding site, and the single-stranded 3' end region of the second protector strand comprises a primer for the RCA reaction. This is depicted in FIG. 20. However, in a further embodiment, the 3' single-stranded end region of the second protector strand may comprise an accessible part of the target binding site (the primer for the RCA reaction may be provided separately or from another molecule (e.g. the target nucleic acid molecule) present in the sample). In further embodiments of such a version of the probe which does not comprise a stem structure, one single-stranded end region (e.g. the 5' end region) may comprise a target binding site and the other single-stranded end region (e.g. the 3' end region) may comprise an accessible part of a binding site for a separate activator molecule. By analogy with the descriptions given above, the other part of the target or (where present) separate activator binding site lies in the loop of the double-stranded circular structure and is hybridised to the first circular template strand, such that it may be displaced from the double-stranded circular structure upon binding of the target or separate activator molecule to the accessible part of the binding site.

In one particular embodiment, as depicted in FIG. 20, the present invention provides a nucleic acid probe for detection of a target nucleic acid molecule, wherein said probe is activatable by the target nucleic acid molecule to undergo a RCA reaction, said probe comprising:
  (i) a first circular template strand which is capable of acting as a template for RCA; and
  (ii) a second protector strand which protects the first strand from RCA in the absence of the target nucleic acid molecule, and which comprises a target binding site and a primer sequence at the 3' end thereof which is complementary to a sequence in the first circular template strand (and therefore capable of acting as primer for RCA of the first circular template strand when the probe has bound to the target nucleic acid molecule);
wherein the second protector strand forms a loop which is complementary to the first template strand and is hybridised thereto to form a double-stranded circular structure containing the first template strand inside the loop, thereby inhibiting RCA of the first template strand, and wherein the second protector strand further comprises a single-stranded 3' end region comprising the primer sequence a single-stranded region 5' end region which comprises at least an accessible part of the target binding site which allows the probe to bind to a complementary binding site in the target nucleic acid molecule, such that upon binding of the probe to the target nucleic acid molecule the probe is able to undergo a strand displacement reaction mediated by the target nucleic acid molecule, which displaces part of the second protector strand from the double-stranded circular structure, thereby exposing a part of the first circular template strand which comprises a sequence which is complementary to the single-stranded 3' end of the second protector strand, allowing it to bind to the first template strand to provide a primer for RCA of the first template strand.

Analogously to the above, two or more second protector strands may similarly bind to (and protect) a first circular template strand, and not comprise regions of complementarity at their 5' and/or 3' ends.

Production of the nucleic acid probes of the present invention typically comprises contacting a linear first nucleic acid molecule (which will serve as the first circular template strand of the probe) with a linear second nucleic acid molecule (which will serve as the second protector strand) which comprises a region of complementarity (the loop region) to the first template strand and may hybridise thereto to bring the 5' and 3' ends of the first nucleic acid molecule into direct juxtaposition for ligation. Addition of a ligase molecule (e.g. T4 ligase) may circularise the first template strand, thereby forming a probe of the invention comprising a double-stranded circular structure.

However, in certain embodiments, during the production of a nucleic acid probe, the 5' and 3' ends of two or more first nucleic acid molecules may be brought into direct juxtaposition for ligation, templated by two or more second nucleic acid molecules. In particular, a first first nucleic acid molecule may hybridise to a first second nucleic acid molecule via its 5' end and to a second second nucleic acid molecule via its 3' end, and a second first nucleic acid molecule may hybridise to a first second nucleic acid molecule via its 3' end and to a second second nucleic acid molecule via its 5' end. Intermolecular (rather than intramolecular) ligation of the at least two first nucleic acid molecules may result in the formation of a multimeric nucleic acid probe comprising a circular nucleic acid molecule comprising at least two first nucleic acid molecules, and at least two second protector strands hybridised thereto, which strands protect the circular nucleic acid molecule from RCA in the absence of the target nucleic acid molecule (i.e. they form an envelope which is complementary to the first template strand and is hybridised thereto to form a double-stranded circular structure). Thus although typically the probe will be in monomeric form comprising one first circular template strand and one second protector strand, it may be provided in multimeric (e.g. oligomeric) form, comprising two or more first circular template strand which are ligated together into a circle (an enlarged circle) and two or more protector strands. This is depicted in FIG. 6.

The above process may occur particularly wherein the probe comprises a stem-loop structure (i.e. in particular wherein the 5' and 3' end regions of the probe are complementary and capable of forming a duplex structure), as two (or more) second nucleic acid molecules may be capable of interacting via their respective 5' and 3' ends to form intermolecular, rather than intramolecular, duplex structures, resulting in a nucleic acid multimer. Said multimer will comprise the loop region of the second nucleic acid strand between said duplex structures, and will thus contain "n" loop regions, where "n" is the number of second nucleic acid molecules present in said multimer. In such an event, the 5' and 3' ends of two (or more) first nucleic acid molecules may be brought into juxtaposition for ligation, templated by the multimer structure formed by the interaction of the 5' and 3' ends of the (at least) two second nucleic acid molecules. Addition of a ligase molecule will, in these embodiments, result in the formation of a multimeric circular strand comprising "n" first nucleic acid molecules.

Thus, the present invention further provides a multimeric nucleic acid probe, comprising a multimeric first circular template strand comprising at least two first template strands, and at least two second protector strands which protect the multimeric first template strand from RCA in the absence of the target nucleic acid molecule. Said multimeric nucleic acid probe will be activatable in the presence of the target nucleic acid molecule in an analogous way to the probes described above.

In a further embodiment, as depicted in FIG. 25, the present invention provides a nucleic acid probe for detection of a target nucleic acid molecule, wherein in the presence of the target nucleic acid molecule said probe is activatable by a separate activator molecule to undergo a RCA reaction, said probe comprising:
  (i) a first circular template strand which is capable of acting as a template for RCA; and
  (ii) a second protector strand which protects the first strand from RCA in the absence of the target nucleic acid molecule, and which comprises (a) in the 5' end region thereof the target binding site and a binding site for the separate activator molecule, said target binding site and said separate activator binding site each comprising first, second and third domains, the first domain of the target binding site being accessible for binding by the target molecule, thereby allowing the probe to bind to a complementary site in the target molecule and
  (b) in the 3' end region thereof a primer domain capable of hybridising to the first template strand to prime RCA thereof;
wherein the 5' and 3' end regions of the second protector strand comprise mutually complementary regions which are hybridised to each other to form a first stem-loop structure comprising a first loop which is complementary to the first template strand and is hybridised thereto to form a double-stranded circular structure containing the first template strand inside the first loop, and a partially double-stranded stem region comprising (i) a first duplex between the mutually complementary regions, (ii) a 5' end region comprising a first single-stranded region which contains the accessible first domain of the target binding site at the end of the 5' strand of the first duplex and a second stem-loop structure comprising a second loop and a second duplex, and (iii) a single-stranded 3' end region comprising the primer domain at the end of the 3' strand of the first duplex; and wherein the second and third domains of the target binding site are contained in the second duplex and second loop respectively and the first, second and third domains of the separate activator binding site are contained in the second duplex, first duplex and first loop respectively, the second domain of the target binding site being complementary and hybridised to the first domain of the activator binding site within the second duplex, and the third domain of the activator binding site being hybridised to the first circular template strand;
such that upon binding of the first accessible domain of the target binding site to its complementary site in the target molecule, strand displacement by the target molecule causes the second duplex to open, to allow the respective complementary sites of the target molecule to bind to the second and third domains of the target binding site, and thereby rendering accessible the first domain of the separate activator binding site, whereupon binding of the separate activator molecule to the first domain of its binding site displaces the sequences hybridised to the second and third domains of the separate activator binding site and causes the first duplex to open and the second protector strand at least partially to dissociate from the first circular template strand, allowing the single-stranded 3' end of the second protector strand to bind to the first template strand to provide a primer for RCA of the first template strand.

Such a probe may be used together with a separate activator molecule which is also designed to bind to the target molecule, and which itself may be "activated" by target binding to interact with the probe. Thus, such a separate activator molecule may comprise at least an accessible part (domain) of a target binding site and a probe binding site which is at least partially contained within a metastable secondary structure (such as a hairpin, or stem-loop structure) and which is inaccessible for binding to the probe until the separate activator molecule has bound to the target molecule, and a target molecule-mediated strand displacement causes the metastable secondary structure to open to release, or render accessible, the probe binding site within the separate activator molecule. Binding of the separate activator molecule to the first domain of the separate activator binding site in the probe, then causes the probe to be activated by a strand displacement reaction by the separate activator molecule, as described above. Such a reaction is depicted in FIG. 25. This shows how the probe may be used in a method which requires dual recognition of the target molecule by both probe and separate activator molecule in a homogenous manner. Analogously to the situation shown in FIG. 23, binding of the probe and the separate activator molecule to the target molecule brings them into proximity and allows them to interact, or facilitates their interaction.

In particular, the separate activator molecule for use with such a probe may comprise single stranded 5' and 3' end regions, and an intermediate sequence therebetween comprising mutually complementary regions which hybridise together to form a stem-loop structure, wherein one of said single-stranded regions comprises an accessible domain of a target binding site, and the stem-loop structure comprises a further domain of the target binding site and at least one domain of a probe binding site. The other single-stranded region may comprise a further domain of the probe binding site. As depicted in FIG. 25, the 3' end region of the separate activator molecule comprises a first domain of the target binding site which is complementary to a cognate activator binding site (or domain thereof) in the target molecule; the duplex of the stem of the stem loop structure comprises a second domain of the target binding site hybridised to the second domain of the probe binding site (which is complementary to the second domain of the separate activator binding site of the probe); the loop of stem-loop structure comprises the first domain of the probe binding site (which is complementary to the first domain of the separate activator binding site of the probe); and the 5' end region comprises a third domain of the probe binding site (which is complementary to the third domain of the separate activator binding site in the probe).

"Complementary" nucleotide sequences will combine with specificity (hybridise) to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G and C of one sequence is then aligned with a T(U), A, C and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule.

In certain embodiments, it may be advantageous for two complementary sequences within the probe to not comprise an absolute (i.e. 100%) degree of complementarity. The interaction between the probe and the target nucleic acid or separate activator molecule is sufficient to displace a sequence within the probe (i.e. strand displacement) that is hybridised to the target binding site or binding site for the separate activator molecule, and thus preferably is a stronger interaction that the interaction between the two complementary sequences within the probe. Accordingly, complementary sequences within the probe may comprise one or more mismatches (unpaired bases) relative to one another, provided that in the absence of the target nucleic acid molecule or separate activator molecule the sequences are able to remain hybridised to each other.

The rate of amplification of a target sequence by RCA (i.e. the rate at which copies of the target sequence are generated) is dependent on the size of the template nucleic acid molecule used in the amplification reaction. For a polymerase enzyme of a given processivity rate, a larger nucleic acid template will be amplified more slowly (per unit time) than a smaller nucleic acid template. Thus, advantageously, a template for RCA will be of a size that allows copies of it to be generated (i.e. for it to be amplified) at an acceptable rate. Furthermore, a smaller template may be less likely to undergo non-target specific amplification.

Thus, although there is not an upper limit on the size of the circle, and in some embodiments the first circular template strand may be 100, 200, 300, 400 or 500 nucleotides or more in size (particularly when in multimeric form), the first circular template strand may preferably comprise up to 500 nucleotides, up to 400 nucleotides, up to 300 nucleotides, up to 200 nucleotides or up to 100 nucleotides, or more particularly, up to 90, 80, 70 or 60 nucleotides. However, RCA is known to be sterically hindered if the circular nucleic acid molecule is too small. Furthermore, double-stranded circular structures may have difficulty in forming (i.e. the second protectors strand may not be able to bind to the first template strand) if the first circular template strand is too small, due to the additional steric constrains imposed when a double-helical structure is formed upon binding of the second protector strand to the first circular template strand. Thus, the first circular template strand in certain embodiments comprises at least 20 nucleotides, at least 30 nucleotides, at least 40 nucleotides, at least 50 nucleotides, at least 60 nucleotides, at least 70 nucleotides, at least 80 nucleotides, or at least 90 nucleotides.

Surprisingly, it has been found that double-stranded circular nucleic acid molecules of a smaller size than was previously thought possible may be produced where the two strands contain one or more mismatches (i.e. one or more insertions, deletions or mismatches) relative to one-another. Without wishing to be bound by theory, it is believed that a mismatch may provide a 'hinge' region comprising a higher degree of flexibility and/or rotational freedom, and thus that this may relieve stress within the phosphodiester backbones of the nucleic acid molecules in the double-stranded structure. Accordingly, the first and second or further strands of the probe of the present invention may comprise one or more mismatches (insertions, deletions and/or substitutions) relative to one another, within the double-stranded circular structure (e.g. within the loop region, or the envelope region) of the probe. In other words the protecting regions of the second or further (subsequent) protector strands need not be 100% complementary and/or not all bases of the first template strand need be hybridised to a protecting region of a protector strand. It is believed that this may allow a smaller first circular template strand to be provided in the probes of the present invention.

Thus, in one embodiment, a second or further protector strand may contain one or more base insertions relative to the first template strand. In another embodiment, the first template strand may contain one or more base insertions relative to the second template strand. In a further embodiment, the one or more base insertions may be an adenosine (A) nucleotide. In yet another embodiment the first and second strands may comprise one or more base substitutions, i.e. bases which do not undergo canonical Watson-Crick base-pairing.

It is important to note, however, that where one or more mismatches is present between the first and second or subsequent strand, the second or further protector strand or strands must maintain a sufficient degree of homology to the first template strand to remain hybridised thereto. Furthermore, it is preferred that extended stretches (i.e. more than two or three nucleotides) of mismatch between the respective strands is avoided, as this may allow non-specific binding of an oligonucleotide present in the sample to the first template strand, which may initiate RCA in the absence of a target nucleotide. Thus, in certain embodiments the first and second strands do not contain a contiguous stretch of 4 or more, or more particularly 3 or more, mismatched bases, and preferably do not contain a contiguous stretch of 2 or more mismatched bases. Thus a mismatch may comprise 1 to 3 contiguous mismatched bases, more preferably 1 or 2 contiguous mismatched bases.

The length and nucleotide composition of the second or further protector strand(s)(or more particularly of the component parts thereof, e.g. the 5' end region(s), intermediate region(s), and 3' end region(s), and if present the duplex of a stem or the stem in a stem-loop structure), are not critical, subject to the constraints of providing appropriate binding sites for the target or separate activator molecule and complementary sequences for intramolecular (e.g. in a stem) or intramolecular (e.g. the intermediate sequence to the first template strand, the primer sequence to the first template strand etc.) hybridisation, as required. Such regions may therefore be designed in a routine manner according to principles known in the art and may be varied according to choice or need. Thus for example, an accessible part of a target or separate activator binding site (e.g. as provided as or in a first or second single-stranded region) may, for example, comprise 6 to 50 nucleotides (e.g. any one of 7, 8, 9 or 10 to any one of 20, 22, 25, 27, 30, 35, 40 or 45 nucleotides). A primer sequence may comprise 6 to 30 nucleotides, e.g. any one of 6, 7, 8, 9 or 10 to any one of 12, 14, 16, 18, 20, 22, 24 or 25 nucleotides. A duplex in a partially double-stranded stem region may comprise, for example 6 to 50 base pairs, e.g. any one of 7, 8, 9 or 10 to any one of 15, 20, 25, 30, 35, 40, or 45 base pairs. A duplex which comprises a single stranded region in a bulge in one of the strands may for example have shorter duplex regions either side of the bulge, than a single duplex in a stem region. A duplex in a stem region may comprise one or more mismatches, e.g. as discussed above, for example to aid or facilitate a strand displacement reaction.

The first circular template strand may comprise a reporter domain, which is a sequence that can be used to detect and/or identify the RCA product produced from the probe of the invention. This may be particularly advantageous in multiplex embodiments of the invention, i.e. where more than one analyte, e.g. nucleic acid analyte, is detected in a single assay. The RCA template provided by each probe (each probe is specific for a target analyte, as determined by the target binding domain, or, if present, the binding domain for the separate activator molecule), may comprise a unique "marker" or identification sequence (e.g. a bar-code sequence, such as a site comprising the sequence of a specific detection probe, i.e. the RCA product is complementary to the RCA template and as such detection probes that hybridise to the RCA product will comprise a sequence that is identical to part of the RCA template) to allow the separate detection and/or quantification of each analyte in the sample. Thus, in multiplex assays each probe may comprise a different reporter domain and the detection of the interaction of the probe and the target analyte, i.e. the detection of each analyte, may be detected in parallel (i.e. at the same time), e.g. using oligonucleotides tagged with distinct labels (e.g. fluorophores or sequence tags) that may hybridise to the complement of the reporter domain. Alternatively, each marker (and therefore each analyte) may be detected using sequential visualisation reactions, wherein each reaction is separated by, e.g. stripping or bleaching steps. Methods of sequential visualisation reactions suitable for using the methods of the invention are known in the art, e.g. Goransson et al., 2009 (A single molecule array for digital targeted molecular analyses. Nucleic Acids Res. 2009 January; 37(1):e7), Wahlby et al., 2002 (Sequential immunofluorescence staining and image analysis for detection of large numbers of antigens in individual cell nuclei. Cytometry, 47(1):32-41, 2002), which are hereby incorporated by reference. In some representative embodiments of the invention, multiple analytes may be detected in parallel. In other representative embodiments of the invention, multiple analytes may be detected sequentially. Combinatorial methods of labelling, e.g. ratio labelling, using different combinations and/or ratios of different labels are known in the art and may be used to increase the number of different molecules, and hence different analytes which may detected at one time, or in the same reaction. For example, combinations using different coloured and/or fluorescent labels and/or different ratios of different coloured and/or fluorescent labels may be used.

In various embodiments of the present invention, a second or further protector strand of the nucleic acid probe and/or of a separate activator molecule (if present), and/or of a separate primer (if present) may be provided in a modified form such that they are resistant to 3' exonuclease activity. Modifications to nucleic acid molecules or to nucleotides contained within a nucleic acid molecule, to prevent degradation by exonucleases are well known in the art and generally utilise the modification of one or more residues at the protected end, e.g. the 3' end. Any modification that is suitable for the protection against 3' exonuclease activity may be utilised in the methods of the invention. In this respect, the primer sequence of a probe or of a separate activator molecule (or indeed of a separately added primer), for example a primer sequence lying at the 3' end of the second or further protector strand or of an activator molecule, preferably comprises at least one modified nucleotide at the 3' end. For instance, the modifications may be selected from any one or more of the list comprising a thiophosphate-modified nucleotide, phosphorothioate nucleotide a locked nucleic acid nucleotide (inaccessible RNA nucleotide), a 2'-OMe-CE Phosphoramidite modified nucleotide, or a peptide nucleic acid nucleotide.

In certain other embodiments, it may be desirable for the second or further protector strand of the probe to comprise a modification or block at or near the 3' end which acts to inhibit extension (e.g. a "polymerase-block" or "extension block"). This may be useful to protect from extension a 3' end of a second protector strand which is not intended to provide a primer for RCA, for example in an embodiment where the probe is activated by a separate activator molecule which also provides the primer for RCA, e.g. as depicted in FIGS. 23 and 24. In such an embodiment, the 3' end of the second protector strand of the probe is protected from both degradation and extension. The 3' end of the activator molecule provides the RCA primer and is protected from degradation but not extension.

The present invention provides use of a nucleic acid probe as defined herein in the detection of a target nucleic acid molecule, wherein said probe is activatable in the presence of the target nucleic acid to generate an RCA product (i.e. wherein upon binding of the probe to the target nucleic acid, the probe is activated to allow RCA of the template strand of the probe).

The present invention may thus also be seen to provide methods for the detection of a target nucleic acid molecule, using the nucleic acid probes as described herein. At its broadest, the present invention provides a method for detecting a target nucleic acid molecule by an RCA reaction, said method comprising:

a) contacting the target nucleic acid molecule with a nucleic acid probe as hereinbefore described;

b) if the probe is activated by a separate activator molecule, simultaneously or separately before or after step (a), contacting the target nucleic acid molecule with a separate activator molecule, said activator molecule comprising a binding site for the target molecule and a binding site complementary and capable of binding to the activator binding site in the nucleic acid probe;

c) allowing the target nucleic acid molecule to bind to the separate activator molecule, if present;

d) allowing the target nucleic acid molecule and, if present, separately or simultaneously the separate activator molecule to bind to the nucleic acid probe, wherein binding of the target molecule, or if present the activator molecule, to the probe causes a strand displacement reaction which activates the probe to allow RCA of the first template strand of the probe;

e) performing an RCA reaction using the first template strand as the RCA template; and f) detecting the RCA product from step (e), thereby to detect the target nucleic acid sequence.

Components of the detection reaction may be added to, or contacted with, a sample containing the target nucleic acid molecule sequentially or simultaneously. In certain embodiments the components of the detection reaction may be pre-mixed prior to addition to a sample. Thus for example a probe and other reagents for a RCA reaction (e.g. polymerase and/or nucleotides and/or a separate primer if necessary) may be pre-mixed, or they may be added together to a sample containing the target, or to the target and separate activator molecule. Thus various components may be pre-mixed, but this will not include the probe and separate activator molecule. In other embodiments, the sample may be contacted with the probe and separate activator molecule at the same, or substantially the same time. For example the probe and the separate activator may be added to the sample, or a sample and a probe may be brought into contact with (e.g. added to) a separate activator molecule (e.g. an immobilised separate activator molecule as depicted in FIG. 23). In still other embodiments, any one or more of the components may be contacted, e.g. pre-incubated, with the sample prior to the addition of other components required to activate RCA and detect the target. For example the sample containing the target molecule may be contacted with the separate activator molecule, and then with the probe.

As described herein, the target binding site(s) or, if present, the binding site for the separate activator molecule in a second or further protector strand may lie at least partially within the loop or envelope structure, and thus may be hybridised to the first circular template strand to form a double-stranded circular structure. Thus, in certain embodiments of the method of the present invention, binding of the target nucleic acid molecule or of the activator molecule to the probe displaces at least a portion of a second or further protecting strand from the first circular template strand, thereby exposing a region of the first circular template strand, allowing an RCA primer to bind to the exposed region to initiate rolling circle amplification.

In the methods of the present invention, a separate activator molecule, which binds to and is recruited by the target nucleic acid, may be used to activate the nucleic acid probe, and thus in certain embodiments a separate activator molecule may be provided to activate the nucleic acid probe. The separate activator molecule, where used, comprises a binding site for the target nucleic acid molecule, and binds (hybridises) thereto and is thereby recruited by the target nucleic acid molecule. Thus in certain embodiments, the nucleic acid probe and the separate activator molecule may both bind to the target nucleic acid, wherein the binding site for the separate activator molecule within the target nucleic acid molecule is distinct from, or more particularly, spatially separate from, the binding site for the nucleic acid probe within the target nucleic acid molecule. The target nucleic acid molecule thus may comprise two separate binding sites for the nucleic acid probe and separate activator molecule, respectively, and conversely the separate activator molecule comprises a target binding site and a separate and distinct probe binding site, such that it may simultaneously bind to both the target and the probe. Preferably, the target binding site in the separate activator molecule may be situated at an end of the separate activator molecule, i.e. at the 5' or at the 3' end of the molecule (though this will depend on the orientation and design of the nucleic acid probe used in the detection method). The separate activator molecule further comprises a region of complementarity for the binding site for the separate activator molecule in the nucleic acid probe (i.e. a probe binding site), and, when present, binds to the activator binding site (e.g. to the second single-stranded region of certain probe embodiments as set out above) of the nucleic acid probe in the course of activating the probe of the invention. In some embodiments said region of complementarity will be situated at an end of the separate activator molecule, such that the end of the molecule hybridises to a (e.g. the second) protector strand of the nucleic acid probe during the strand displacement/activation step of the invention.

The present invention thus provides methods for the detection of a target nucleic acid, using the nucleic acid probes as described herein, wherein the nucleic acid probe is activated by a separate activator molecule. In this aspect the present invention provides a method comprising:

a) contacting the target nucleic acid molecule with a nucleic acid probe as hereinbefore described;

b) simultaneously or separately before or after step (a), contacting the target nucleic acid molecule with a separate activator molecule, said activator molecule comprising a binding site for the target molecule and a binding site complementary and capable of binding to the activator binding site in the nucleic acid probe;

c) allowing the target nucleic acid molecule to bind to the separate activator molecule;

d) allowing the target nucleic acid molecule and, separately or simultaneously, the separate activator molecule to bind to the nucleic acid probe, wherein binding of the separate activator molecule to the probe causes a strand displacement reaction which activates the probe to allow RCA of the first template strand of the probe;

e) performing an RCA reaction using the first template strand as the RCA template; and f) detecting the RCA product from step (e), thereby to detect the target nucleic acid sequence.

Thus, in certain embodiments, the target nucleic acid is contacted (bound) by both the nucleic acid probe of the invention and the separate activator molecule, and activation of the nucleic acid probe is dependent upon the binding of the separate activator molecule to the target nucleic acid molecule.

Put another way, the production of an RCA product may, in certain embodiments where a separate activator molecule is required and provided, be dependent upon the binding of the nucleic acid probe of the invention, and of a separate activator molecule, to a target nucleic acid molecule. Such binding may be seen to take place in proximity, i.e. both molecules may bind to distinct positions nearby within the target nucleic acid molecule. As noted above, this may alternatively be indirect binding, i.e. binding of a separate activator molecule to an intermediary molecule in proximity to the target molecule. Both the nucleic acid probe and the separate activator molecule may thus comprise target binding sites (nucleic acid sequences complementary to, and capable of hybridising to the target nucleic acid molecule), and regions capable of interacting with one another (i.e. a second single-stranded region and binding site for a separate activator molecule within the nucleic acid probe, and a region of complementarity to the nucleic acid probe within the separate activator molecule). Alternatively, the separate activator molecule may comprise a binding site to an intermediary molecule, in proximity to the target molecule. Accordingly, where the activator for the probe (the activator for the RCA reaction) is a separate activator molecule, the detection assay may be viewed as a proximity-based detection assay comprising the use of a nucleic acid probe of the invention.

Activation of the probe results in either a RCA template/primer complex being formed or generated, from which RCA may be initiated directly (e.g. when the primer is provided by or generated from the probe or the separate activator molecule or the target molecule), or in a construct wherein a part or region of the first circular template strand is exposed, allowing the binding of a separate primer molecule to initiate RCA. Thus, in certain embodiment, the primer for RCA may be provided by or from the 3' end region of a (e.g. the second) protector strand, optionally wherein said 3' end region is released by the strand displacement reaction, or from an intermediate region of a (e.g. the second) protector strand (e.g. where the 3' end region is removed by cleavage). Thus in certain embodiments a (e.g. the second) protector strand comprises a free 3' end (i.e. a single-stranded region at its 3' end), whereas in certain other embodiments the 3' end of a (e.g. the second) protector strand is hybridised to a further sequence within the probe, and binding of the target nucleic acid or activator molecule to the probe displaces the sequence hybridised to the 3' end of the protector strand, allowing the 3' end of the protector strand to provide a primer for RCA.

The primer for RCA may alternatively be provided by the target nucleic acid molecule, or, where present, by the separate activator molecule. The target nucleic acid molecule or separate activator molecule may comprise a free 3' end which may bind to the exposed region of the first circular template strand following activation of the probe, thereby to initiate rolling circle amplification. Alternatively, a primer may be generated from the target nucleic acid molecule or activator molecule, i.e. a 3' end may be generated by cleavage (e.g. degradation) of the target nucleic acid or activator molecule. This, in certain embodiments, the primer may be provided by the 3' end region of the activator molecule, or provided by or from the 3' end of the target nucleic acid molecule.

In yet another embodiment, the primer may be provided as a separate nucleic acid molecule. Such a primer will have at least a region of complementarity with the region of the first circular template strand that is exposed following activation of the probe, and will be able to bind thereto following binding of the probe to the target nucleic acid or activator molecule, thereby to initiate rolling circle amplification. A separately-added nucleic acid molecule may be provided at any stage of the method of the present invention prior to the initiation of RCA, i.e. it may be provided simultaneously with or after any of steps (a), (b), (c) or (d).

Binding of a separately-added primer may only take place following activation of the probe, however, i.e. binding of the primer to the first circular template strand occurs following activation of the probe in step (d).

Where the nucleic acid probe comprises a stem-loop structure comprising a partially double-stranded stem region comprising a duplex between the 5' and 3' end regions of the second protector strand, binding of the target nucleic acid molecule, or if present, the separate activator molecule, to the probe displaces the 3' end region from the 5' end region of the second protector strand, thereby opening at least the stem of the stem-loop structure to activate the probe. Analogously, where the nucleic acid probe comprises two or more protector strands having regions of complementarity at their 5' and 3' end regions for another protector strand and forming partially double-stranded stem regions comprising a duplex between the respective ends of two protector strands, binding of the target nucleic acid molecule, or if present, the separate activator molecule, to the probe displaces the 3' end region of one protector strand from the 5' end region of another protector strand, thereby opening at least the stem to activate the probe.

In a particular embodiment of such a method, the opening of a stem results in the release of a 3' end region of a (e.g. the second) protector strand, which may render the 3' end region susceptible to cleavage (e.g. enzymatic cleavage), to generate a primer for the RCA reaction. The method of the present invention may thus further comprise a step of cleavage of a released 3' end region to generate a primer for the RCA reaction.

The term "cleavage" is used broadly herein to include any method of breaking a covalent bond (e.g. a phosphodiester bond) which links adjacent nucleotide residues in a nucleotide chain (i.e. in a nucleotide sequence). Cleavage thus involves strand cleavage or strand scission. The cleavage may be at a distinct cleavage site, (e.g. a restriction or nickase cleavage site) or may involve successive removal of nucleotides e.g. from the end of a nucleotide chain (e.g. degradation of a nucleotide sequence). The cleavage may thus be endonucleolytic or exonucleolytic cleavage.

Said cleavage may be enzymatic cleavage and may in certain embodiments be performed by a component having 3' exonuclease activity. In one embodiment, the component having 3' exonuclease activity may be a polymerase enzyme.

The present invention thus provides a method for detecting a target nucleic acid molecule by an RCA reaction, said method comprising:

a) contacting the target nucleic acid molecule with a nucleic acid probe as hereinbefore described, wherein said probe comprises a stem-loop structure comprising a partially double-stranded stem region comprising a duplex between the 5' and 3' end regions of the second protector strand;

b) if the probe is activated by a separate activator molecule, simultaneously or separately before or after step (a), contacting the target nucleic acid molecule with a separate activator molecule, said activator molecule comprising a binding site for the target molecule and a binding site complementary and capable of binding to the activator binding site in the nucleic acid probe;

c) allowing the target nucleic acid molecule to bind to the separate activator molecule, if present;

d) allowing the target nucleic acid molecule and, if present, separately or simultaneously the separate activator molecule to bind to the nucleic acid probe, wherein binding of the target molecule, or if present the activator molecule, to the probe displaces the 5' end region from the 3' end region of the second protector strand, thereby opening the stem and releasing the 3' end region of the second protector strand and exposing it to cleavage;

d'), further cleaving said released 3' end region to generate a primer for the RCA reaction;

e) performing an RCA reaction using said primer from step (d') and the first template strand as the RCA template; and f) detecting the RCA product from step (e), thereby to detect the target nucleic acid sequence.

In other embodiments, as described above, such a cleavage step to generate the primer is not necessary, and the strand displacement reaction which activates the probe results in displacement of at least a portion of a (e.g. the second) protecting strand from the first circular template strand, thereby exposing a region of the first circular template strand, allowing an RCA primer to bind to the exposed region to initiate rolling circle amplification. The primer may be a primer sequence lying at the 3' end of a (e.g. the second) protector strand or at the 3' end of a separate activator molecule. Alternatively it may be a separately added primer molecule. In such cases, the method may further comprise a step of allowing a primer to bind to the exposed region of the first circular template strand.

The probe used in such methods may, in certain embodiments, comprise a single-stranded region at the 5' end of a (e.g. the second) protector strand, wherein said single-stranded region comprises at least an accessible part of the target binding site. Binding of the target nucleic acid molecule to the probe may thereby disrupt a duplex region and displace a portion of a (e.g. the second) protector strand from the first template strand, thereby exposing a region of the first circular template strand and allowing an RCA primer to bind to the exposed region. In certain embodiments, the probe may comprise a region at the 3' end of a (e.g. the second) protector strand which is complementary to the exposed region of the first circular template strand, and is thus able to bind to the exposed region and act as a primer for RCA.

In other embodiments, the probe may comprise a first single-stranded region at the 5' end of a (e.g. the second) protector strand comprising at least an accessible part of the target binding site, and a second single-stranded region at the 3' end of a (e.g. the second or further) protector strand comprising at least an accessible part of a binding site for a separate activator molecule. Binding of the separate activator molecule to the probe disrupts the duplex region and displaces a portion of a (e.g. the second) protector strand from the first template strand, thereby exposing a region of the first circular template strand and allowing an RCA primer to bind to the exposed region In certain embodiments, the separate activator molecule may comprise a region at its 3' end which is complementary to the exposed region of the first circular template strand, and is thus able to bind to the exposed region and act as a primer for RCA.

The target nucleic acid detected by the probes of the present invention may be a target analyte of interest, i.e. an analyte present in a sample, the detection of which may be of interest, or it may be a reporter or marker nucleic acid molecule which is indicative of the presence of a target analyte in a sample (i.e. it may be a "surrogate" for a target analyte). The target nucleic acid molecule may therefore be any kind of nucleic acid molecule. Thus it may be DNA or RNA, or a modified variant thereof. The nucleic acid may be made up of ribonucleotides and/or deoxyribonucleotides as well as synthetic nucleotides that are capable of participating in Watson-Crick type or analogous base pair interactions. Thus the target nucleic acid may be or may comprise, e.g. bi-sulphite converted DNA, LNA, PNA or any other derivative containing a non-nucleotide backbone.

In certain embodiments, the target nucleic acid molecule is a target analyte. The target nucleic acid molecule may be coding or non-coding DNA, for example genomic DNA or a sub-fraction thereof, or may be derived from genomic DNA, e.g. a copy or amplicon thereof, or it may be cDNA or a sub-fraction thereof, or an amplicon or copy thereof etc. Alternatively, the target molecule may be or may be derived from coding (i.e. pre-mRNA or mRNA) or non-coding RNA sequences (such as tRNA, rRNA, snoRNA, miRNA, siRNA, snRNA, exRNA, piRNA and long ncRNA).

In an alternative embodiment, the target nucleic acid may be a reporter oligonucleotide or nucleic acid molecule indicative of the presence of a target analyte. The target nucleic acid may therefore be the product of a previous amplification reaction, e.g. a previous PCR reaction, RCA reaction or LCR reaction, or may be a nucleic acid molecule formed as a result of a previous ligation or extension reaction, e.g. in a proximity dependent manner (the nucleic acid molecule may be the product of a proximity ligation assay or a proximity extension assay). The target nucleic acid molecule may be the product of a previous RCA reaction (a RCA product), which product may in certain embodiments be indicative of the presence of a target analyte in a sample e.g. formed as a result of a proximity-based detection assay. Where the target nucleic acid molecule is the product of a previous RCA reaction (i.e. the amplification product formed from a previous circular template), the target binding site may be seen to be complementary to at least a portion of the circle used as a template for the previous RCA reaction. The target nucleic acid molecule may alternatively be the nucleic acid domain of a probe binding to a target analyte, for example a proximity probe or any antibody-based probe. Activation of the probe may therefore be accomplished by a nucleic acid molecule provided in a sample which is indicative of the presence of a target analyte, rather than the target analyte itself.

In a particular embodiment, the target nucleic acid molecule may be the nucleic acid domain of a probe binding to a target analyte, and the nucleic acid probe may be the nucleic acid domain of a further probe which also binds to the target analyte. Such probes may accordingly be viewed as a pair of proximity probes for a target analyte. Upon binding of the probes comprising the target nucleic acid molecule and the nucleic acid probe to the target analyte, the nucleic acid probe may 'detect' the target nucleic acid molecule in a manner hereinbefore described, leading to the generation of a detectable RCA product. In a further particular embodiment, the target nucleic acid molecule may be the nucleic acid domain of a probe binding to a target analyte, and the intermediary molecule may be the nucleic acid domain of a further probe which also binds to the target analyte. Such probes may similarly be viewed as a pair of proximity probes for a target analyte. In such an embodiment, a nucleic acid probe may bind to the target nucleic acid molecule and a separate activator molecule may bind to the intermediary molecule (i.e. in proximity to the nucleic acid probe). Upon binding of the probes comprising the target nucleic acid molecule and the intermediary molecule to the target analyte, the separate activator molecule may activate the nucleic acid probe, thereby leading to the generation of a detectable RCA product. In yet another embodiment, the target nucleic acid molecule may be the nucleic acid domain of a probe binding to the target analyte, and the separate activator molecule may be the nucleic acid domain of a further probe which also binds to the target analyte, and such probes may also be viewed as a pair of proximity probes for a target analyte. In such an embodiment, a nucleic acid probe may bind to the target nucleic acid molecule and the separate activator molecule. Thus, upon binding of the probes comprising the target nucleic acid molecule and the separate activator molecule to the target analyte, the nucleic acid probe may be activated, thereby leading to the generation of a detectable RCA product. The present invention thus provides proximity-based detection methods for the detection of a target analyte in a sample in which the nucleic acid probe as disclosed herein is provided as the nucleic acid domain of a first proximity probe which binds to a target analyte, and the target nucleic acid molecule is provided as the nucleic acid domain of a second proximity probe which binds to a target analyte, wherein the first and second proximity probes bind to the target in proximity, and wherein when said first and second proximity probes are bound to the target analyte in proximity, the nucleic acid domain of the second proximity probe (the target nucleic acid molecule) is able to interact with the nucleic acid domain of the first proximity probe (the nucleic acid probe of the invention) and activate rolling circle amplification. Such an arrangement is shown in FIG. 14.

The present invention thus provides a method for detecting a target analyte in a sample, said method comprising:
(i) contacting the target analyte with at least a first and second proximity probe, wherein said probes each comprise an analyte-binding domain and a nucleic acid domain and can simultaneously bind to the target analyte, wherein the nucleic acid domain of the first proximity probe is a nucleic acid probe as hereinbefore described, and wherein the nucleic acid domain of the second proximity probe is a target nucleic acid molecule comprising a binding site complementary and capable of binding to the target binding site in the nucleic acid probe;
(ii) allowing the nucleic acid domains of the proximity probes to interact with each other upon binding of the proximity probes to said analyte, wherein said interaction causes a strand displacement reaction which activates the probe to allow RCA of the first template strand of the probe;
(iii) performing an RCA reaction using the first template strand as the RCA template
(iv) detecting the RCA product from step (c), thereby to detect the target analyte in the sample.

The present invention also provides a method for detecting a target analyte in a sample, said method comprising:
(i) contacting the target analyte with
a. a nucleic acid probe as hereinbefore described, and a separate activator molecule for the probe; and
b. at least a first and second proximity probe, wherein said probes each comprise an analyte-binding domain and a nucleic acid domain and can simultaneously bind to the target analyte, wherein the nucleic acid domain of the first proximity probe is a target nucleic acid molecule comprising a binding site complementary and capable of binding to the target binding site in the nucleic acid probe, and wherein the nucleic acid domain of the second proximity probe is an intermediary molecule comprising a binding site complementary and capable of binding to a binding site in a separate activator molecule;
wherein said nucleic acid probe and separate activator molecule contact the target analyte simultaneously with or after the at least first and second proximity probe;
(ii) allowing the nucleic acid probe and separate activator molecule to bind to the nucleic acid domains of the proximity probes, wherein the nucleic acid probe and separate activator molecule interact with each other upon binding of the proximity probes to said analyte, wherein said interaction causes a strand displacement reaction which activates the probe to allow RCA of the first template strand of the probe;
(iii) performing an RCA reaction using the first template strand as the RCA template; and
(iv) detecting the RCA product from step (iii), thereby to detect the target analyte in the sample.

The present invention also provides a method for detecting a target analyte in a sample, said method comprising:
(i) contacting the target analyte with
a. a nucleic acid probe as hereinbefore described; and
b. at least a first and second proximity probe, wherein said probes each comprise an analyte-binding domain and a nucleic acid domain and can simultaneously bind to the target analyte, wherein the nucleic acid domain of the first proximity probe is a target nucleic acid molecule comprising a binding site complementary and capable of binding to the target binding site in the nucleic acid probe, and wherein the nucleic acid domain of the second proximity probe is a separate activator molecule, said activator molecule comprising a binding site complementary and capable of binding to the activator binding site in the nucleic acid probe;
wherein said nucleic acid probe contacts the target analyte simultaneously with or after the at least first and second proximity probe;
(ii) allowing the nucleic acid probe to bind to the nucleic acid domains of the proximity probes, wherein the nucleic acid probe and separate activator molecule interact with each other upon binding of the proximity probes to said analyte, wherein said interaction causes a strand displacement reaction which activates the probe to allow RCA of the first template strand of the probe;
(iii) performing an RCA reaction using the first template strand as the RCA template; and
(iv) detecting the RCA product from step (iii), thereby to detect the target analyte in the sample.

The proximity probes for use in such methods are in effect detection probes which bind to the analyte (via the analyte-binding domain), the binding of which may be detected (to detect the analyte) by means of detecting the interaction which occurs between the nucleic acid domains thereof upon such binding. Accordingly the probes may be viewed as nucleic acid-tagged affinity ligands or binding partners for the analyte, the analyte-binding domain being the affinity binding partner, and the nucleic acid domain the nucleic acid tag. The nucleic acid domain is coupled to the analyte-binding domain and this "coupling" or connection may be by any means known in the art, and which may be desired or convenient and may be direct or indirect e.g. via a linking group. For example, the domains may be associated with one another by covalent linkage (e.g. chemical crosslinking) or by non-covalent association e.g., via streptavidin-biotin based coupling (biotin being provided on one domain and streptavidin on the other).

The analyte binding domain may be any binding partner for the target analyte, and it may be a direct or indirect binding partner therefor. Thus it may bind to the target analyte directly, or indirectly via an intermediary molecule or binding partner which binds to the target analyte, the analyte binding domain binding to said intermediary molecule (binding partner). Particularly, the analyte-binding domain or the intermediary binding partner is a specific binding partner for the analyte. A binding partner is any molecule or entity capable of binding to its target, e.g. target analyte, and a specific binding partner is one which is capable of binding specifically to its target (e.g. the target analyte), namely that the binding partner binds to the target (e.g. analyte) with greater affinity and/or specificity than to other components in the sample. Thus binding to the target analyte may be distinguished from non-target analytes; the specific binding partner either does not bind to non-target analytes or does so negligibly or non-detectably or any such non-specific binding, if it occurs, may be distinguished. The binding between the target analyte and its binding partner is typically non-covalent.

The analyte binding domain may be selected to have a high binding affinity for a target analyte. By high binding affinity is meant a binding affinity of at least about $10^{-4}$M, usually at least about $10^{-6}$ M or higher, e.g., $10^{-9}$ M or higher. The analyte binding domain may be any of a variety of different types of molecules, so long as it exhibits the requisite binding affinity for the target protein when present as part of the proximity probe. In other embodiments, the analyte binding domain may be a ligand that has medium or even low affinity for its target analyte, e.g., less than about $10^{-4}$ M.

The analyte binding domain may be a small molecule or large molecule ligand. By small molecule ligand is meant a ligand ranging in size from about 50 to about 10,000 Daltons, usually from about 50 to about 5,000 Daltons and more usually from about 100 to about 1000 Daltons. By large molecule is meant a ligand ranging in size from about 10,000 Daltons or greater in molecular weight. The small molecule may be any molecule, as well as a binding portion or fragment thereof, that is capable of binding with the requisite affinity to the target analyte. Generally, the small molecule is a small organic molecule that is capable of binding to the target analyte of interest. The small molecule will include one or more functional groups necessary for structural interaction with the target analyte, e.g. groups necessary for hydrophobic, hydrophilic, electrostatic or even covalent interactions. Where the target analyte is a protein, the small molecule ligand will include functional groups necessary for structural interaction with proteins, such as hydrogen bonding, hydrophobic-hydrophobic interactions, electrostatic interactions, etc., and will typically include at least an amine, amide, sulfhydryl, carbonyl, hydroxyl or carboxyl group, preferably at least two of the functional chemical groups. The small molecule may also comprise a region that may be modified and/or participate in covalent linkage to the nucleic acid domain of the proximity probe, without substantially adversely affecting the small molecule's ability to bind to its target analyte.

Small molecule affinity ligands often comprise cyclical carbon or heterocyclic structures and/or aromatic or polyaromatic structures substituted with one or more of the above functional groups. Also of interest as small molecules are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The small molecule may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known small molecules may be subjected to directed or random chemical modifications, such as acylation, alkylation, esterification, amidification, etc., to produce structural analogs.

As such, the small molecule may be obtained from a library of naturally occurring or synthetic molecules, including a library of compounds produced through combinatorial means, i.e. a compound diversity combinatorial library. When obtained from such libraries, the small molecule employed will have demonstrated some desirable affinity for the protein target in a convenient binding affinity assay. Combinatorial libraries, as well as methods for their production and screening, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

The analyte binding domain may also be a large molecule. Of particular interest as large molecule analyte binding domains are antibodies, as well as binding fragments and derivatives or mimetics thereof. Where antibodies are the analyte binding domain, they may be derived from polyclonal compositions, such that a heterogeneous population of antibodies differing by specificity are each "tagged" with the same tag nucleic acid (nucleic acid domain) or monoclonal compositions, in which a homogeneous population of identical antibodies that have the same specificity for the target analyte are each tagged with the same tag nucleic acid. As such, the analyte binding domain may be either a monoclonal or polyclonal antibody. In yet other embodiments, the affinity ligand is an antibody binding fragment or derivative or mimetic thereof, where these fragments, derivatives and mimetics have the requisite binding affinity for the target analyte. For example, antibody fragments, such as Fv, F(ab)2 and Fab may be prepared by cleavage of the intact protein, e.g. by protease or chemical cleavage. Also of interest are recombinantly or synthetically produced antibody fragments or derivatives, such as single chain antibodies or scFvs, or other antibody derivatives such as chimeric antibodies or CDR-grafted antibodies, where such recombinantly or synthetically produced antibody fragments retain the binding characteristics of the above antibodies. Such antibody fragments or derivatives generally include at least the VH and VL domains of the subject antibodies, so as to retain the binding characteristics of the subject antibodies. Such antibody fragments, derivatives or mimetics of the subject invention may be readily prepared using any convenient methodology, such as the methodology disclosed in U.S. Pat. Nos. 5,851,829 and 5,965,371; the disclosures of which are herein incorporated by reference.

The above described antibodies, fragments, derivatives and mimetics thereof may be obtained from commercial sources and/or prepared using any convenient technology, where methods of producing polyclonal antibodies, monoclonal antibodies, fragments, derivatives and mimetics thereof, including recombinant derivatives thereof, are known to those of the skill in the art.

Also suitable for use as binding domains are polynucleic acid aptamers. Polynucleic acid aptamers may be RNA oligonucleotides which may act to selectively bind proteins, much in the same manner as a receptor or antibody (Conrad et al., Methods Enzymol. (1996), 267 (Combinatorial Chemistry), 336-367).

In certain embodiments where the analyte binding domain is a nucleic acid, e.g., an aptamer, the target analyte is not a nucleic acid. However, the analyte binding domain may in other circumstances be an oligonucleotide probe, i.e. a probe being complementary to a sequence within a target nucleic acid molecule, and capable of hybridising thereto.

Importantly, the analyte binding domain will be one that includes a moiety that can be covalently attached to the nucleic acid domain without substantially abolishing the binding affinity of the analyte binding domain to its target analyte.

In addition to antibody-based peptide/polypeptide or protein-based binding domains, the analyte binding domain may also be a lectin, a soluble cell-surface receptor or derivative thereof, an affibody or any combinatorially derived protein or peptide from phage display or ribosome display or any type of combinatorial peptide or protein library. Combinations of any analyte-binding domain may be used.

The binding sites on the analyte for the respective analyte-binding domains of the proximity probes in a set may be the same or different. Thus, for example in the case of a homomeric protein complex or aggregate comprising two or more identical subunits or protein constituents, the analyte-binding domains of two or more probes may be the same. Where the analyte is a single molecule or comprises different sub-units or constituents (e.g. a heteromeric complex or an aggregate of different proteins), the analyte binding domains will be different.

Binding sites on the analyte for the analyte binding domain need not be on the same molecule. They may be on separate, but closely positioned, molecules. For example, the multiple binding domains of an organism, such as a bacterium or cell, or a virus, can be targeted by the proximity detection methods of the present invention.

In certain embodiments, the target analyte (e.g. a target nucleic acid molecule or a target analyte which is a target for a detection probe such as proximity probe) may be immobilised on a solid support or surface e.g. in an array, or may be fixed or immobilised within a biological sample, e.g. a fixed cell or tissue sample. The present invention may thereby thus provide in certain embodiments an in situ method for the detection of a target analyte in a sample.

Immobilisation of the analyte on a solid phase (i.e. support or surface) may be achieved in various ways. Accordingly, several embodiments of solid phase assays are contemplated. In one such embodiment, the analyte can first be captured by an immobilised (or immobilisable) capture probe and then bound by subsequently added probe(s). The immobilised capture probe may be immobilised, i.e. bound to the support, in any convenient way. Thus the manner or means of immobilisation and the solid support may be selected, according to choice, from any number of immobilisation means and solid supports as are widely known in the art and described in the literature. Thus, the capture probe may be directly bound to the support (e.g. chemically cross-linked), it may be bound indirectly by means of a linker group, or by an intermediary binding group(s) (e.g. by means of a biotin-streptavidin interaction and/or it may comprise an oligonucleotide which hybridises to a cognate oligonucleotide provided on the solid support). Thus, a capture probe may be provided with means for immobilisation (e.g. an affinity binding partner, e.g. biotin or a hapten or a nucleic acid molecule, capable of binding to its binding partner, i.e. a cognate binding partner, e.g. streptavidin or an antibody or a nucleic acid molecule) provided on the support. The probe may be immobilised before or after binding to the analyte. Further, such an "immobilisable" capture probe may be contacted with the sample together with the support. FIG. 14 shows a representative depiction of a target analyte (in this case a protein) immobilised on a solid support by means of an antibody-based capture probe, wherein the capture probe comprises an antibody conjugated to an oligonucleotide which comprises a sequence complementary to an oligonucleotide immobilised on the solid support.

The capture probe may be, for example, an antibody or nucleic acid molecule that is capable of binding to the target analyte specifically. In other words the capture probe may be an immobilised (or immobilisable) analyte-specific probe comprising an analyte binding domain (i.e. an analyte capture probe). Thus in such an embodiment the analyte is first captured by the immobilised or immobilisable capture probe which serves only to immobilise the analyte on the solid phase, and subsequently the immobilised analyte is incubated with the probe of the invention. In such an embodiment, the capture probe may be any binding partner capable of binding the analyte, directly or indirectly, as discussed above in related to intermediary binding partners. More particularly, such a capture probe binds specifically to the analyte.

The solid support may be any of the well-known supports or matrices which are currently widely used or proposed for immobilisation, separation etc. These may take the form of particles (e.g. beads which may be magnetic or non-magnetic), sheets, gels, filters, membranes, fibres, capillaries, or microtitre strips, tubes, plates or wells etc. The support may be made of glass, silica, latex or a polymeric material. Suitable are materials presenting a high surface area for binding of the analyte. Such supports may have an irregular surface and may be for example porous or particulate e.g. particles, fibres, webs, sinters or sieves. Particulate materials e.g. beads are useful due to their greater binding capacity, particularly polymeric beads. Conveniently, a particulate solid support used according to the invention will comprise spherical beads. The size of the beads is not critical, but they may for example be of the order of diameter of at least 1 and preferably at least 2 μm, and have a maximum diameter of preferably not more than 10, and e.g. not more than 6 μm.

Monodisperse particles, that is those which are substantially uniform in size (e.g. size having a diameter standard deviation of less than 5%) have the advantage that they provide very uniform reproducibility of reaction. Representative monodisperse polymer particles may be produced by the technique described in U.S. Pat. No. 4,336,173.

However, to aid manipulation and separation, magnetic beads are advantageous. The term "magnetic" as used herein means that the support is capable of having a magnetic moment imparted to it when placed in a magnetic field, i.e. paramagnetic, and thus is displaceable under the action of that field. In other words, a support comprising magnetic particles may readily be removed by magnetic aggregation, which provides a quick, simple and efficient way of separating the particles following the analyte binding steps.

In a further embodiment, the analyte itself may be immobilised (or immobilisable) on the solid phase e.g. by non-specific absorption. In a particular such embodiment, the analyte may be present within cells, being optionally fixed and/or permeabilised, which are (capable of being) attached to a solid support, e.g. a tissue sample comprising analyte may be immobilised on a microscope slide.

Furthermore, in certain embodiments, the nucleic acid probe, and/or, if present, the separate activator molecule may be immobilised on a solid surface. Immobilisation may be direct, i.e. by attaching a nucleic acid molecule directly to a solid surface, preferably at one of its termini, or may also be indirect, i.e. by allowing a nucleic acid molecule to hybridise to a further nucleic acid molecule that is directly attached to the solid surface. Attachment of a nucleic acid molecule to a surface may be performed by any convenient method, e.g. a method as described herein.

In a particular embodiment, wherein the nucleic acid probe is activatable by a separate activator molecule, the separate activator molecule may be immobilised directly to a solid support (e.g. an array) by an end thereof e.g. by its 5' end. In such an embodiment, the target nucleic acid molecule binds to the nucleic acid probe and the separate activator molecule, bringing the nucleic acid probe into proximity with the activator molecule, and localising the nucleic acid probe and target nucleic acid molecule to the solid support. Preferably in such an embodiment the primer for the RCA reaction may be provided by the 3' end of the separate activator molecule, and thus the RCA product formed upon the detection of the target nucleic acid molecule may remain bound to (i.e. immobilised to) the solid support. Such an embodiment is depicted in FIG. 23. Immobilising the separate activator molecule has the advantage that unbound molecules (including unbound probes and/or other unbound non-target nucleic acid molecules present in a sample) may be removed, e.g. by washing the support or by separating it from the sample or reaction mixture.

In another particular embodiment the nucleic acid probe of the invention may be immobilised on a solid support and may be designed to be released from the solid support upon target recognition. In such a configuration, an end region (e.g. a 5' end region) of the probe which comprises the accessible part (domain) of the target binding site may comprise a further (second) inaccessible part (domain) of the target binding site which is hybridised to an oligonucleotide immobilised on a solid support. Thus, this second domain is complementary to a region of the immobilised oligonucleotide which is identical to a sequence in the target molecule which is adjacent to the sequence in the target molecule which hybridises to the first accessible domain of the target binding site. When the target molecule hybridises to the first accessible domain, strand displacement occurs to displace the immobilised oligonucleotide, thereby releasing the probe from the solid support. In this way target binding may both activate and release the nucleic acid probe from the solid support. Such an arrangement is depicted in FIG. 22. This may be advantageous in that only released probes may be detected, thereby improving sensitivity (false starters may be eliminated). Advantageously, use of a homogeneous detection system in combination with such an embodiment may enhance the sensitivity of the detection method, as only those probe molecules which have bound to the target will be dissociate from the solid surface, and thus detectable in solution, i.e. away from the solid support, whereas the RCA product formed from probes which undergo non-specific or spontaneous activation will remain and only be detectable on the solid support.

As an alternative to using a solid support, a homogenous assay may be performed, which is conducted in solution (i.e. without a solid phase) using a dilution step, for example analogously to the protein detection assay as described in Example 5. Thus, such a method, comprising a dilution step may be used in the context of detecting proteins using proximity probes (as described in Example 5) or to detect a nucleic acid target analyte (e.g. DNA or RNA). The dilution step may be performed after contacting the target analyte (e.g. target nucleic acid molecule analyte) with the probe, and optionally the separate activator molecule (which may be provided as part of proximity probes), for example the reaction mixture may be diluted from 5 to 50×, or 10 to 30×. Dilution may be performed in step of adding reagents for the RCA reaction, e.g. a buffer containing a polymerase enzyme and/or nucleotides, and/or reagents or conditions for activating a separate activator molecule (see below).

In certain embodiments of the detection method of the present invention, the separate activator molecule or the target nucleic acid molecule may comprise a metastable secondary structure such that it is unable to bind to the nucleic acid probe until released from said metastable secondary structure. In such an embodiment, step (d), which comprises allowing the target nucleic acid molecule and, if present the separate activator molecule, to bind to the nucleic acid probe, comprises a step of introducing permissive conditions to allow the separate activator molecule or the target nucleic acid molecule to bind to the nucleic acid probe.

In preferred embodiments, the metastable secondary structure comprises a stem loop structure, or a hairpin structure, or the target nucleic acid molecule or separate activator molecule is hybridised to a blocking oligonucleotide to form a double-stranded region. The region complementary to the probe binding site (i.e. a region identical to a probe sequence) will be contained within the secondary structure, e.g. within a double-stranded region or a stem structure, whereby it prevents the probe binding site from interacting with a single-stranded region within the nucleic acid probe. The blocking oligonucleotide or strand of the metastable secondary structure which blocks the target or separate activator molecule from binding to the probe may thus be seen as an "activation protector" strand.

As noted above, in one particular embodiment, the region complementary to the probe binding site may be a portion of the target-binding site in the separate activator molecule (i.e. the binding site for the target molecule). In other words, the binding site complementary and capable of binding to the activator binding site in the nucleic acid probe (particularly the portion thereof which binds to the first domain (first accessible domain) of the binding site for the separate activator molecule) may be contained within the secondary structure, whereby it is prevented from binding to the probe by a portion (domain) of the target binding site of the separate activator molecule. Hence, when the target nucleic acid molecule binds to the separate activator molecule, a strand displacement may occur, as the target nucleic acid molecule invades the metastable secondary structure (which contains at least a portion (domain) of the probe binding site of the separate activator molecule), causing the double-stranded part to be opened up, or unfolded, at least in part, thereby exposing the probe binding site in the separate activator molecule.

The present invention thus provides a method for detecting a target nucleic acid molecule by an RCA reaction, said method comprising:
a) contacting the target nucleic acid molecule with a nucleic acid probe as hereinbefore described;
b) contacting the target nucleic acid molecule with a separate activator molecule, said activator molecule comprising a binding site for the target molecule and a binding site complementary and capable of binding to the activator binding site in the nucleic acid probe;
c) allowing the target nucleic acid molecule to bind to the separate activator molecule;
d) allowing the target nucleic acid molecule and separately or simultaneously the separate activator molecule to bind to the nucleic acid probe, wherein binding of the activator molecule to the probe causes a strand displacement reaction which activates the probe to allow RCA of the first template strand of the probe;
e) performing an RCA reaction using the first template strand as the RCA template; and
f) detecting the RCA product from step (e), thereby to detect the target nucleic acid sequence;
wherein:
at least a portion of the target binding site in the nucleic acid probe and at least a portion of the binding site in the nucleic acid probe for the separate activator molecule are complementary and hybridise to each other to form a duplex within a metastable secondary structure, wherein upon binding of the target nucleic acid molecule to the nucleic acid probe the target nucleic acid molecule invades the metastable secondary structure causing the duplex to be unfolded, at least in part, thereby exposing at least the accessible part or portion of the binding site for the separate activator molecule; and/or
at least a portion of the binding site in the separate activator molecule which is complementary and capable of binding to the activator binding site in the nucleic acid probe and at least a portion of the binding site for the target molecule in the separate activator molecule are complementary and hybridise to each other to form a duplex within a metastable secondary structure, and wherein upon binding of the target nucleic acid molecule to the separate activator molecule the target nucleic acid molecule invades the metastable secondary structure, causing the duplex to be unfolded, at least in part, thereby exposing the probe binding site, thereby allowing the separate activator molecule to bind to the probe (i.e. in step (d)).

Such a method, in which both the probe and separate activator molecule comprise metastable secondary structures which are unfolded upon binding to the target nucleic acid molecule, is shown in FIG. 25.

Where a blocking oligonucleotide is used, it will be pre-hybridised to the target nucleic acid molecule or separate activator molecule before the target nucleic acid molecule or separate activator molecule is contacted with the nucleic acid probe of the invention.

The term "permissive conditions" is used broadly herein to refer to any state or condition in which the interacting (i.e. mutually complementary, hybridisable) regions of the nucleic acid probe and target or separate activator molecule (in other words the respective cognate binding sites of the probe and target/separate activator molecule) are able to interact. "Non-permissive" conditions means conversely that the interacting regions are not able to interact, and this includes that an interacting region is protected (or shielded or masked), for example by a separately added blocking oligonucleotide or other molecule that hybridises or binds to it, or by a region of secondary structure in the target or separate activator molecule. That is the target or separate activator molecule may contain a region of self-complementarity. The self-complementary regions may hybridise to one another to form a region of metastable secondary structure. Typically the region of metastable secondary structure will contain a loop of single stranded nucleic acid, more particularly a stem-loop or hairpin structure comprising a double-stranded "stem" region and a single stranded loop.

Permissive conditions may be introduced by removing the blocking oligonucleotide or disrupting or unfolding the metastable secondary structure, e.g. disrupting or displacing or invading the double-stranded stem of a stem-loop or hairpin structure. This may include adding a further reagent or assay component, e.g. an oligonucleotide (an initiator oligonucleotide, as discussed below) which is able to bind to the target nucleic acid or activator molecule to "open up" the metastable secondary structure e.g. to invade or otherwise displace the stem structure or blocking oligonucleotide, or more broadly to induce a conformational change which exposes, and renders accessible for binding, the region of the target nucleic acid molecule or separate activator molecule complementary to a binding site within the nucleic acid probe.

In one embodiment, the target nucleic acid molecule or separate activator molecule may comprise one or more cleavable or degradable groups or nucleotides. A reagent or component may thereby be added, or conditions introduced, which cause or result in the degradation or cleavage of the metastable secondary structure, such that said degradation results in the target nucleic acid molecule or separate activator molecule being able to interact with its complementary sequence within the nucleic acid probe. To this end, the target nucleic acid molecule or separate activator molecule may comprise one or more cleavable or degradable groups or nucleotides, for example ribonucleotides such that it may be digested by addition of a ribonuclease, e.g. RNase, or uracil residues which may be cleaved from the oligonucleotide using an uracil-DNA glycosylase (UNG) enzyme. Removal of one or more uracil bases may destabilise the hybridisation with the blocking oligonucleotide (e.g. the opposite strand of a hairpin) causing it to become displaced or released. Further alternatively the blocking oligonucleotide may comprise one or more cleavage recognition sites for a nickase enzyme. Cleavage of the blocking oligonucleotide by the nickase may cause destabilise its hybridisation causing it to be displaced or released. Thus, in one embodiment, step (d) may comprise cleavage of the activator molecule or of the target molecule, wherein said cleavage exposes a region of complementarity for the activator binding site or the target binding site in the nucleic acid probe. In a particular embodiment, the activator molecule or the target nucleic acid molecule may comprise one or more uracil residues, and step (d) may comprise introducing a uracil-DNA glycosylase enzyme and said cleavage comprises removal or one or more uracil bases. In another embodiment the activator molecule or target nucleic acid molecule comprises one or more nickase or restriction enzyme recognition sites, wherein step (d) comprises introducing a nickase enzyme or restriction enzyme and said cleavage comprises nicking or restriction digestion of the activation molecule or target nucleic acid molecule.

In another embodiment, the introduction of permissive conditions may comprise contacting the target nucleic acid molecule, or, when present, the separate activator molecule, with an initiator oligonucleotide. An initiator is able to hybridise to an accessible initiator binding site (i.e. a toehold region for the initiator). This may be situated in the activation protector strand adjacent to the metastable secondary structure present in a target nucleic acid molecule or a separate activator molecule. The initiator thus comprises a region of complementarity to the initiator binding site in the target/separate activator molecule (and the initiator binding region may accordingly be viewed as a cognate region of complementarity which is accessible in the target or separate activator molecule). Binding to the accessible initiator binding site allows the initiator to invade the metastable secondary structure, displacing a complementary sequence hybridised to the target nucleic acid molecule or separate activator molecule (i.e. displacing the activation protector strand) and causing the metastable secondary structure to open up allowing the target or separate activator molecule to interact with (i.e. hybridise to) its complementary binding site within the nucleic acid probe. The hybridisation and invasion by the initiator thus triggers the activation of the nucleic acid probe, and thus the RCA reaction. Thus, in one embodiment, step (d) comprises introducing an initiator oligonucleotide comprising a region of complementarity to a cognate region of complementarity which is accessible in the separate activator molecule or in the target nucleic acid molecule, wherein the initiator oligonucleotide hybridises to the activator molecule or to the target nucleic acid molecule, unfolding the metastable secondary structure and exposing a region of complementarity for the activator binding site or the target binding site in the nucleic acid probe.

In certain embodiments, the initiator molecule may itself comprise a metastable secondary structure, such that it may not itself induce the unfolding of the target nucleic acid molecule or separate nucleic acid molecule in the absence of permissive conditions. The initiator molecule may therefore comprise one or more cleavable or degradable groups or nucleotides as described herein, or may require a further (e.g. a second) initiator oligonucleotide to hybridise to a secondary structure present therein and invade it, thereby exposing a region of complementarity to a cognate region of complementarity in the target nucleic acid molecule or separate activator molecule. Two (or more) initiator molecules (i.e. a first initiator molecule which activates a second initiator molecule, which in turn activates a separate activator molecule) may therefore be used to activate the nucleic acid probe in the methods of the present invention. One or more initiator molecules may also bind to, or be recruited by, the target nucleic acid molecule, i.e. may comprise binding sites or regions of complementarity for the target nucleic acid molecule. Such a system is depicted in FIG. 24.

An initiator molecule may in certain embodiments be provided in a modified form such that it is resistant to 3' exonuclease activity and may therefore comprise at its 3' end any modification as hereinbefore described for this purpose. Furthermore, in certain embodiments an initiator molecule may comprise a modification or block at or near the 3' end which acts to inhibit extension (e.g. a "polymerase-block" or "extension block"). Initiators comprising such modifications are depicted in FIGS. 23 and 24.

In yet another embodiment, the present invention provides a method of detecting a target nucleic acid molecule using a pair of nucleic acid probes, wherein each probe of the pair is capable of being activated by the RCA product formed as result of the activation of the other probe. The probes may thus be viewed as cognate partners, wherein each probe is activatable following the activation of the other. Such a system is depicted in FIG. 19. Thus, in one embodiment, the present invention provides a method of detecting a target nucleic acid molecule, said method comprising:
(i) contacting the target nucleic acid molecule with a pair of nucleic acid probes as hereinbefore described, wherein the first probe is activatable in the presence of the target nucleic acid molecule, and the target binding site of the first probe is homologous to a portion of the first circular template strand of the second probe and is able to bind to a complement thereof, and wherein the target binding site of the second probe is homologous to a portion of the first circular template strand of the first probe and is able to bind to a complement thereof, and wherein the first probe is activatable in the presence of an RCA product generated from the second probe and the second probe is activatable in the presence of an RCA product generated from the first probe;
(ii) allowing the target nucleic acid molecule to bind to the first nucleic acid probe, wherein binding of the target molecule to the probe causes a strand displacement reaction which activates the first probe to allow RCA of the first template strand of the first probe;
(iii) performing an RCA reaction using the first template strand of the first nucleic acid probe as the RCA template;
(iv) allowing the RCA product from step (iii) to bind to the second nucleic acid probe, wherein binding of the RCA product to the probe causes a strand displacement reaction which activates the second probe to allow RCA of the first template strand of the second probe;
(v) performing an RCA reaction using the first template strand of the second nucleic acid probe as the RCA template;
(vi) allowing the RCA product from step (v) to bind to the first nucleic acid probe, wherein binding of the RCA product to the probe causes a strand displacement reaction which activates the first probe to allow RCA of the first template strand of the first probe;
(vii) optionally repeating steps (iv)-(vi);
(viii) detecting the RCA products formed in any of steps (v)-(vii), thereby to detect the target nucleic acid sequence.

In this embodiment the present invention thus provides a method for the exponential amplification of a signal generated upon the detection of a target nucleic acid sequence, as each successive RCA product will activate multiple further nucleic acid probes. The above method is not, however, limited to requiring a pair of nucleic acid probes, as through appropriate probe design, it may be possible to design an exponential amplification system in which three or four or more alternating RCA reactions take place, wherein each RCA product is capable of activating the next nucleic acid probe in the sequence (e.g. the RCA product formed from a first probe may activate a second probe, the RCA product formed from a second probe may activate a third probe and so on). Furthermore, an exponential amplification system in which a single species of nucleic acid probe is used is also contemplated, i.e. where an RCA product is capable of activating the nucleic acid probe used to generate said RCA product. In such an embodiment, the first and second probes described above may be seen to be the same.

In addition to the components described above, the reaction mixture for the RCA reaction of the subject methods typically includes a polymerase and deoxyribonucleoside triphosphates (dNTPs). The step of performing the RCA reaction using a first circular template strand of the probe as template for extension of the RCA primer in a polymerase reaction may be performed according to principles well known in the art. Rolling-circle amplification (RCA) is well known in the art, being described in Dean et al., 2001 Genome Research, 11, pp. 1095-1099, the disclosures of which are herein incorporated by reference. Any polymerase suitable for a RCA reaction may be used. Specifically this will be a strand-displacing polymerase, typically Phi29 polymerase. The desired polymerase activity may be provided by one or more distinct polymerase enzymes. In some embodiments the polymerase has exonuclease activity, e.g. 5' and/or 3' exonuclease activity.

In preparing the reaction mixture for the RCA step of the subject methods, the various constituent components may be combined in any convenient order. For example, all of the various constituent components may be combined at the same time to produce the reaction mixture. In some embodiments the polymerase and other reagents for the RCA step (e.g. a RCA reaction mix) may be added during (e.g. at the same time) as the introduction of permissive conditions (e.g. addition of an initiator oligonucleotide). In other embodiments the RCA reaction mix is added after a washing step (e.g. when an embodiment with an immobilised activator target or separate activator molecule is used), or when an immobilised probe has been released from a solid support upon activation etc., or after a probe has been activated.

Usually the reaction mixture for RCA will include four different types of dNTPs corresponding to the four naturally occurring bases present, i.e. dATP, dTTP, dCTP and dGTP. In the subject methods, each dNTP will typically be present in an amount ranging from about 10 to 5000 μM, usually from about 20 to 1000 μM.

The amplified products of an RCA reaction may be detected using any convenient protocol, where the particular protocol employed may detect the RCA products non-specifically or specifically, as described in greater detail below. For instance, the RCA product may be detected directly, e.g. the concatemer may be cleaved to generate monomers which may be detect using gel electrophoresis or by hybridizing labelled detection nucleotides that hybridize to the reporter domain in the RCA product. Alternatively, the RCA product may be detected indirectly, e.g. the product may be amplified by PCR and the amplification products may be detected.

Representative non-specific detection protocols of interest include protocols that employ signal producing systems that selectively detect single or double stranded DNA products, e.g., via intercalation. Representative detectable molecules that find use in such embodiments include fluorescent nucleic acid stains, such as phenanthridinium dyes, including monomers or homo- or heterodimers thereof, that give an enhanced fluorescence when complexed with nucleic acids. Examples of phenanthridinium dyes include ethidium homodimer, ethidium bromide, propidium iodide, and other alkyl-substituted phenanthridinium dyes. In another embodiment of the invention, the nucleic acid stain is or incorporates an acridine dye, or a homo or heterodimer thereof, such as acridine orange, acridine homodimer, ethidiumacridine heterodimer, or 9-amino-6-chloro-2-methoxyacridine. In yet another embodiment of the invention, the nucleic acid stain is an indole or imidazole dye, such as HOECHST™ 33258, HOECHST™ 33342, HOECHST™ 34580 (BIOPROBES 34, Molecular Probes, Inc. Eugene, Oreg., (May 2000)) DAPI (4',6-diamidino-2- phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating Tb3+ and Eu3+, for example). In certain embodiments of the invention, the nucleic acid stain is a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO®, BOBO™, POPO™, YOYO®, TO-PRO®, BO-PRO™, PO-PRO™, and YO-PRO® from Molecular Probes, Inc., Eugene, Oreg. Oreg. Any of the dyes described in U.S. Pat. No. 5,436,134 to Haugland et al. (1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR® Green, EvaGreen, SYTO®, SYTOX®, PICOGREEN®, OLIGREEN®, and RIBOGREEN® from Molecular Probes, Inc., Eugene, Oreg. In yet other embodiments of the invention, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO®, SYTOX®, JOJO™, JO-PRO™, LOLO™, LO-PRO™ from Molecular Probes, Inc., Eugene, Oreg.

In yet other embodiments, a signal producing system that is specific for the amplification product, as opposed to nucleic acid molecules in general, may be employed to detect the amplification. In these embodiments, the signal producing system may include a detection probe that specifically binds to a sequence found in the amplification product (i.e. a reporter domain sequence), where the detection probe may be labelled with a directly or indirectly detectable label. A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, where directly detectable labels of interest include, but are not limited to: fluorescent labels, radioisotopic labels, chemiluminescent labels, and the like. In many embodiments, the label is a fluorescent label, where the labelling reagent employed in such embodiments is a fluorescently tagged nucleotide(s), e.g. fluorescently tagged CTP (such as Cy3- CTP, Cy5-CTP) etc. Fluorescent moieties which may be used to tag nucleotides for producing labelled probe nucleic acids (i.e. detection probes) include, but are not limited to: fluorescein, the cyanine dyes, such as Cy3, Cy5, Alexa 555, BODIPY® 630/650, and the like. Other labels, such as those described above, may also be employed as are known in the art.

In certain embodiments, the specifically labelled detection probes are labelled with "energy transfer" labels. As used herein, "energy transfer" refers to the process by which the fluorescence emission of a fluorescent group is altered by a fluorescence-modifying group. Energy transfer labels are well known in the art, and such labelled oligonucleotide probes include the TaqMan® type probes, as described in U.S. Pat. No. 6,248,526, the disclosure of which is herein incorporated by reference (as well as Held et al., Genome Res. (1996) 6:986-994; Holland et al., Proc. Natl Acad. Sci. USA (1991) 88:7276-7280; and Lee et al., Nuc. Acids Res. (1993) 21:3761-3766). Further examples of detection probes include: Scorpion probes (as described in Whitcombe et al., Nature Biotechnology (1999) 17:804-807; U.S. Pat. No. 6,326,145, the disclosure of which is herein incorporated by reference), Sunrise probes (as described in Nazarenko et al., Nuc. Acids Res. (1997) 25:2516-2521; U.S. Pat. No. 6,117, 635, the disclosure of which is herein incorporated by reference), Molecular Beacons (Tyagi et al., Nature Biotechnology (1996) 14:303-308; U.S. Pat. No. 5,989,823, the disclosure of which is incorporated herein by reference), and conformationally assisted probes (as described in provisional application Ser. No. 60/138,376, the disclosure of which is herein incorporated by reference).

Thus, determining the presence of the RCA product may be achieved using any convenient protocol in order to detect the target nucleic acid (or target analyte) in the sample. In other words, the reaction mixture is screened etc. (i.e., assayed, assessed, evaluated, tested, etc.) for the presence of any resultant RCA products in order to detect the presence of the target nucleic acid molecule in the sample being assayed. The particular detection protocol may vary depending on the sensitivity desired and the application in which the method is being practiced. In certain embodiments, the RCA product may be directly detected without any further amplification, while in other embodiments the detection protocol may include an amplification component, in which the copy number of the RCA product is increased or the RCA product is used as a template for further RCA reactions, e.g., to enhance sensitivity of the particular assay.

The next step in the subject methods is signal detection from the labelled RCA or amplification products of interest, where signal detection may vary depending on the particular signal producing system employed. In certain embodiments, merely the presence or absence of detectable signal, e.g., fluorescence, is determined and used in the subject assays, e.g., to determine or identify the presence or absence of the target nucleic acid molecule. Depending on the particular label employed, detection of a signal may indicate the presence or absence of the target nucleic acid molecule.

In those embodiments where the signal producing system is a fluorescent signal producing system, signal detection typically includes detecting a change in a fluorescent signal from the reaction mixture to obtain an assay result. In other words, any modulation in the fluorescent signal generated by the reaction mixture is assessed. The change may be an increase or decrease in fluorescence, depending on the nature of the label employed, but in certain embodiments is an increase in fluorescence. The sample may be screened for an increase in fluorescence using any convenient means, e.g., a suitable fluorimeter, such as a thermostable-cuvette or plate-reader fluorimeter, or where the sample is a tissue sample on a microscope slide, fluorescence may be detected using a fluorescence microscope. Fluorescence is suitably monitored using a known fluorimeter. The signals from these devices, for instance in the form of photo-multiplier voltages, are sent to a data processor board and converted into a spectrum associated with each sample tube. Multiple tubes, for example 96 tubes, can be assessed at the same time. Thus, in some embodiments multiple analytes may be detected in parallel, whereas in other embodiments multiple analytes may be detected sequentially, e.g. one analyte at a time or one group of analytes at a time.

Kits comprising a nucleic acid probe of the present invention, and suitable for performing the methods described herein, are also provided. Said kits may comprise:

a) a nucleic acid probe as defined herein; and one or more further components selected from:
b) a polymerase enzyme for rolling circle amplification;
c) a primer for RCA;
d) a separate activator molecule;
e) one or more reagents for performing an RCA reaction;
f) means for detecting an RCA product; and
g) an initiator oligonucleotide, or other means for introducing permissive conditions to allow the target molecule or separate activator molecule to bind to the probe.

The subject probes and methods may be used to screen a sample for the presence or absence of one or more target analytes in a sample. As indicated above, the invention provides probes and methods for detecting the presence or quantifying the amount of one or more target analytes in a sample. The subject probes and methods can be employed to detect the presence of one or more target analytes in a variety of different types of samples, including complex samples having large amounts of non-target entities, where the probe of the invention allows for superior detection of the target analyte(s) over equivalent methods that utilise RCA probes. As such, the subject probes provide methods that are highly sensitive for detecting one or more target analytes in a simple or complex sample. The sample that is assayed in the subject methods is, in many embodiments, from a physiological source, as discussed in more detail above.

It will be evident from the description above and the representative examples described below that the probes and methods of the invention have numerous advantages over existing methods. Advantageously, the use of probes that provide a pre-formed RCA template renders the probes and methods of the invention particularly useful for the simultaneous detection of multiple analytes in a sample, i.e. multiplex assays. Furthermore, each probe may result in a RCA product that is unique, which allows multiple analytes to be detected in parallel. Alternatively, for assays used to detect a large number of analytes, it may be useful to detect (e.g. visualise) the RCA products sequentially, e.g. one at a time or one group at a time. The probe of the invention enables other reagents to be added to the assay at the same time as the probes. As the RCA nucleic acid components provided by the probes cannot initiate a RCA reaction until the probe bound to its target nucleic acid molecule, thereby minimising RCA products that arise from non-specific interactions and/or false priming of the an RCA reaction. Reducing the number of steps in the assay minimises potential errors and renders the protocol more suitable for automation.

BRIEF DESCRIPTION OF THE DRAWINGS

The invention will be further described with reference to the following non-limiting Examples with reference to the following drawings in which:

FIG. 5 shows a gel to visualise the nucleic acid probes.

FIG. 10 shows the signal generated using a nucleic acid probe of the present invention using the nucleic acid probes having the sequences shown in FIGS. 2 ('design 1') and 4 ('design 2') in the detection of an RCA product. Top line—detection of an RCA product generated from a circular template strand hybridised to a primer using a nucleic acid probe. Middle line—detection of an RCA product generated from a circular template strand hybridised to a primer, without using a nucleic acid probe. A negative control (no circular template strand) is also shown (bottom line). FIG. 10A—detection using 'design 1'. FIG. 10B—detection using 'design 2'.

FIG. 12 shows that second-generation RCA products may be detected by flow cytometry. FIG. 12A: RCPs were stained with detection oligos containing TEXAS RED® fluorophores. Different concentrations of circles (first generation of RCA) were amplified further with 5 nM nucleic acid probes (design 2). The background from the nucleic acid probes is seen in the upper left graph. A peak (or rather bulge) of very big objects is appearing when increasing the amount of circles (first generation RCA). FIG. 12B The number of events in the bar graph is the number of counts in the shoulder beyond the negative control peak in the flow cytometry assay, representing large objects (mostly super-sized RCPs).

FIG. 14 shows that the nucleic acid probes may be used in a proximity-based detection assay. FIG. 14A shows a putative illustration of a solid phase protein detection setup using the nucleic acid probe for proximity dependent protein detection. Activation of the proximity binding partner for the nucleic acid probe can be achieved by unfolding the activator molecule, e.g. in this instance by using UNG. FIG. 14B shows that a detectable signal may be generated when the nucleic acids indicated in FIG. 14A (a nucleic acid probe and activatable target nucleic acid molecule) are incubated. Addition of 1 nM activator without UNG did not increase the signal. Addition of 10 nM activator without UNG did only slightly increase the signal. A large increase in amplification rate was seen for both 1 and 10 nM activator when UNG was added to the RCA mix. This demonstrates that the activation of nucleic acid probe is highly dependent upon the UNG de-protection of the activator molecule.

FIG. 15 shows microscopy images indicating that a target nucleic acid immobilised on a solid surface may be detectable by the binding of a nucleic acid probe and a separate activator molecule (which is the activator for the probe and may be activatable by UNG). FIG. 15B shows that a compaction oligonucleotide can improve detection of a RCA product and quantification of target analyte in the sample. Left panels: 100 pM target. Right panels: 50 pM target. Top panels: detection of a RCA product in the presence of a compaction oligonucleotide. Bottom panels: detection of a RCA product in the absence of a compaction oligonucleotide.

FIG. 18 shows the in situ detection of a protein-protein complex using a pair of proximity probes conjugated to a nucleic acid probe and an activator molecule. FIG. 18C(ii): Anti-β-catenin used, anti-E-cadherin not used. The pair of proximity probes was added to each sample. Detection of the protein-protein complex in resulted in formation of a RCA product, indicated by well-defined fluorescent spots in FIG. 18B (shown by arrows).

FIG. 22 shows a solid phase detection design.

FIG. 23 shows a 'double recognition' design for a set of nucleic acid molecules for the detection of a target nucleic acid molecule.

FIG. 26 shows a nucleic acid probe comprising two second protector strands in a 'double recognition' design for a set of nucleic acid molecules for the detection of a target nucleic acid molecule. In this design, the activator molecule comprises a hairpin structure and a binding site for the target nucleic acid molecule in its 5' end.

EXAMPLES

Example 1

Production of Nucleic Acid Probes

Figure 1:
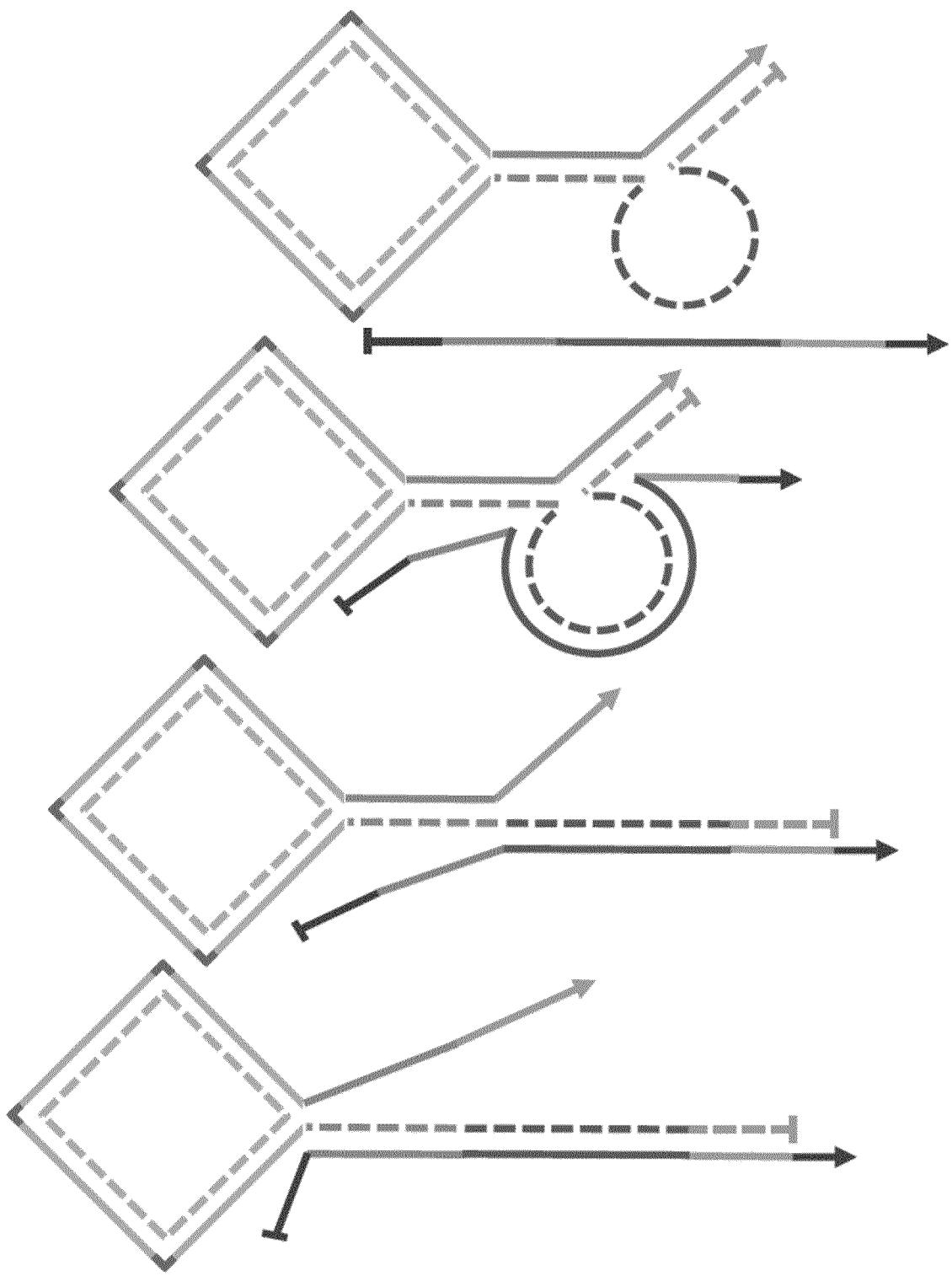
FIG. 1 shows a schematic diagram for a probe (design 1') comprising a stem-loop structure and a duplex region, in which the duplex region contains a bulge comprising an at least portion of the target binding site. Binding of the target nucleic acid molecule to the probe unfolds the duplex region and leads to probe activation. Following activation of the probe, the single-stranded 3' region of the probe may be degraded e.g. by a 3' exonuclease enzyme to provide a primer for rolling circle amplification.
Figure 2:
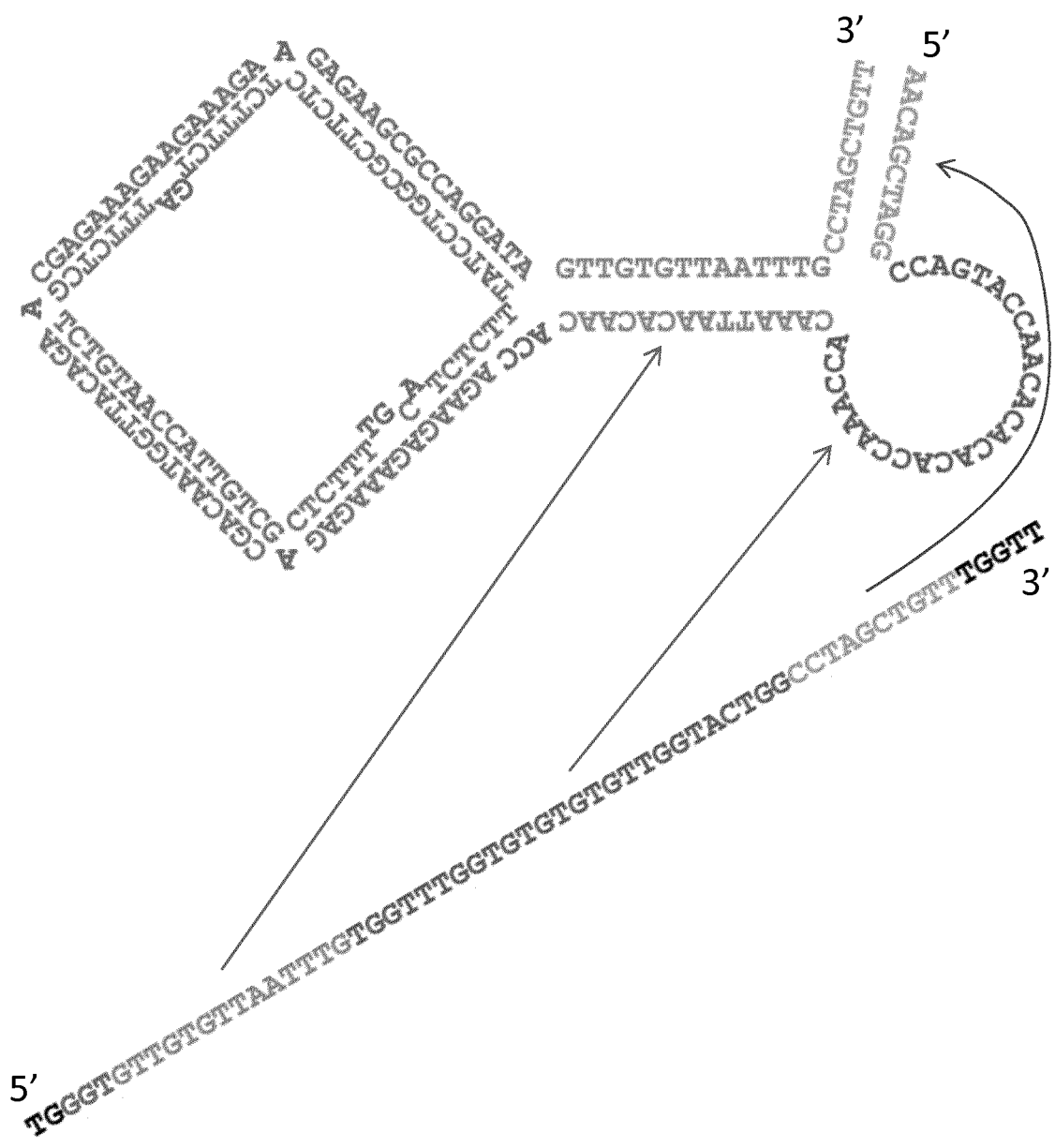
FIG. 2 shows a probe comprising exemplary sequences (SEQ ID NOs: 1 and 3) for the probe design shown FIG. 1, for detecting a target nucleic acid provided in SEQ ID NO: 4.
Figure 3:
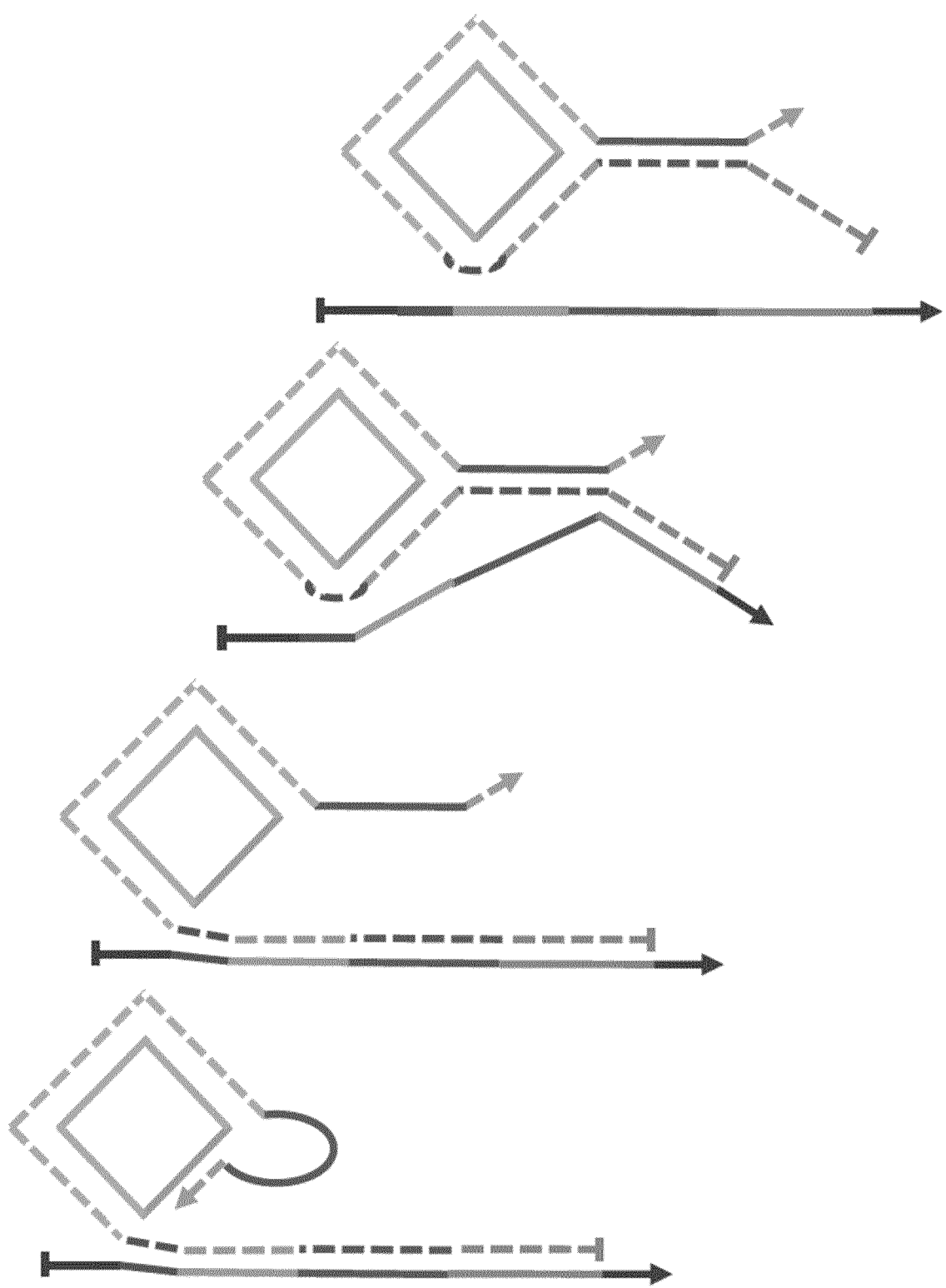
FIG. 3 shows a schematic diagram for an alternative probe ('design 2') comprising a stem-loop structure and a duplex region, in which the probe comprises a single-stranded region at its 5' end which serves as at least a portion of the a target binding site, and a single-stranded region at its 3' end which is able to bind to the circular template nucleic acid molecule following probe activation to provide a primer for RCA.
Figure 4:
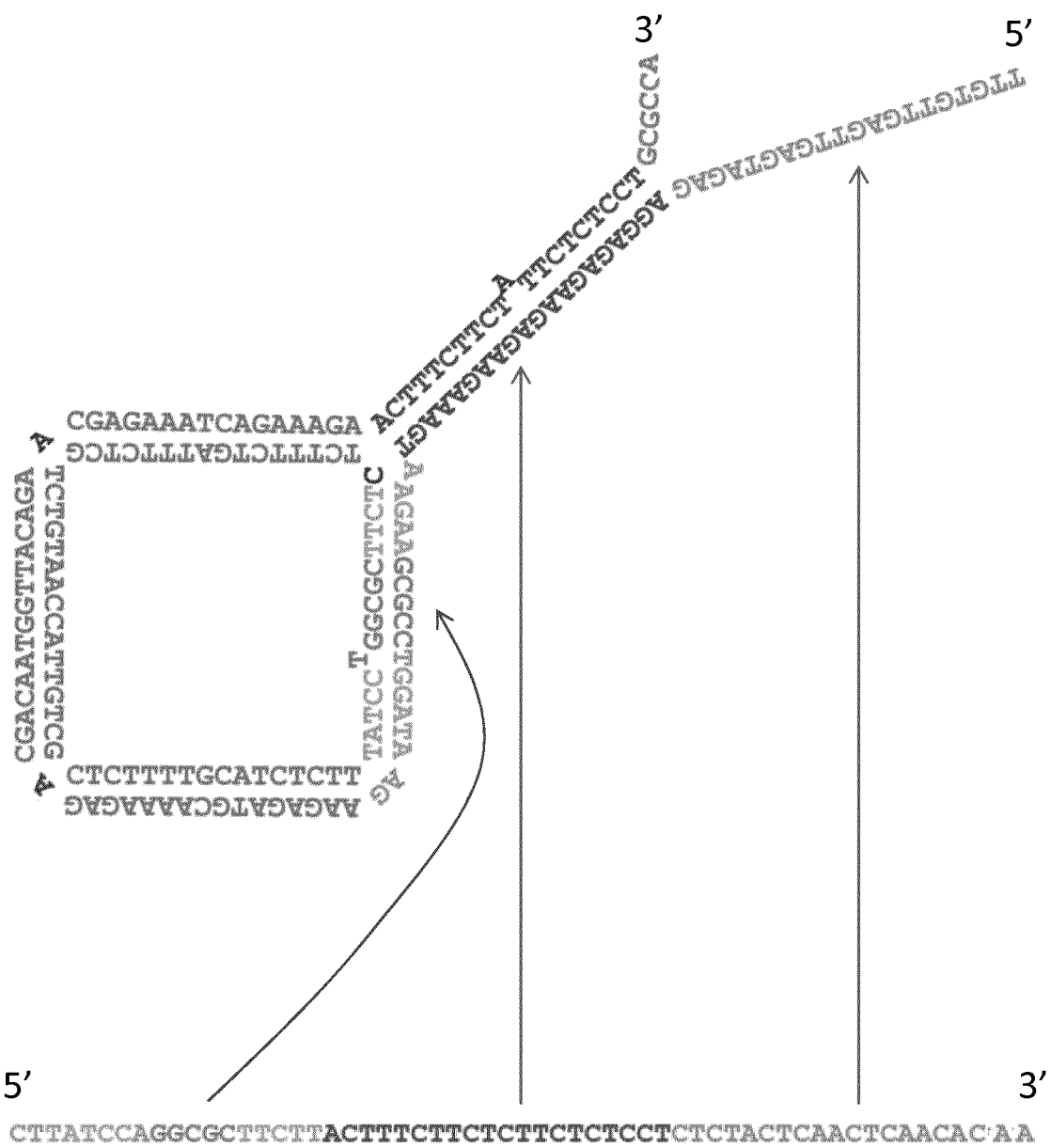
FIG. 4 shows a probe comprising exemplary sequences (SEQ ID NOs: 2 and 3) for the representation shown FIG. 5, for detecting a target nucleic acid provided in SEQ ID NO: 5.
Figure 5A:
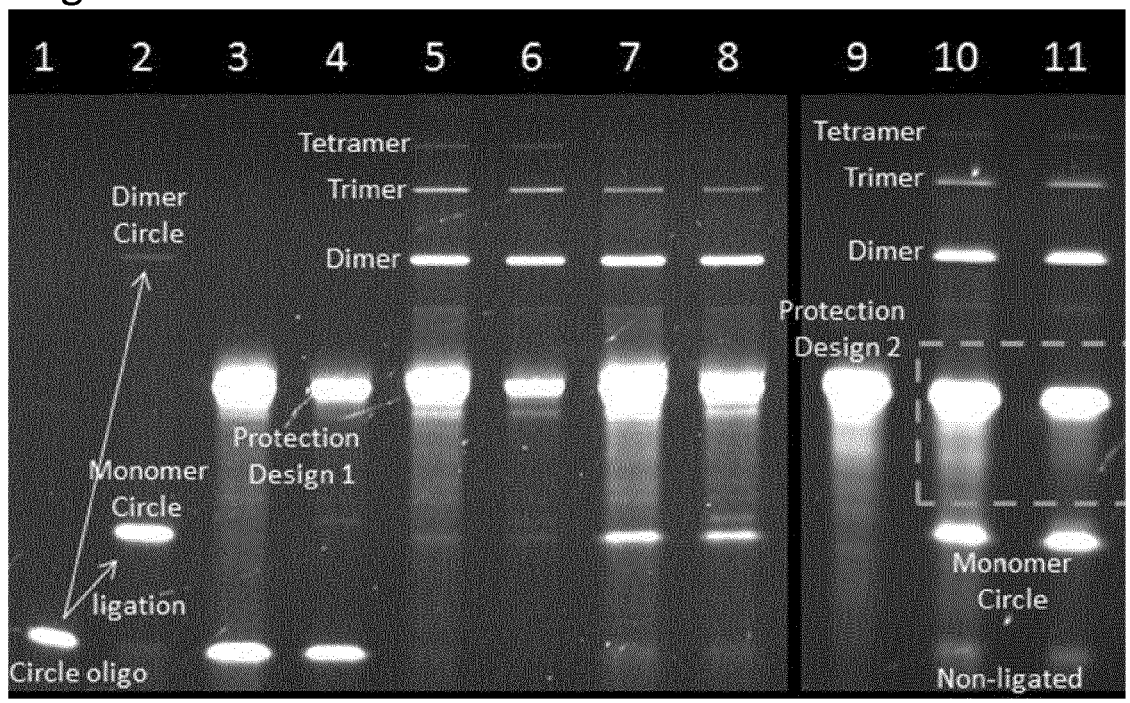
FIG. 5A—Lane 1: Circle strand and small ligation template (not seen). Lane 2: Ligated circle strand and small ligation template (not seen). Lane 3: Circle strand and protector strand (design 1). Lane 4: Circle strand and protector strand (design 1) after capture of excess protector strand using immobilised capture oligonucleotide. Lane 5: Ligated circle strand and protector strand (design 1) (ligation at higher conc). Lane 6: Ligated circle strand and protector strand (design 1) after capture of excess protector strand using immobilised capture oligonucleotide (ligation at higher conc). Lane 7: Ligated circle strand and protector strand (design 1) (ligation at lower conc). Lane 8: Ligated circle strand and protector strand (design 1) after capture of excess protector strand using immobilised capture oligonucleotide (ligation at lower conc). Lane 9: Protector strand 2. Lane 10: Ligated circle strand and protector strand (design 2) (ligation at higher conc). Lane 11: Ligated circle strand and protector strand (design 2) after capture of excess protector strand using immobilised capture oligonucleotide (ligation at higher conc).

Nucleic acid probes were pre-fabricated by ligation of the circular template strand inside the protector strand with the protector strand acting as template for the ligation (guidance for the ligase). This was performed with a 2-fold excess of the protector strand, and the excess was subsequently removed by use of a biotinylated capture oligo and magnetic beads coated with streptavidin. When the fabrication results were analysed with denaturing PAGE it was found that a fraction of the formed reporters were not monomeric (dimer, trimer and tetramer bands formed in lanes 5-8 and 10 and 11 in FIG. 5).

In lanes 3 and 4 a fraction of the protector strand can be captured by the capture oligo immobilised on magnetic beads, while the circle oligo is barely affected. In lanes 5 and 6 the template strand is ligated (circularised), without and with use of the capture oligo for excess protector strand removal. In this case the ligation was performed at a high concentration (1 µM template strand and 2 µM protector strand).

Figure 5B:
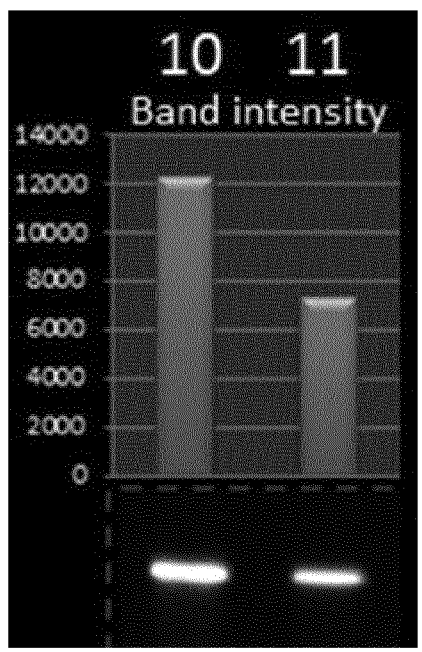
FIG. 5B—Magnified image of lanes 10 and 11 and relative signal generated using production protocols.

Lanes 7 and 8 correspond to lanes 5 and 6, except that the ligation was performed at a lower concentration (100 nM template strand and 200 nM protector strand). It is clearly seen that there is a tendency for smaller ligation products when lowering the ligation concentration In lane 9, 10 and 11 the ligation of 'design 2' nucleic acid probes are seen ligated at high concentration. A smaller degree of multimeric probe is produced than the corresponding reactions for 'design 1'. The bar-graph in FIG. 5B shows the intensities of the bands from 'design 2' protector strand before and after purification. Approximately half of the protector strand is removed.

Figure 6:
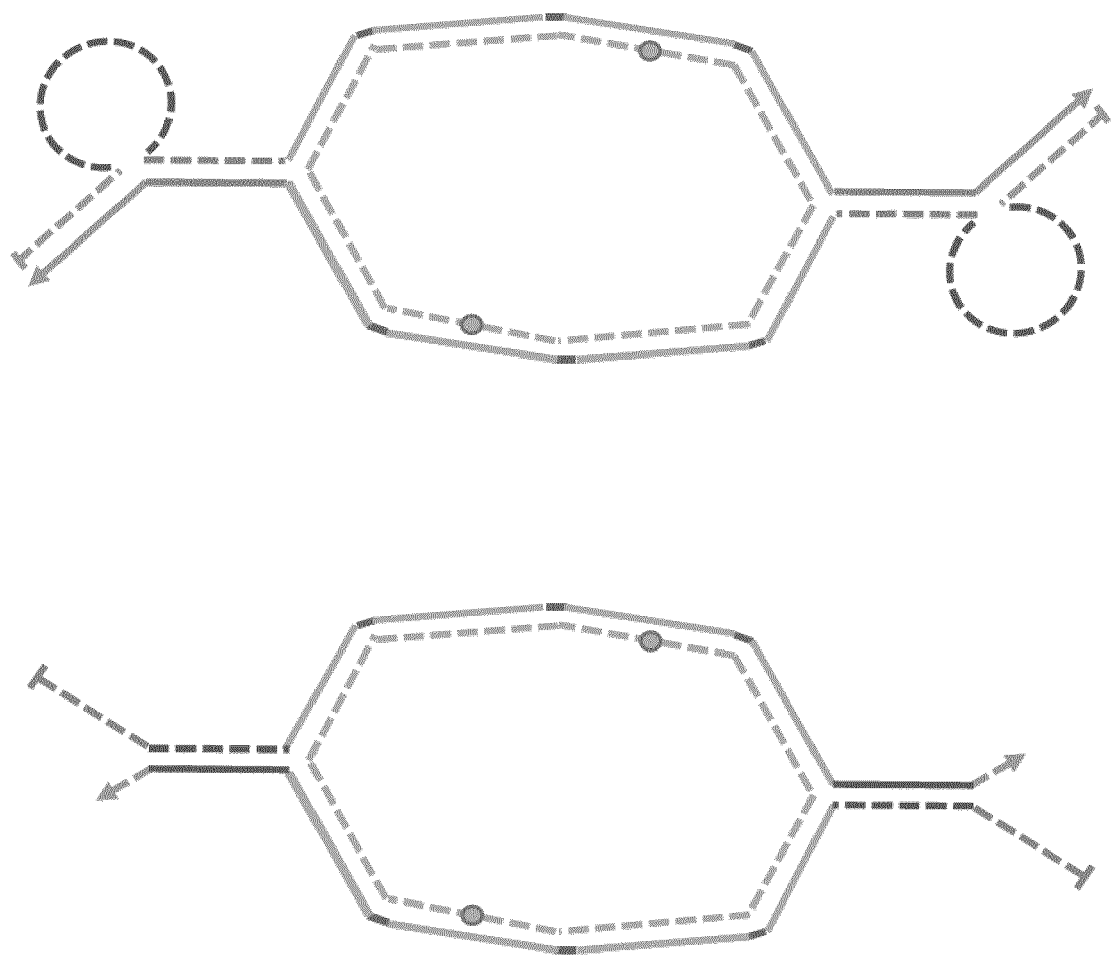
FIG. 6 shows dimeric probes formed as a result of inter-molecular ligation of the circular template strands. Dimeric products formed from the monomeric probes indicated in FIGS. 1 and 3 are shown (designs 1 and 2).

Without wishing to be bound by theory, it is thought that the multimeric products formed during synthesis are represented in FIG. 6. These probes will retain the ability to detect a target nucleic acid molecule in a sample, and will be replicated with the same efficiency as the monomeric probes once generated. However, multimeric versions of the probes can recognise more than one target nucleic acid molecule but only generate a single signal, thus leading to a reduced detection efficiency.

Example 2

Detection of a Target Nucleic Acid Molecule using Nucleic Acid Probes

To initially study the properties of the RCA reporters, molecular beacon probes (TET-fluorophore and BHQ1 quencher) were designed to recognize the rolling circle product (RCP) generated from RCA using the circular template strand as a template.

Figure 7:
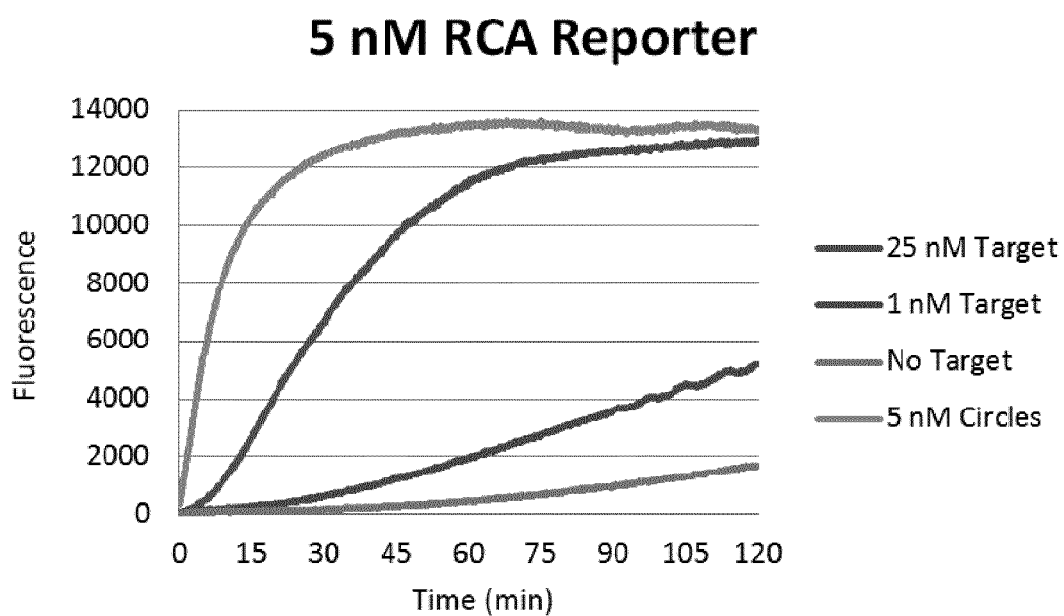
FIG. 7 shows the signal generated for the detection of a target nucleic acid sequence (SEQ ID NO: 4) using a probe design represented in FIGS. 1 and 2 at a series of different target concentrations. 5 nM nucleic acid probe was used to detect target nucleic acids in a sample. The concentration of target nucleic acid molecule were varied and were detectable for concentrations as low as 1 nM. A negative control of no target nucleic acid did not provide an appreciable signal after 120 minutes. A positive control of a circular template nucleic acid molecule (the template strand from the probe (SEQ ID NO: 3) hybridised to a primer was used.
Figure 8:
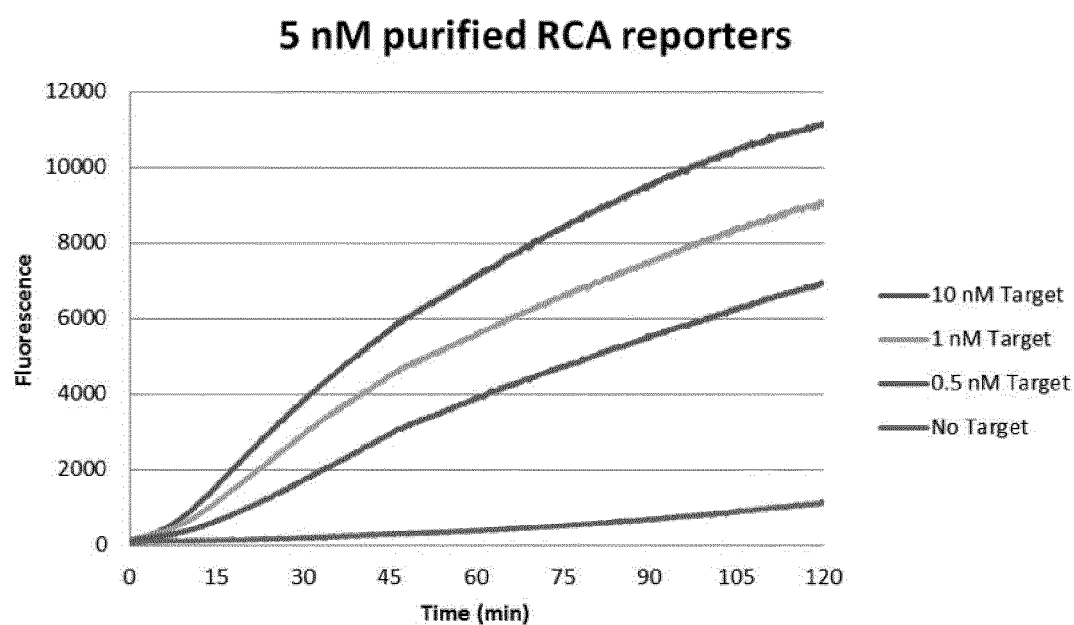
FIG. 8 shows the signal generated for the detection of a target nucleic acid sequence using a probe design represented in FIGS. 1 and 2 at a series of different target concentrations, as above. 5 nM purified nucleic acid probe was used to detect a target nucleic acid sequence. Concentration-dependent signal was detected, and target nucleic acid molecules were detectable at concentrations as low as 0.5 nM. A negative control of no target nucleic acid did not provide an appreciable signal after 120 minutes.
Figure 9:
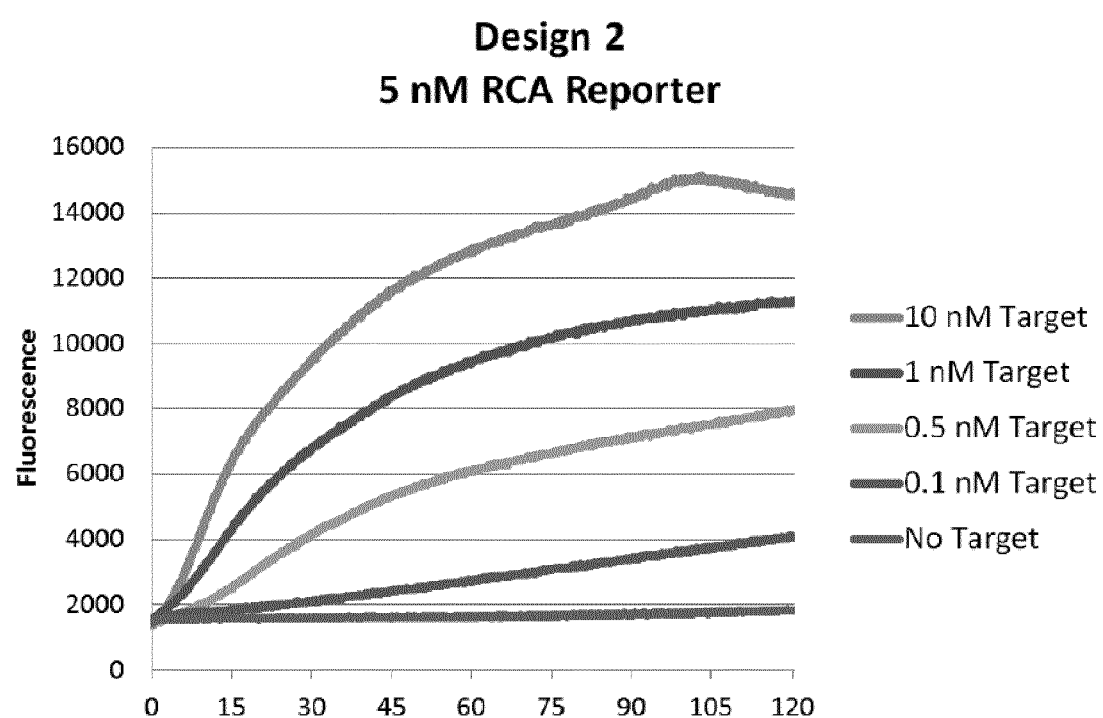
FIG. 9 shows the signal generated for the detection of a target nucleic acid sequence (SEQ ID NO: 5) using a probe design represented in FIGS. 3 and 4 at a series of different target concentrations. 5 nM purified nucleic acid probe was used to detect a target nucleic acid sequence. Concentration-dependent signal was detected, and target nucleic acid molecules were detectable at concentrations as low as 0.1 nM. A negative control of no target nucleic acid did not provide an appreciable signal after 120 minutes.

Amplification was monitored using 5 nM nucleic acid probe seeded with different amounts of target nucleic acid molecule in real time for 120 min at 37° C. A clear dose response was seen for both 'design 1' (FIGS. 7 and 8) and 'design 2' (FIG. 9) probes. Slightly lower background was observed for 'design 2' probes. The nucleic acid probes were activatable in the presence of 100 pM target nucleic acid molecule (design 2), and signal can be clearly detected over the background amplification from 5 nM probes.

Example 3

Detection of an RCA Product using Nucleic Acid Probes

One nucleic acid probe can in theory be activated for each copy of an original template nucleic acid molecule that is present in a concatemeric RCA product. Detection of an RCA product thus can give rise to second generation products when detected using nucleic acid probes. Amplification starts immediately upon probe activation, which can occur once amplification of the first template takes place. Without any additional steps, except for the addition of the nucleic acid probes to the initial RCA mix, a second generation 'super-RCA' product may be generated.

Real-time monitoring of the amplification was performed for both the 'design 1' (FIG. 10A) and 'design 2' (FIG. 10B) probes over 90 minutes at 37° C. with molecular beacon probes targeting both the first and the second generation RCA products. Incubating 5 nM nucleic acid probe in the absence of the first RCA product (bottom line) generates no signal increase. Incubating 100 pM of template for the first generation RCA generates a small increase in signal (middle line). The combination of 100 pM template (first generation RCA) with 5 nM nucleic acid probe gives rise to a second generation 'super-RCA' product, which drastically increases the amplification rate and hence detection. Thus the signal generated in a rolling circle amplification reaction can be amplified further simply by adding nucleic acid probes as described herein.

Figure 11:
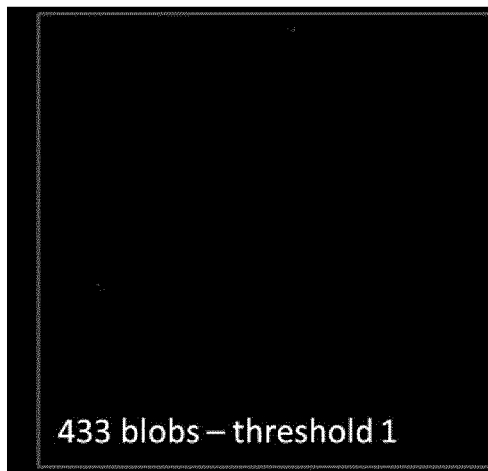
FIG. 11 shows microscopy images showing the RCA products formed on detection of a first RCA product remain localised. RCA products were grown in solution and then added and allowed to settle down on positively charged microscopy slides. DNA was stained with SYBR Gold. "Template" in this case refers to the circular RCA template used to generate the first generation RCA product. The RCA was performed for 90 minutes at 37° C. with and without nucleic acid probes (5 nM) and a first circular template for the first RCA reaction (circle with primer, 10 pM). Top left: No template, no probe. Top right: Template, no probe. Bottom left: No template, probe. Bottom right: Template, probe. The integrity of the RCPs was very good (lower right image). The number of blobs (RCPs) were counted with imageJ function find intensity maxima. Different thresholds were used for regular size RCPs (threshold 1) and the second generation RCPs (threshold 140). High threshold means that the intensity maxima has to be greater to be counted. In this way the same number of events were counted 10 pM of regular sized as second generation (right images). The corresponding background counts were much lower for the super-sized RCPs (right images) resulting in improved signal to noise when using nucleic acid probes to create super-sized RCPs. These experiments utilise probes with 'design 2'. The images were all taken with 20× objective, 600 ms exposure time and in the GFP channel.
Figure 11:
Figure 11:
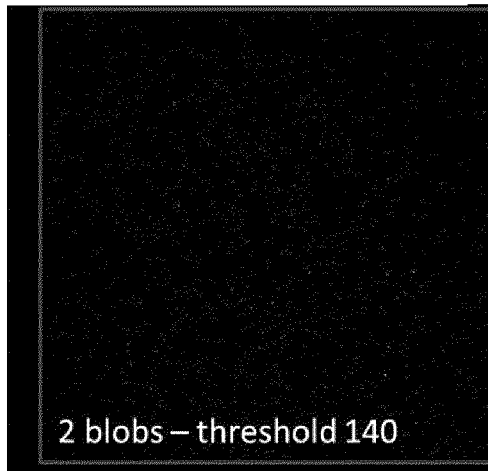
Figure 11:
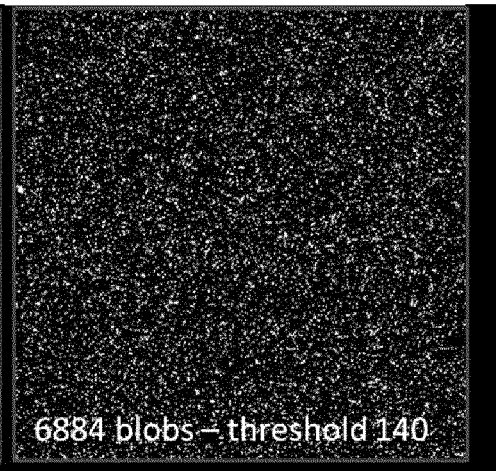

The integrity of the second generation 'super-RCA' DNA product formed was found to be maintained when stained with SYBR gold and visualised with fluorescence microscopy (FIG. 11). RCA products were grown in solution and then added and allowed to settle down on positively charged microscopy slides. DNA was stained with SYBR Gold. The RCA was performed for 90 minutes at 37° C. with and without the nucleic acid probes (5 nM) and first RCA template (circle with primer, 10 pM). The integrity of the second generation RCA product was very good (lower right image). The number of blobs (RCPs) was counted with imageJ function find intensity maxima. Different thresholds were used for first generation RCPs (threshold 1) and the second generation RCPs (threshold 140). The corresponding background counts were much lower for the second generation RCPs (bottom left image) resulting in improved signal to noise when using nucleic acid probes to create second generation RCPs. These images are generated using the 'design 2' probe. The images were all taken with 20× objective, 600 ms exposure time and in the GFP channel.

Second generation RCPs were also detected by flow cytometry (FIG. 12). Second generation RCPs were stained with detection oligonucleotides containing TEXAS RED® fluorophores. Different concentrations of templates for a first generation of RCA were amplified further with 5 nM nucleic acid probes (design 2'). The background from the nucleic acid probes is seen in the upper left graph of FIG. 12A. A peak to the right of the negative control peak appears when the concentration of template for the first RCA reaction is increased (FIG. 12A, top right, bottom left and bottom right). The number of events in the bar graph in FIG. 12B is the number of counts in the peak, indicating the presence of second generation (super-RCA) products.

Example 4

Assessing Target Specificity of the Nucleic Acid Probes

Figure 13:
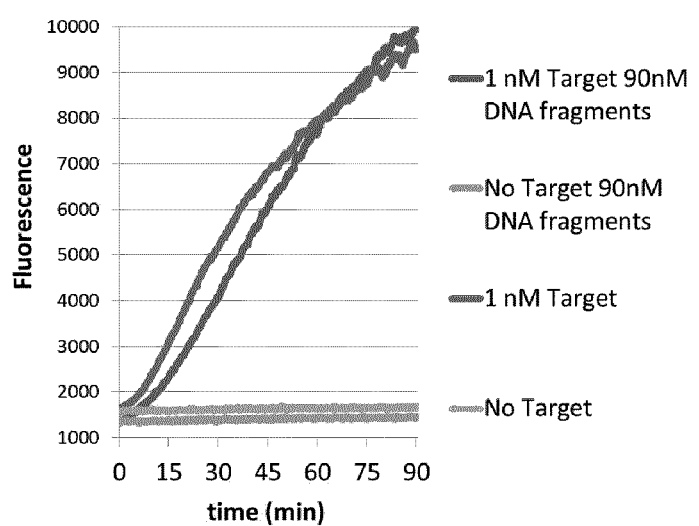
FIG. 13 shows that non-target nucleic acid has no effect on detection efficiency, or on activation of the probe. Detection of 1 nM target was performed in the presence and absence of 90 nM random DNA fragments of approximately the size of the correct target. No clear difference in signal or background was seen when adding the extra random DNA fragments. The amplification was monitored with molecular beacon probes for 90 minutes at 37° C.

A very simple interference experiment was performed using 90 nM random DNA fragments mixed with 1 nM target nucleic acid molecule for the nucleic acid probe (FIG. 13). Detection was performed in the presence and absence of the random DNA fragments. In the presence of the target nucleic acid, sensitivity—the ability of the nucleic acid probes to detect the target nucleic acid molecule was not affected by the random DNA fragments. In the absence of the target nucleic acid, selectivity—the ability of the nucleic acid probes to not be activated by oligonucleotides present in the sample, was not affected by the random DNA fragments.

Example 5

Proximity-Based Detection of a Target Analyte

Figure 17:
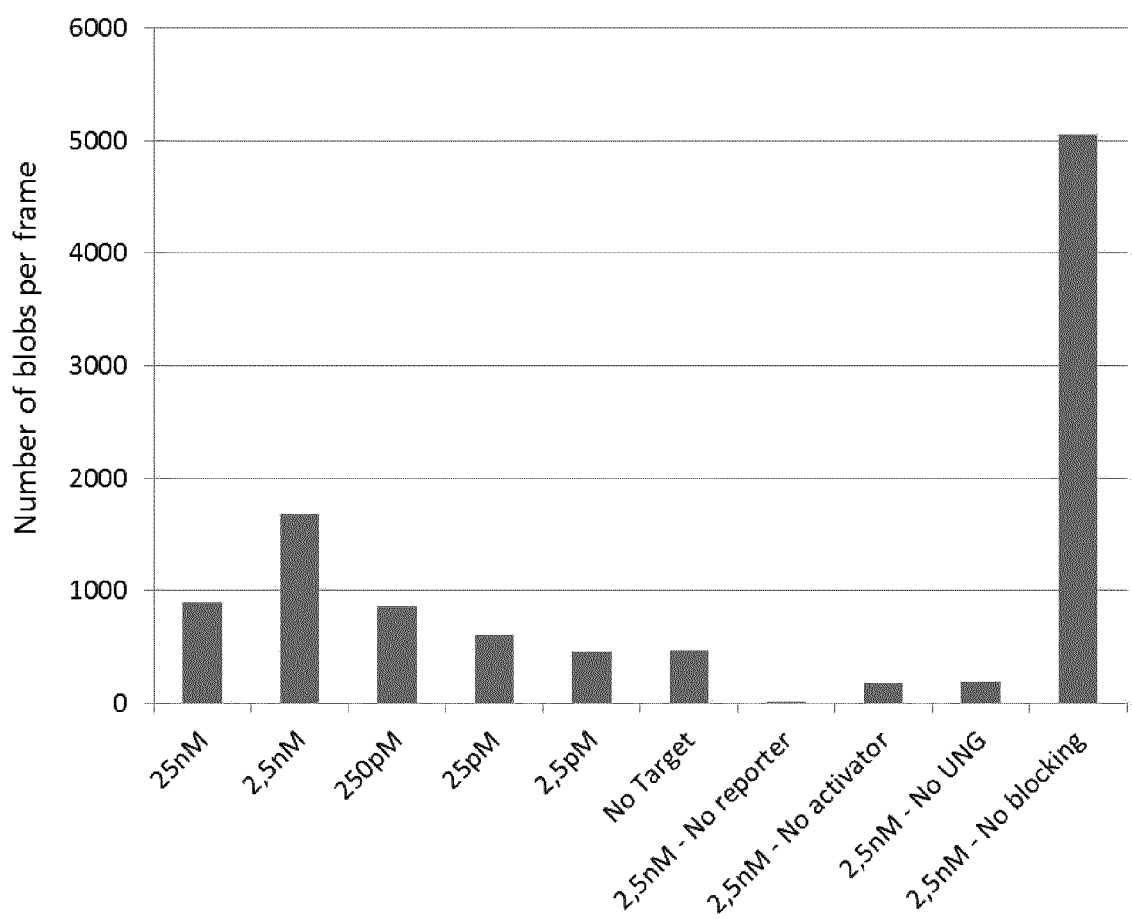
FIG. 17 shows quantified results of a solution-based detection assay. A mouse anti-human IL-6 antibody was used as a target analyte, and a nucleic acid probe and activator were conjugated to fractions of an anti-mouse polyclonal antibody. A high signal is seen when no blocking oligo is used (non-proximity background). A low background is seen when no activator is used and when no UNG is used (false activation of nucleic acid probes). A relatively high background is seen for the sample without target (signals generated through non-proximity activation). A signal increase can be seen for increasing amounts of target protein except the highest concentration. Without wishing to be bound by theory, it is thought this may be due to the target molecule being present at a saturating concentration at this point.
Figure 18A:
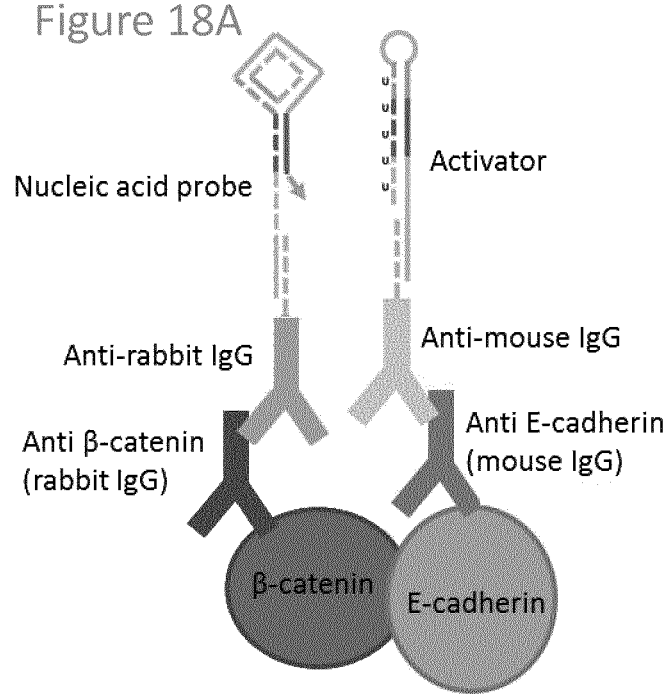
FIG. 18A: schematic diagram of the detection reagents.

Proteins may be detected using the nucleic acid probes described herein in a proximity-dependent manner, by conjugating the nucleic acid probe and an activator nucleotide to a pair of proximity probes as shown in FIG. 14A. The proximity-based activation of the nucleic acid probe was assessed in a series of proof of concept experiments (FIGS. 15-17), and shown to be effective in the detection of a protein complex on the surface of A549 cells in an in situ detection assay (FIG. 18).

The activator nucleotide (the target nucleic acid molecule for the nucleic acid probe used in a proximity-dependent detection assay) may be modified to be protected, i.e. that it cannot activate the nucleic acid probe until it is, itself, activated. One such way of doing this is using a hairpin structure, in which the strand complementary to the target nucleic acid sequence contains Uracil residues instead of Thymine. A Uracil-DNA glycosylate (UNG) can then de-protect the target nucleic acid and allow it to activate the nucleic acid probe (bound in proximity). The nucleic acid probe is attached to a first antibody forming a first proximity probe and the target nucleic acid molecule attached to a second antibody forming a second proximity probe (FIG. 14A).

A first experiment was to investigate whether the nucleic acid probe could be activated with UNG treated activator molecules (FIG. 14B). The nucleic acid probe (5 nM) was incubated with different concentration of the activator molecules and an RCA mix with and without UNG. The amplification was monitored at 37° C. for 3 hours. Some background amplification from the nucleic acid probes was seen without activator present. Addition of 1 nM activator without UNG did not increase the signal above background. Addition of 10 nM activator without UNG resulted in a slight increase in signal. A large increase in amplification rate was seen for both 1 and 10 nM activator when UNG was added to the RCA mix, demonstrating that the activation of nucleic acid probes using a target nucleic acid molecule that can be selectively unfolded is highly dependent on the de-protection of the activator molecule, and thus that activation is specific and controllable.

Figure 15A:
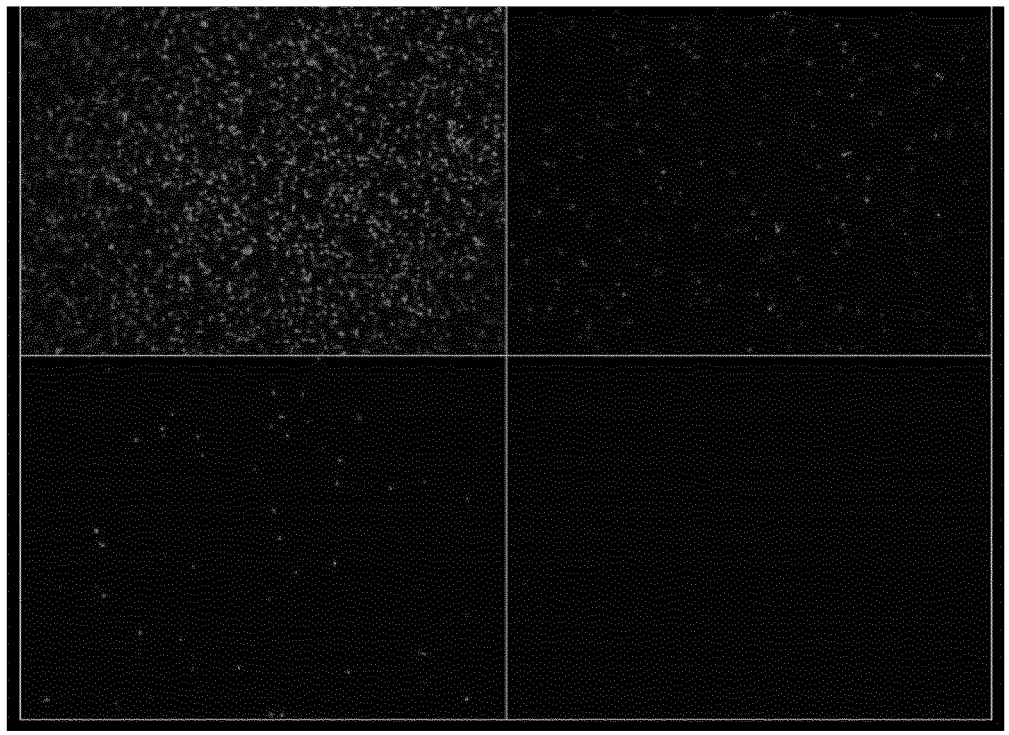
FIG. 15A shows that the nucleic acid probe may be activated by a separate activator binding to a target nucleic acid. Top left: 100 pM target. Top right: 10 pM target. Bottom left: 100 pM target, no UNG. Bottom right: no target. This indicates that solid-phase detection of a target analyte using proximity probes is activator (target nucleic acid) dependent.
Figure 15A:
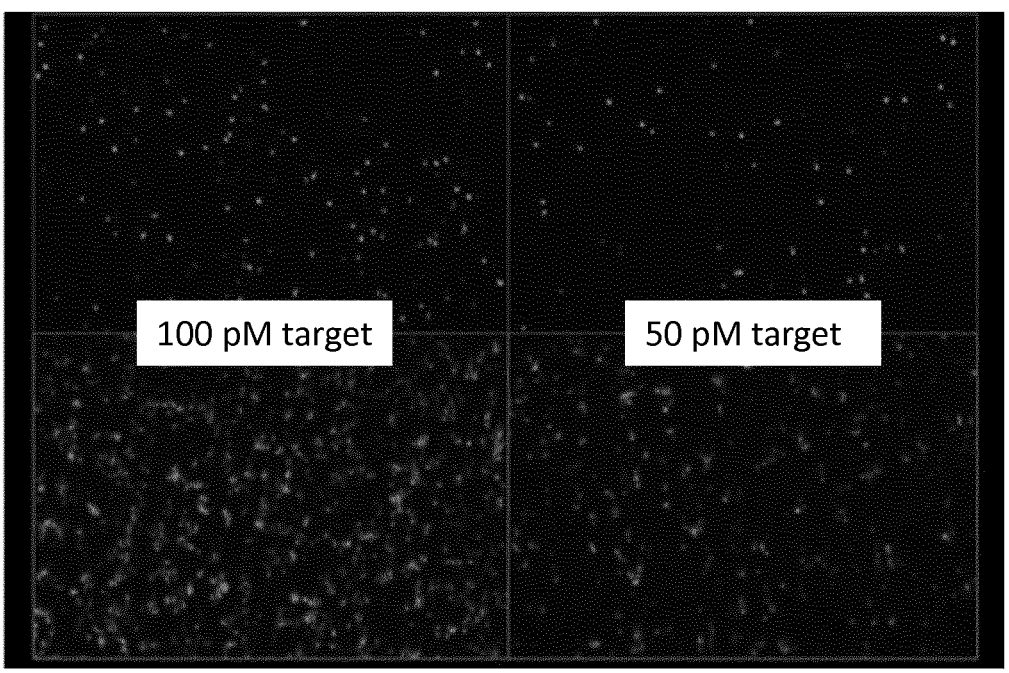

A model system was prepared to investigate whether proximity-based detection could be performed for a solid phase detection assay (FIG. 15). In this model system a biotinylated nucleic acid hybridisation target with sequences capable of hybridising to the nucleic acid probe and the activator molecule was immobilized to a streptavidin coated surface at two different concentrations (FIG. 15A). Nucleic acid probes (5 nM) and activators (5 nM) were incubated on the surface for 30 min at 37° C. The surface was washed twice with PBS with 0.05% TWEEN®-20 before addition of RCA mix containing TEXAS RED® labelled detection oligos and with or without UNG. The RCA reaction was run for 30 min at 37° C. and then the slides were analysed by fluorescence microscopy. The same exposure time was used for all images. The individual blobs were counted with image) using the intensity maxima function with the same threshold for all images.

A very small background amplification is seen when no hybridization target is used (FIG. 15A, lower right image), approximately 10 times more blobs are seen for 100 pM target (FIG. 15A, upper left) compared to 10 pM target (FIG. 15A, upper right). UNG is essential for signal generation (compare the top left and bottom left images in FIG. 15A).

A close-up image of the blobs in FIG. 15A reveals that they are diffuse and not easily digitally counted. To obtain more distinct blobs a compaction oligo that contains two copies of a complementary sequence to the RCP with a short spacer in between was added to the sample during the RCA reaction (in the RCA mix) (FIG. 15B). Detection of the target was performed at 100 and 50 pM (FIG. 15B left and right conditions) and detection was performed in the presence and absence of the compaction oligo (FIG. 15B top and bottom conditions)

The same model system was used to evaluate the possibility of performing a homogenous (in solution) proximity-based detection assay. 2 μl solution containing 10 nM hybridization target, 50 nM nucleic acid probe and 50 nM activator was incubated 1 h at 37° C. This mix was diluted 10-fold by the addition of 18 ul RCA mix with UNG, molecular beacons and different concentrations of a blocking oligo (protector strand in the absence of the circular template strand) and the amplification was monitored in a qPCR machine at 37° C. (FIG. 16) between 15-30 min. The final concentrations after addition of the RCA mix were: Target 1 nM, nucleic acid probe 5 nM, activator 5 nM and blocking oligo 0-100 nM.

Figure 16:
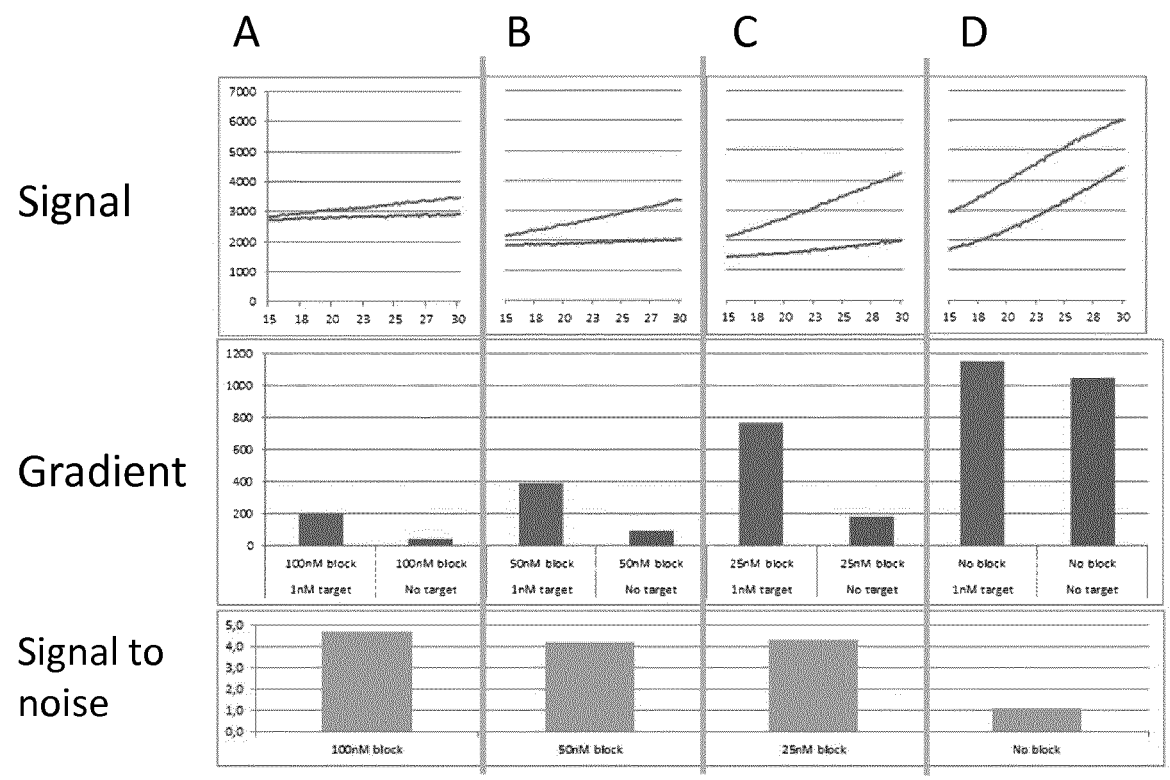
FIG. 16 shows the result from model system for a homogenous version of the proximity dependent protein detection with nucleic acid probes and activators. 1 nM soluble target nucleic acid was targeted using a nucleic acid probe and a separate activator molecule. A-C: Blocking oligonucleotides (protector strand nucleic acids without the circular template strand) added at different concentrations (20:1, 10:1 and 5:1 ratio to nucleic acid probe). D: No blocking oligonucleotide. Top row: Signal generation in the presence and absence of target analyte. Second row: Gradient, or rate of signal generation (dSignal/dT). Third row: signal:noise ratio.

The amplification was monitored in real time at 37° C. (FIG. 16, top row) for samples with and without a target nucleic acid molecule. The gradients were calculated (FIG. 16, middle row) and the signal over background ratio (fold change) was plotted for each concentration of blocking oligo (FIG. 16, bottom row). A 5× excess of blocking oligonucleotide (25 nM) over the nucleic acid probe (5 nM) (FIG. 16C) was sufficient to reach the highest signal to background ratio. Increasing the amount of blocking oligonucleotide further reduced the signal and the background equally and thus did not improve the signal to noise ratio.

A homogeneous proximity-based detection assay was performed using nucleic acid probe and activator attached to antibodies. A batch of polyclonal anti-mouse IgG was split in two aliquots and conjugated with different oligonucleotides (Frw. and Rev.). The nucleic acid probe was hybridised to the Frw. probes and activators to the Rev. probes. A monoclonal mouse anti-human-IL6 antibody was used as the target analyte for the probes. Proximity probes (2.5 nM) were incubated with different concentrations of target at 4° C. overnight. A 25-fold dilution of the RCA mix containing detection oligos, UNG and blocking oligonucleotides (1 nM of protector strand) was made and incubated at 37° C. for 1 h. The samples were applied to slides for evaluation with fluorescence microscopy and the blobs in each image were counted with the CELL PROFILER™ software (FIG. 17). Control samples (no activator; no UNG; no blocking oligonucleotide) were included in the experiment. An increase in signal can be seen for increasing amounts of target protein up to 25 nM target analyte, which produced a lower signal:noise ratio.

Figure 18B:
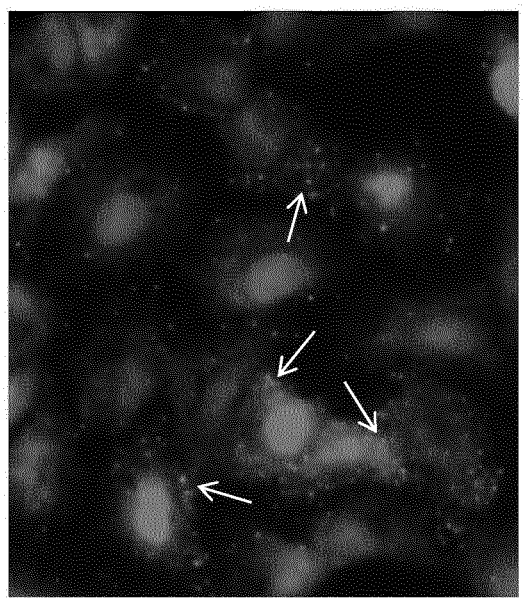
FIG. 18B: Anti-E-cadherin and anti-β-catenin used.
Figure 18C:
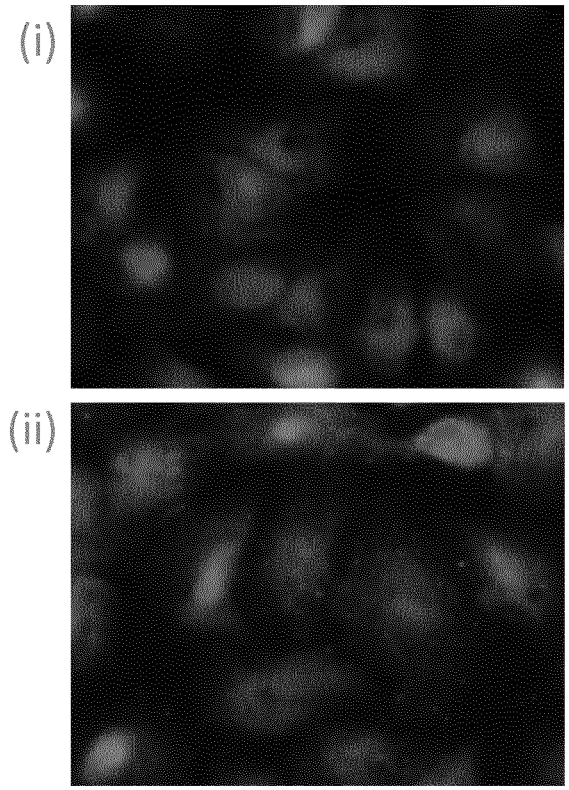
FIG. 18C(i): Anti-E-cadherin used, anti-β-catenin not used.

A proximity-based detection assay was performed to detect a protein-protein complex in situ. Frozen A549 cells fixed on a microscopy slide were thawed and incubated with PBS+0.2% TRITON® X-100 for 5 minutes to permeabilise the cell membranes. Slides were incubated with 30 μl OLINK® blocking buffer for 60 minutes at 37° C. in a humidity chamber. Primary antibodies were diluted in OLINK® Antibody diluent (mouse IgG anti E-cadherin 1:100, rabbit IgG anti β-catenin 1:200). Blocking buffer was removed and 15 μl of each antibody solution was added and incubated overnight at 4° C. Slides were washed, and incubated with 30 μl 20 nM secondary antibodies conjugated to oligonucleotides (nucleic acid probe and activator molecule) for 60 minutes at 37° C. in a humidity chamber. Following incubation, slides were washed and incubated with 30 μl RCA mix (Phi29 buffer, BSA, PolyA, dNTPs, UNG, HOECHST™, TEXAS RED® labelled detection oligonucleotide and Phi29 polymerase) for 100 minutes at 37° C. in a humidity chamber. Slides were washed at room temperature and allowed to try, before being contacted with SLOWFADE® mounting media and a coverslip applied and incubated for 15 minutes in the dark. All samples were analysed at the same magnification and exposure time (FIG. 18). Bright dots observed in the microscopy images are localised RCA products labelled with fluorescent detection oligonucleotides (Arrows in FIG. 18B). Negative control samples lacking each of the primary antibodies were included (FIG. 18C).

Example 6

Immobilised Nucleic Acid Probe

Figure 21:
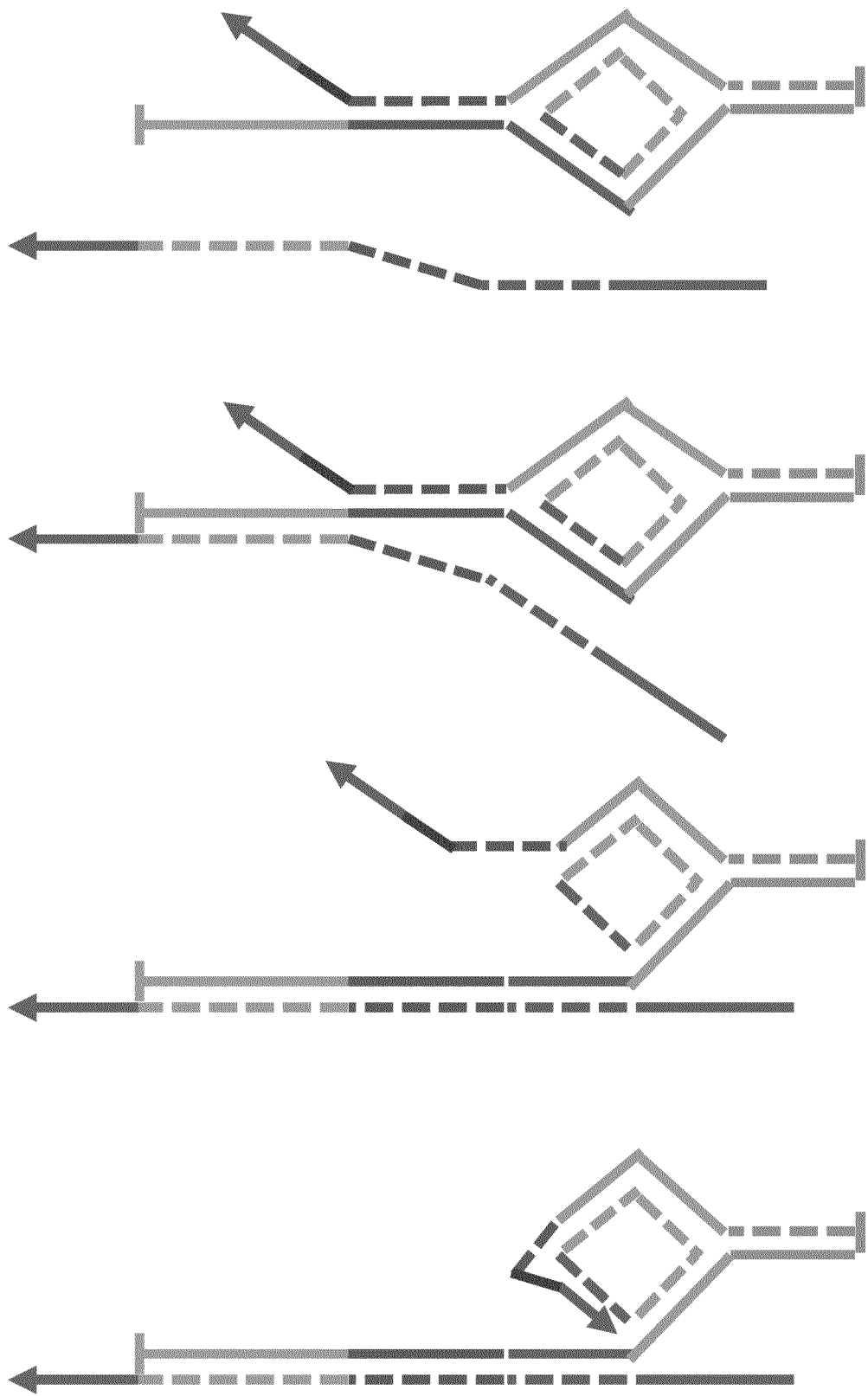
FIG. 21 shows a nucleic acid probe which comprises two second protector strands, with regions of complementarity for each other in their respective 5' and 3' end regions. One of the protector strands comprises a target binding site in its 5' end region; target binding to the target binding site leads to displacement of the other protector strand in the duplex, and from the first circular template strand. The 3' end of the other protector strand may comprise a sequence capable of binding to the exposed region and providing a primer for RCA initiation.
Figure 22A:
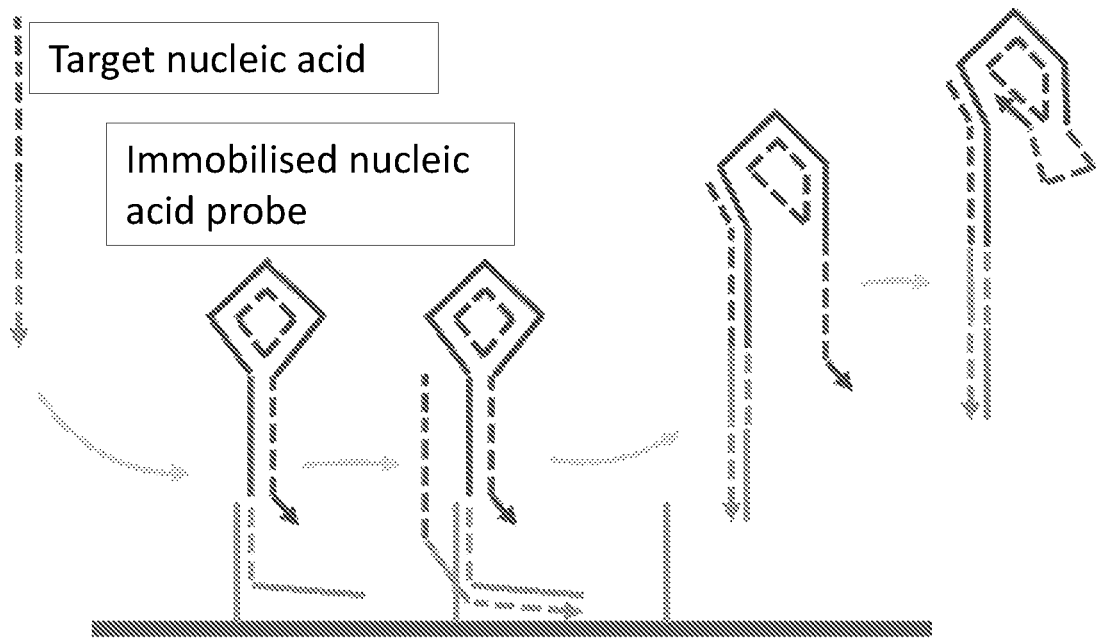
FIG. 22A: An experimental setup where the nucleic acid probe is immobilised to a solid support by a portion of the target binding site, and the target molecule both releases the nucleic acid probe from the surface and activates it. The supernatant may be collected following activation, and nucleic acid probes which are activated and released by the target nucleic acid molecule may be detected. Probes which are activated spontaneously (non-target specific) remain localised on the solid surface, and thus RCA products generated independently from target activation will not be detected.
Figure 22B:
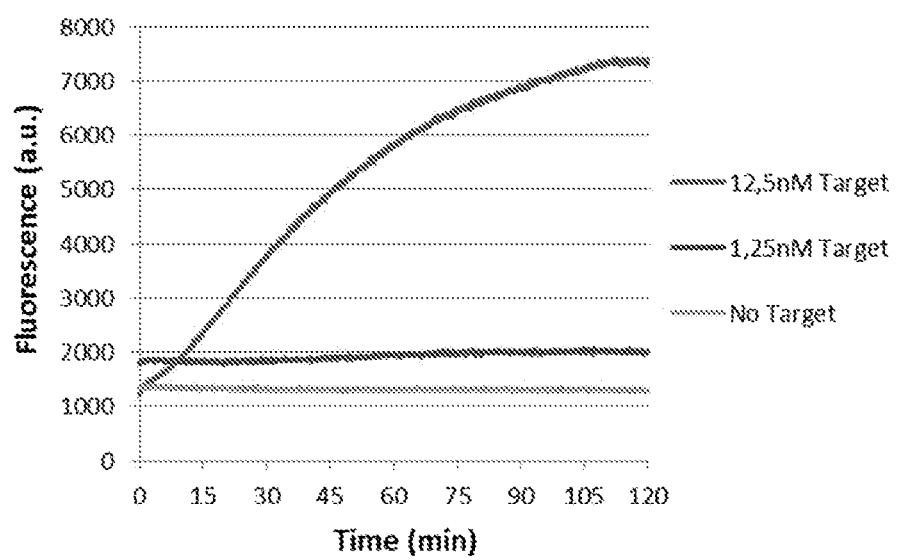
FIG. 22B: Different amounts of target molecules were incubated with probes immobilised on magnetic beads, and supernatant was collected following probe activation. A clear signal is seen for 12.5 nM target (top line), a small increase for 1.25 nM target (middle line) and no background was seen for the sample without target (bottom line).
Figure 23A:
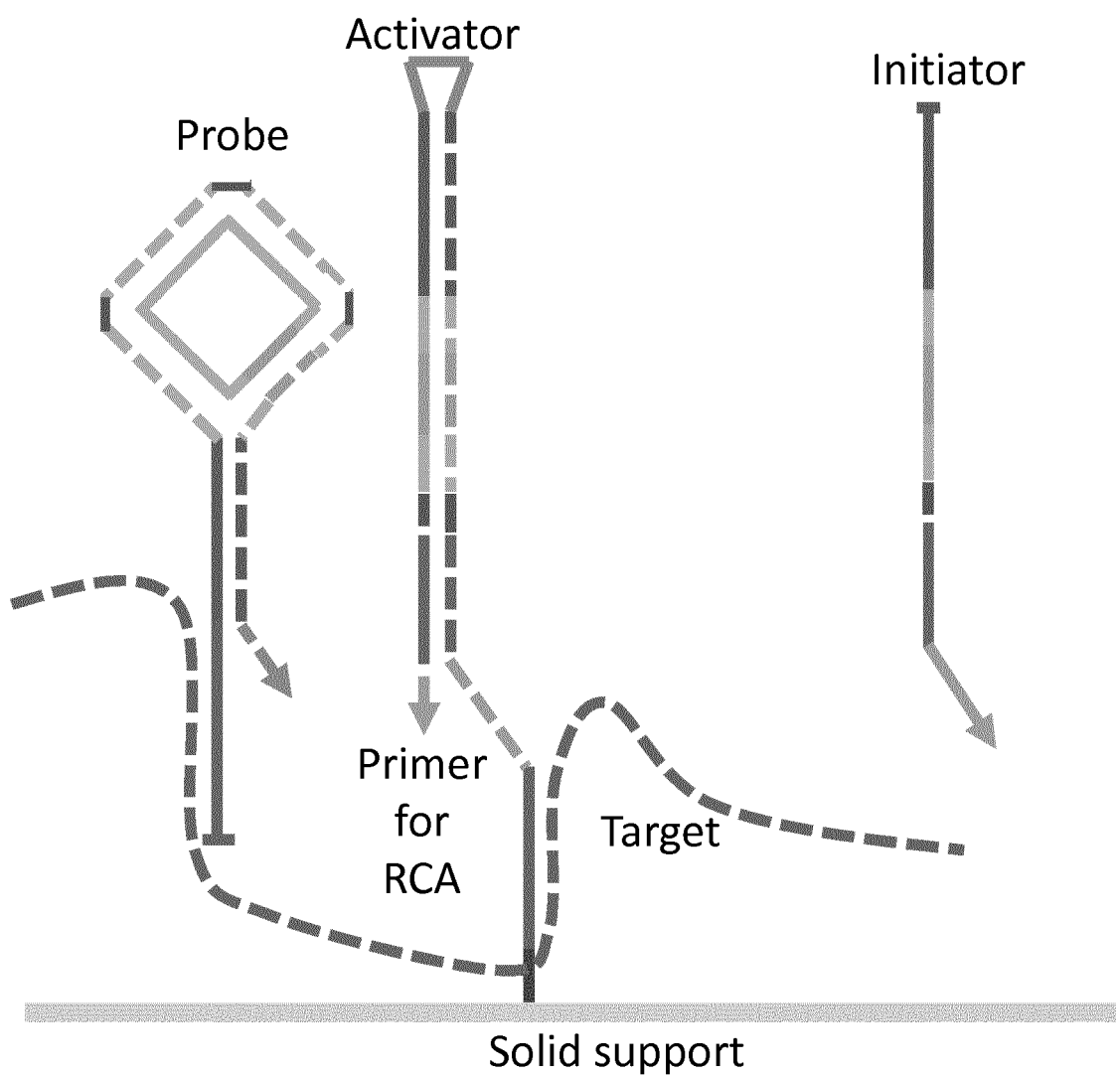
FIG. 23A: In this design, the activator molecule comprises a hairpin structure and a binding site for the target nucleic acid molecule in its 5' end, and is immobilised to a solid surface.
Figure 23B:
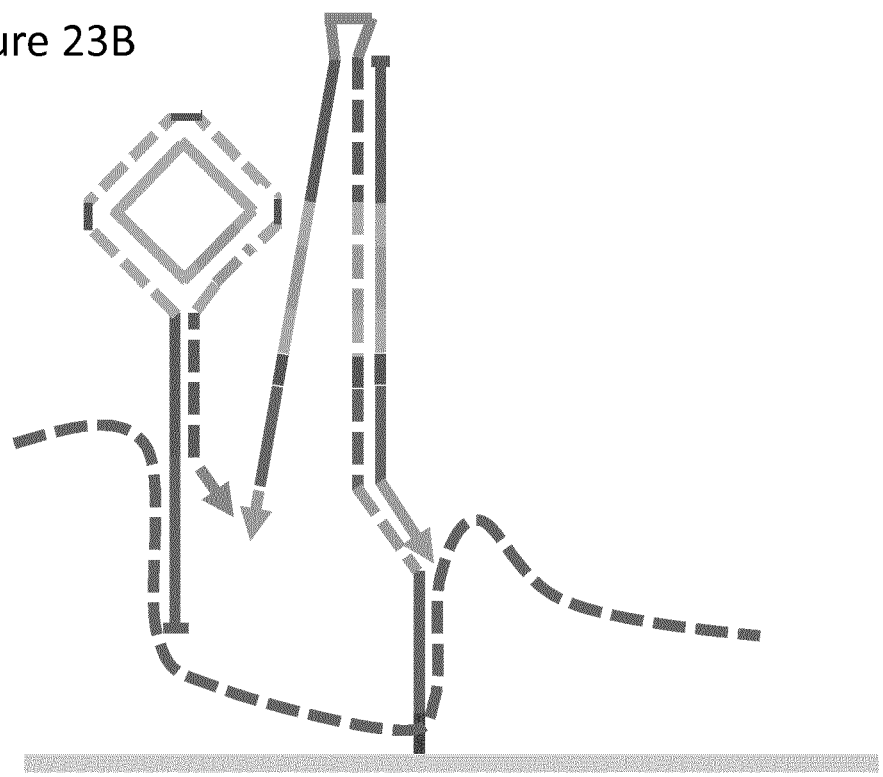
FIG. 23B: The target nucleic acid molecule binds to the activator and also binds to the nucleic acid probe via a single-stranded region at its 5' end. An initiator nucleic acid molecule is complementary to a region within the activator molecule, and is able to activate the activator molecule by strand displacement.
Figure 23C:
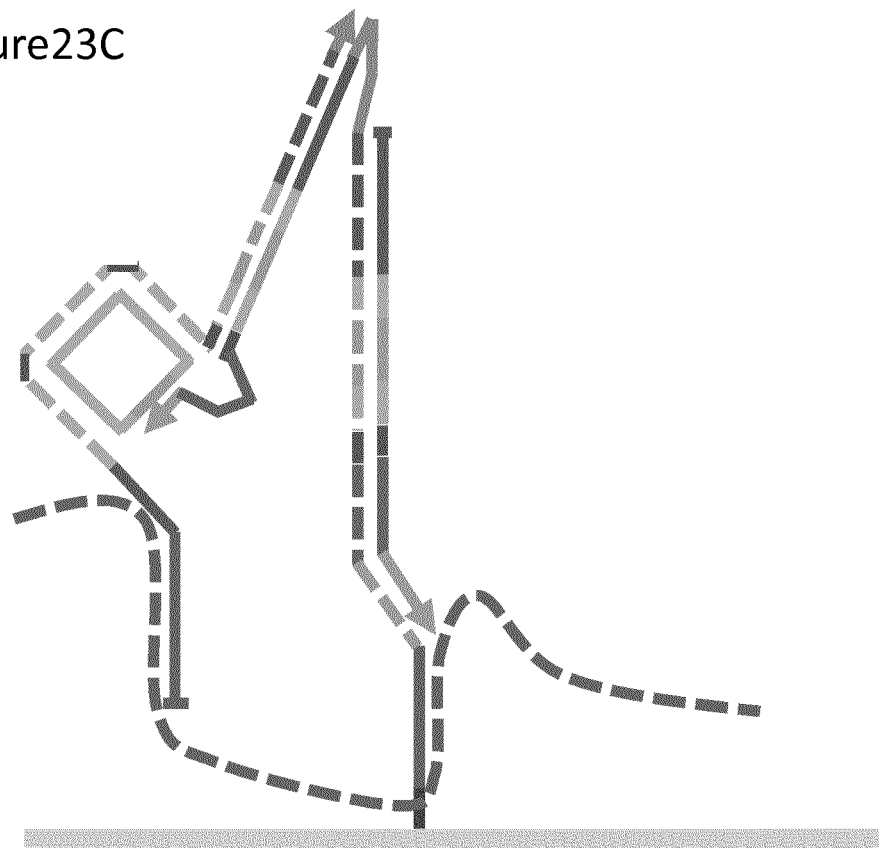
FIG. 23C: The activator molecule is then able to activate the nucleic acid probe and provide a primer to initiate RCA from its 3' end. In this setup, the second protector strand in the nucleic acid probe and the initiator molecule will preferably be protected from 3' exonuclease degradation and prevented from extension (extension blocked), and the activator molecule will preferably be protected from 3' exonuclease degradation, but not prevented from extension, such that it may act as a primer for RCA.
Figure 24:
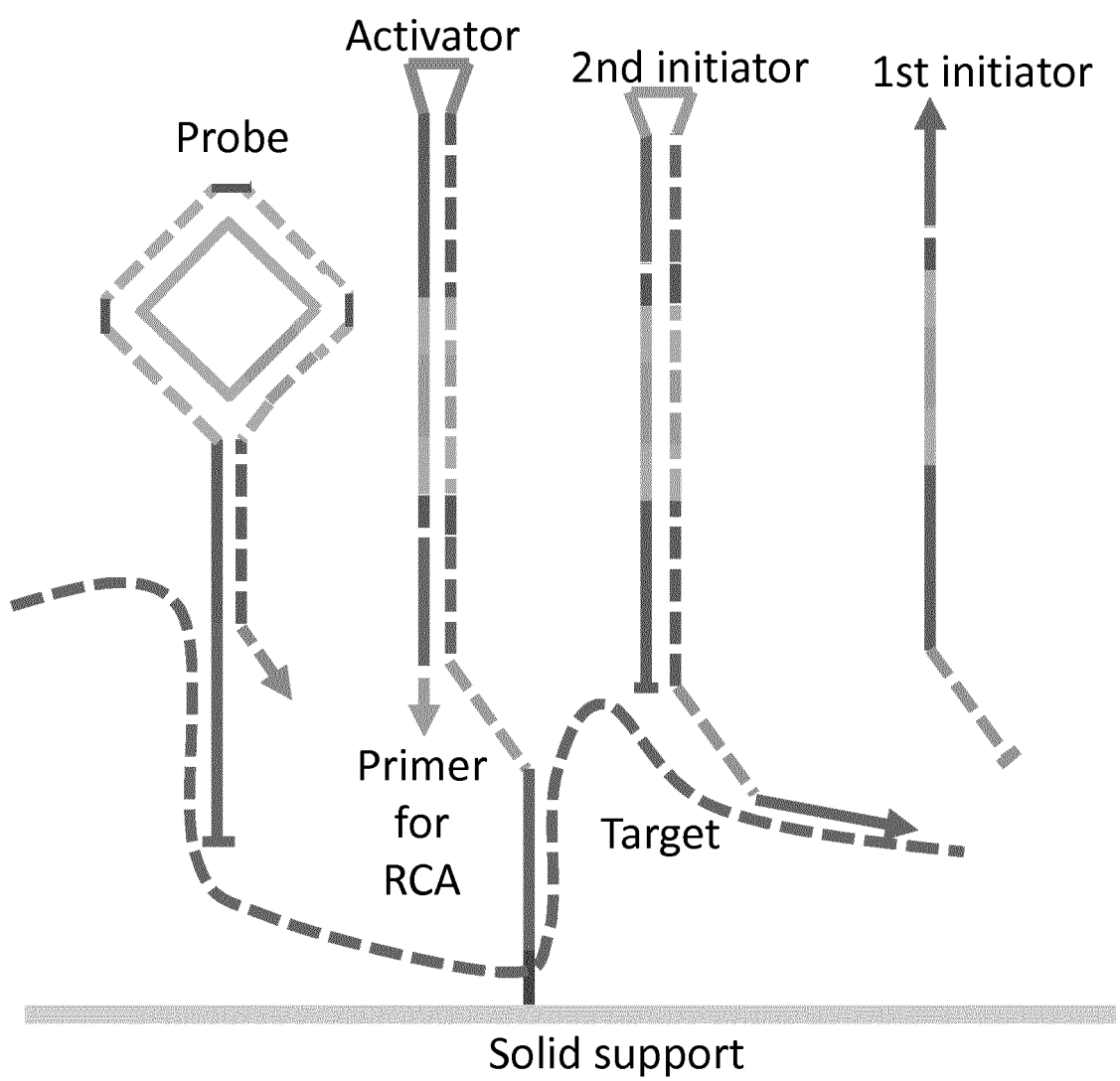
FIG. 24 shows a 'triple recognition' design for a set of nuclei acid molecules for the detection of a target nucleic acid molecule. In this design, the activator molecule comprises a hairpin structure and a binding site for the target nucleic acid molecule in its 5' end, and is immobilised to a solid surface. The target nucleic acid molecule binds to the activator and also binds to the nucleic acid probe via a single-stranded region at its 5' end. A first initiator nucleic acid molecule is complementary to a region within a second nucleic acid molecule, and is able to activate the second initiator nuclei acid molecule by strand displacement. The second initiator nucleic acid molecule is complementary to a region within the activator molecule, and is able to activate the activator molecule by strand displacement. The activator molecule is then able to activate the nucleic acid probe and provide a primer to initiate RCA from its 3' end. In this setup, the second protector strand in the nucleic acid probe, and first and second initiator molecules, will preferably be protected from 3' exonuclease degradation and prevented from extension (extension blocked), and the activator molecule will preferably be protected from 3' exonuclease degradation, but not prevented from extension, such that it may act as a primer for RCA.
Figure 25A:
FIG. 25 shows a nucleic acid probe and separate activator molecule which both comprise metastable secondary structures (FIG. 25A) which upon binding to the target nucleic acid molecule (FIG. 25B) are unfolded (FIG. 25C). Unfolding of the nucleic acid probe and separate activator molecule allows the probe binding site in the second activator molecule to bind to the activator binding site in the probe (FIG. 25D), thereby initiating an RCA reaction and activating the probe (FIG. 25E). The 3' end of the protector strand may comprise a sequence capable of binding to the exposed region, and providing a primer for RCA initiation.
Figure 25B:
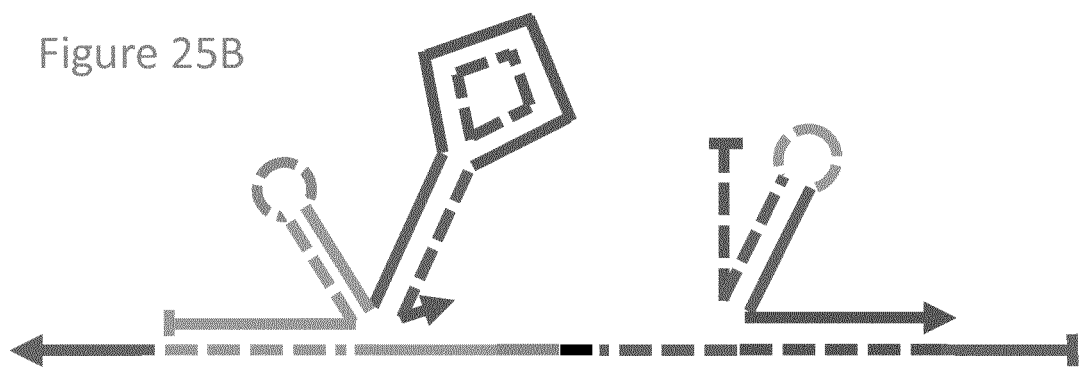
Figure 25C:
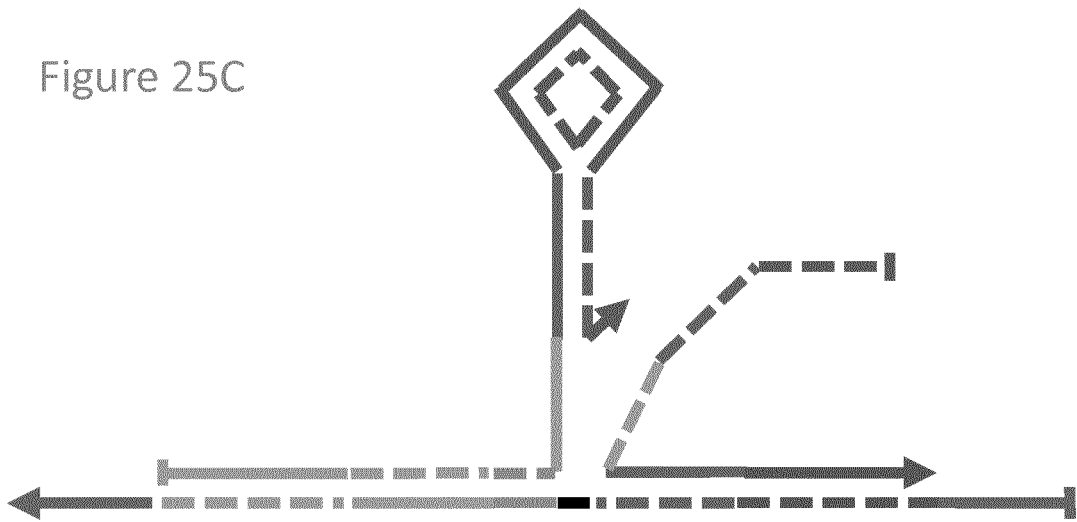
Figure 25D:
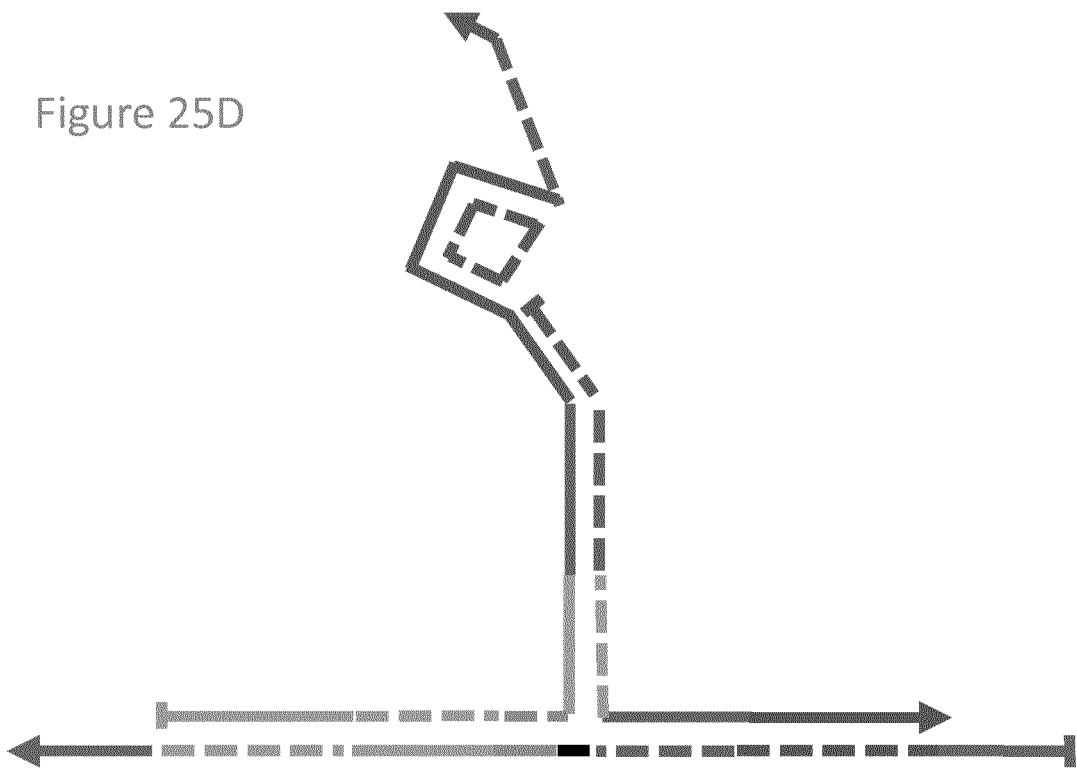
Figure 25E:
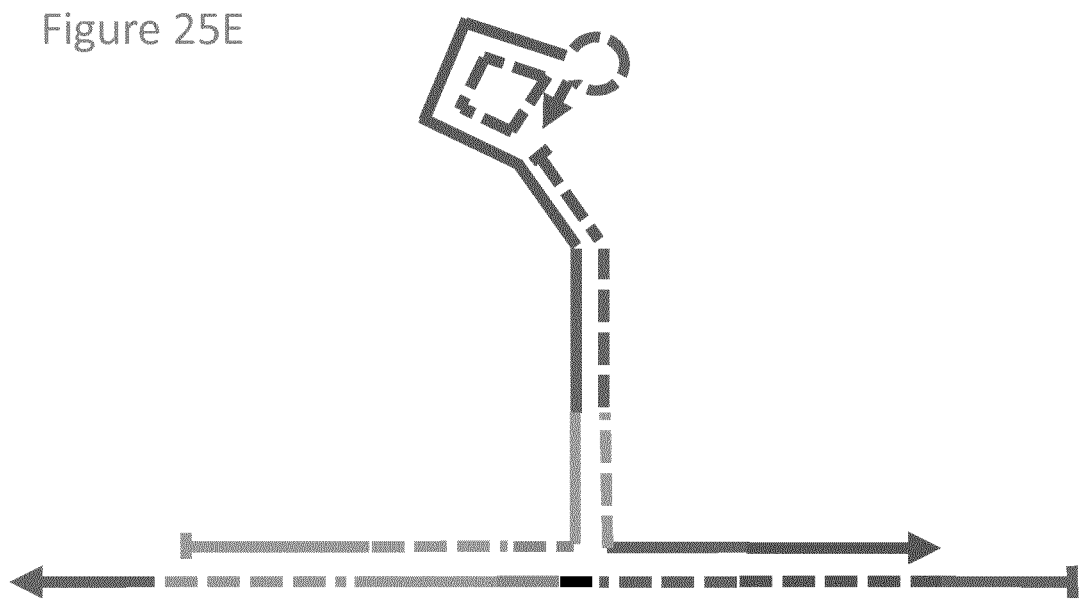
Figure 26A:
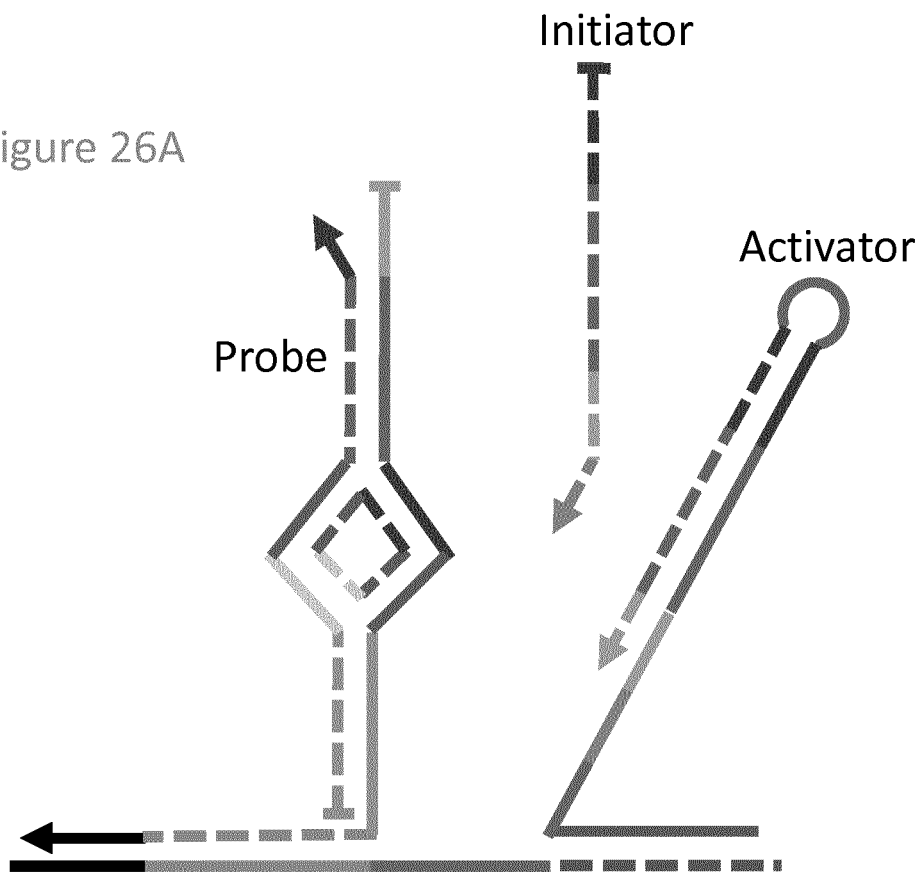
FIG. 26A: The probe and separate activator molecule bind to a target nucleic acid molecule.
Figure 26B:
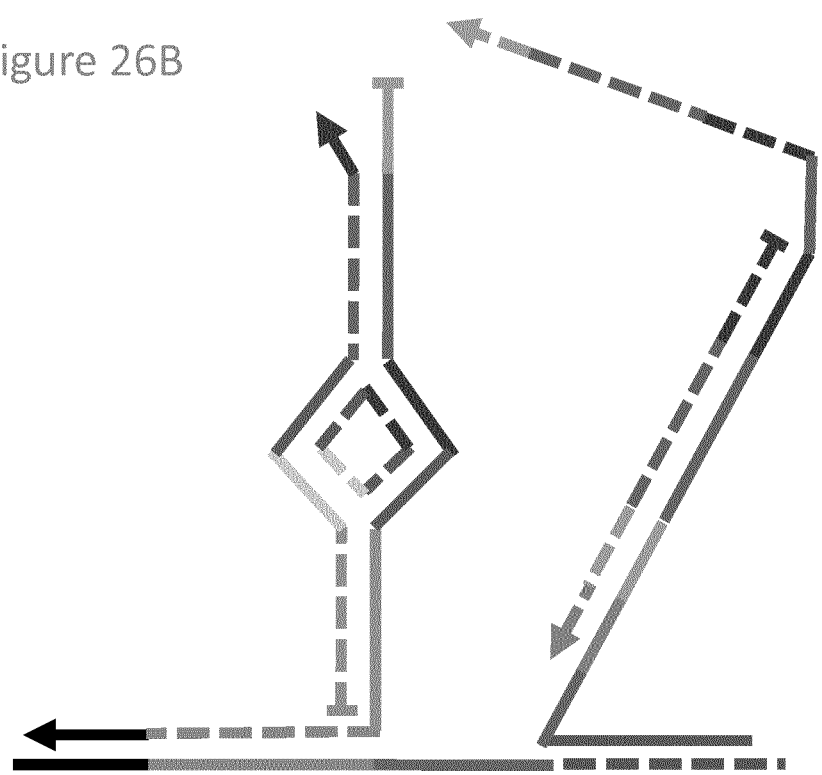
FIG. 26B: An initiator molecule binds to the separate activator molecule and releases the binding site for the nucleic acid probe.
Figure 26C:
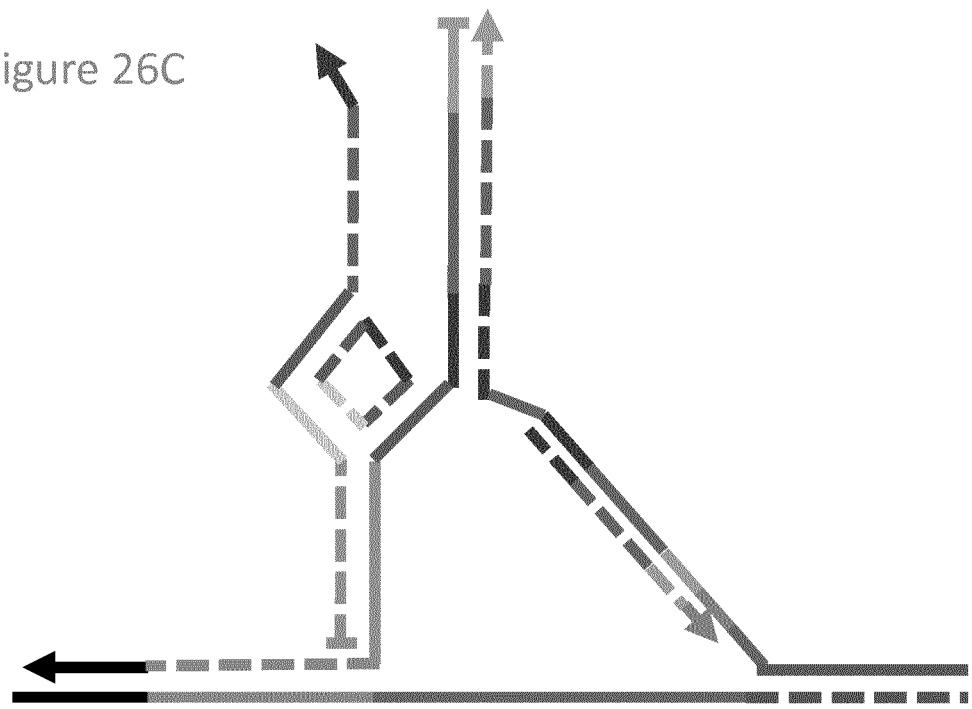
FIG. 26C: The target nucleic acid molecule binds to the activator. The activator molecule is then able to activate the nucleic acid probe.
Figure 26D:
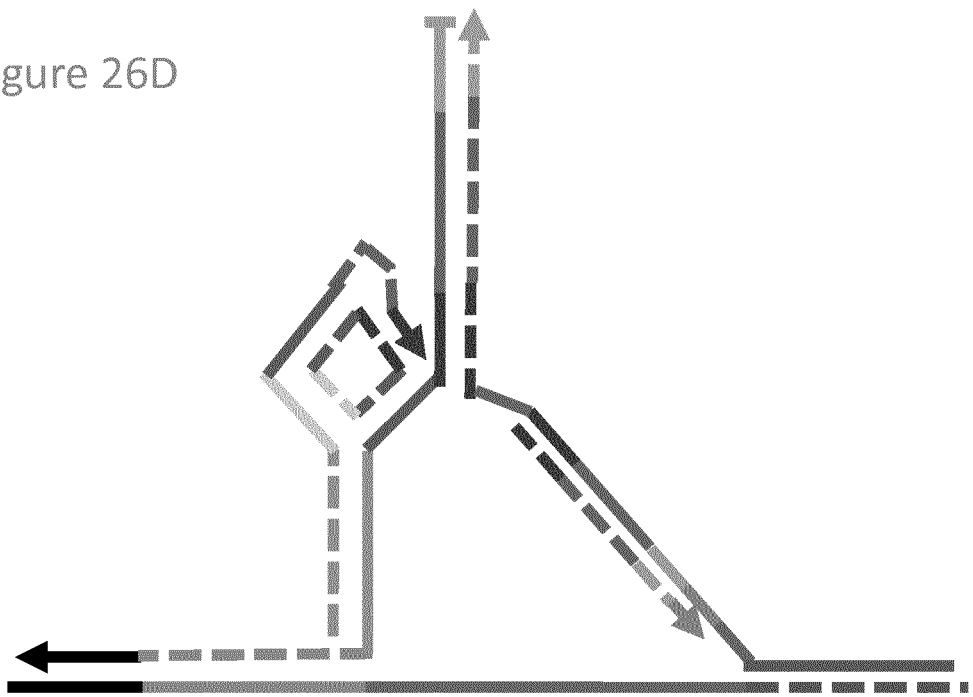
FIG. 26D: The 3' end of the other protector strand may comprise a sequence capable of binding to the exposed region and providing a primer for RCA initiation.

The nucleic acid probe was immobilised by hybridisation to a sequence complementary to a portion of the target binding site (FIG. 21) so that target binding releases the probe from the solid surface. The probe was immobilized by hybridisation to biotinylated oligos coupled to magnetic beads coated with streptavidin. Different amounts of target nucleic acid were incubated with the immobilised probes at 37° C. for 45 min. Following incubation the supernatants were transferred to tubes with RCA mix containing molecular beacons and the amplifications were monitored in a qPCR machine at 37° C. for 120 min (FIG. 21B).

A clear signal is seen for 12.5 nM target, a small increase for 1.25 nM target and no background was seen for the sample without target.

Figure 19:
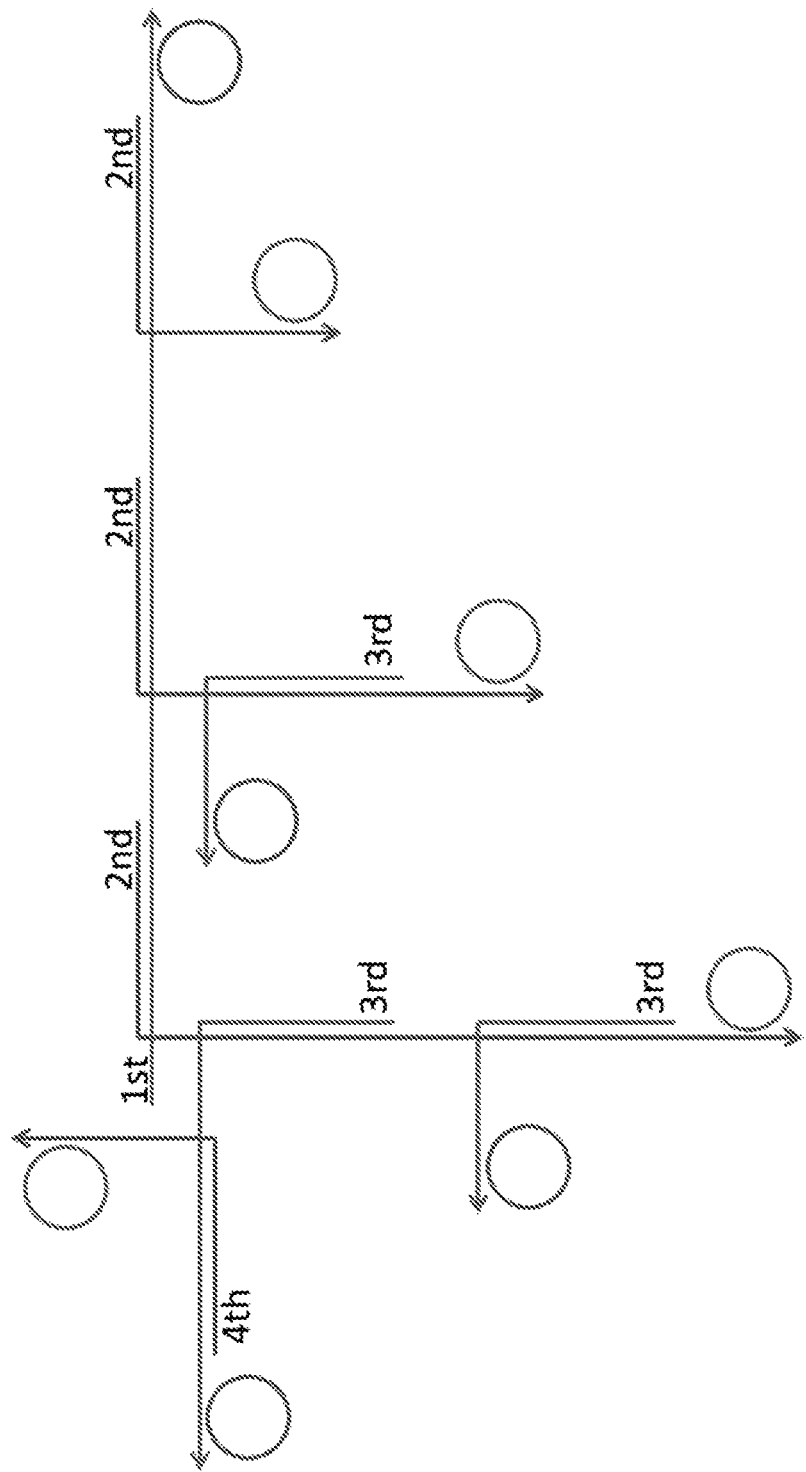
FIG. 19 shows an exponential amplification design involving two separate nucleic acid probes, in which the amplification product from performing RCA using the circular strand of a first probe as a template is able to activate the second probe, and vice-versa. Successive generations of activation and amplification leads to exponential and localised amplification.
Figure 20:
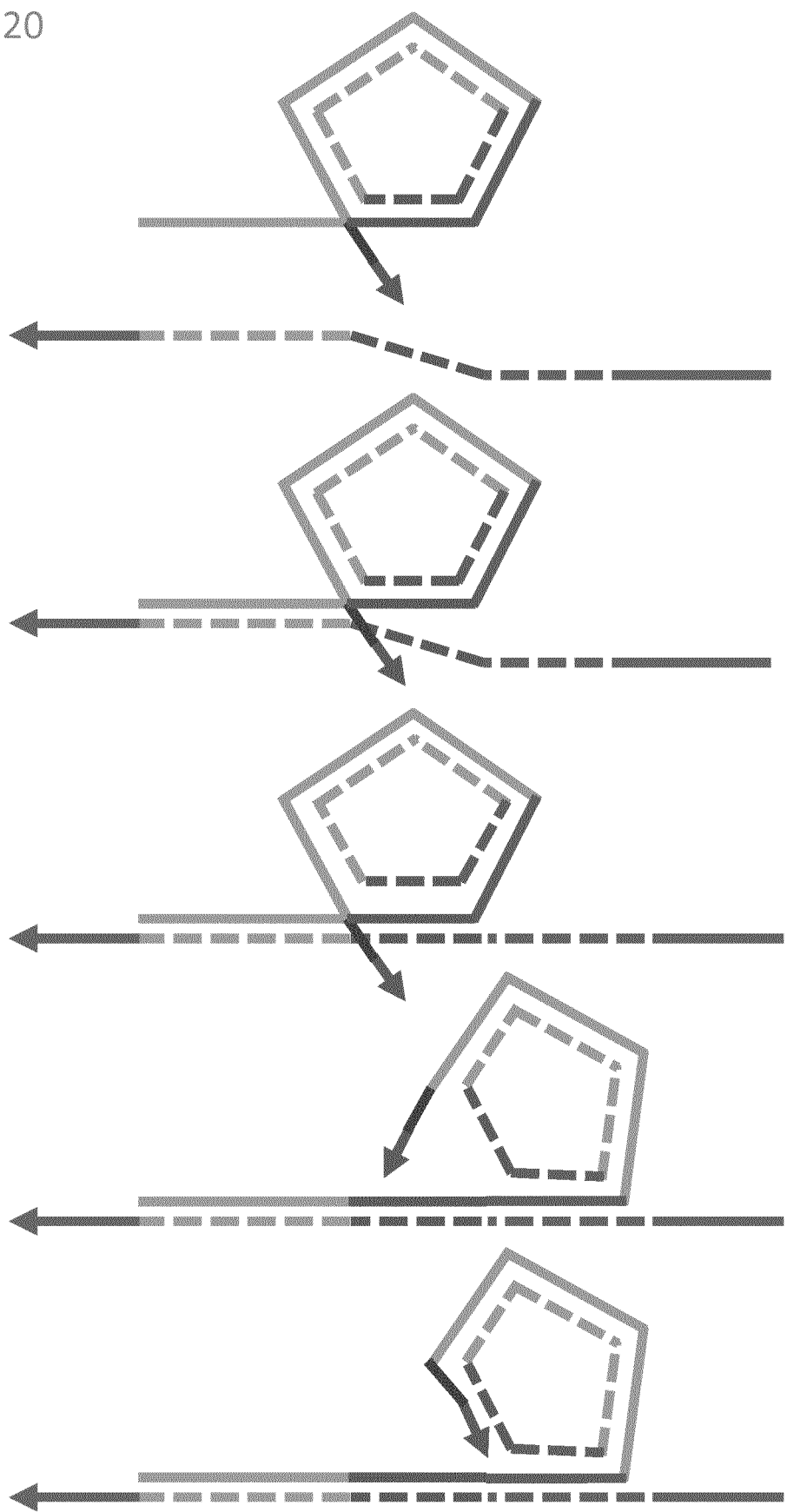
FIG. 20 shows a nucleic acid probe which does not comprise a stem-loop structure or a duplex region between the 5' and 3' end regions of the protector strand. Target binding to the target binding site leads to displacement of the protector strand from the circular template strand by strand displacement, exposing a region of the circular template strand. The 3' end of the protector strand may comprise a sequence capable of binding to the exposed region, and providing a primer for RCA initiation.

An assay in which an RCA mix is added directly to the immobilised nucleic acid probe in the presence of an immobilised second generation nucleic acid probe recognising the RCA product from the first RCA reaction is anticipated. Furthermore, rapid amplification using a pair of immobilised cross-reactive probes, as shown in FIG. 19, could also be used in an assay format such as this.

| Sequence name | SEQ ID NO | Sequence |
|---|---|---|
| Protector strand 1 | 1 | AACAGCTAGGCCAGTACCAACACACACACCAAACC ACAAATTAACACAACACCAGAAGAGAAAGAGACGA CAATGGTTACAGAACGAGAAAGAAGAAAGAAGAGA AGCGCCAGGATAGTTGTGTTAATTTGCCTAGCTGT T |
| Protector strand 2 | 2 | TTGTGTTGAGTTGAGTAGAGAGGAGAGAAGAGAAG AAAGTAAGAAGCGCCTGGATAAGAAGAGATGCAAA AGAGACGACAATGGTTACAGAACGAGAAATCAGAA AGAACTTTCTTCTATTCTCTCCTGCGCCA |
| Template strand | 3 | CATTGTCGCTCTTTTGCATCTCTTTATCCTGGCGC TTCTCTCTTTCTGATTTCTCGTCTGTAAC |
| Target 1 | 4 | TGGGTGTTGTGTTAATTTGTGGTTTGGTGTGTGTG TTGGTACTGGCCTAGCTGTTTGGTT |
| Target 2 | 5 | CTTATCCAGGCGCTTCTTACTTTCTTCTCTTCTCT CCTCTCTACTCAACTCAACACAA |

The invention claimed is:

1. A nucleic acid probe for detection of a target nucleic acid molecule by a rolling circle amplification (RCA) reaction, wherein said nucleic acid probe is able to undergo a RCA reaction in the presence of the target nucleic acid molecule, said nucleic acid probe comprising:

(i) a first circular template strand which is capable of acting as a template for RCA; and (ii) at least a second protector strand which protects the first circular template strand from RCA in the absence of the target nucleic acid molecule, wherein at least one of the second and/or any further protector strands comprises a target binding site;

wherein the second and any further protector strand(s) comprise a region of complementarity to the first circular template strand and are hybridised thereto to form a double-stranded circular structure containing the first circular template strand inside the protector strand(s), thereby inhibiting RCA of the first circular template strand, and wherein a second and/or further protector strand further comprises at least a first single-stranded region which comprises at least an accessible part of the target binding site which allows the nucleic acid probe to bind to a complementary binding site in the target nucleic acid molecule, such that upon binding of the nucleic acid probe to the target nucleic acid molecule, the nucleic acid probe is able to undergo a strand displacement reaction which allows RCA of the first circular template strand.

2. The nucleic acid probe of claim 1, wherein
said nucleic acid probe comprises a single second protector strand, and the single second protector strand comprises the target binding site, wherein the second protector strand forms a loop which is complementary to the first circular template strand and is hybridised thereto to form a double-stranded circular structure containing the first circular template strand inside the loop, thereby inhibiting RCA of the first circular template strand, and wherein the second protector strand further comprises at least a first single-stranded region which comprises at least an accessible part of the target binding site which allows the nucleic acid probe to bind to a complementary binding site in the target nucleic acid molecule, such that upon binding of the nucleic acid probe to the target nucleic acid molecule, the nucleic acid probe is able to undergo a strand displacement reaction which allows RCA of the first circular template strand.

3. The nucleic acid probe of claim 1, wherein said nucleic acid probe is activatable in the presence of the target nucleic acid molecule to undergo a RCA reaction, the activator for said RCA reaction being either the target nucleic acid molecule or a separate activator molecule binding to the target nucleic acid, and wherein:
  (a) optionally at least one second or further protector strand comprises a binding site for the separate activator molecule; and
  (b) optionally a second and/or further protector strand comprises a second single-stranded region which comprises at least an accessible part of the binding site for the separate activator molecule,
such that upon binding of the nucleic acid probe to the target nucleic acid molecule, the nucleic acid probe is able to undergo a strand displacement reaction mediated by the target nucleic acid molecule or by the separate activator molecule when bound to the target molecule, to allow RCA of the first circular template strand.

4. The nucleic acid probe of claim 3, wherein
  (a) the nucleic acid probe comprises a single second protector strand which forms a loop which is complementary to the first circular template strand and is hybridised thereto to form a double-stranded circular structure containing the first circular template strand inside the loop, thereby inhibiting RCA of the first circular template strand, and wherein the second protector strand further comprises at least a first single-stranded region which comprises at least an accessible part of the target binding site which allows the nucleic acid probe to bind to a complementary binding site in the target nucleic acid molecule, and optionally a second single-stranded region which comprises at least an accessible part of the binding site for the separate activator molecule, such that upon binding of the nucleic acid probe to the target nucleic acid molecule, the nucleic acid probe is able to undergo a strand displacement reaction mediated by the target nucleic acid molecule or by the separate activator molecule when bound to the target molecule to allow RCA of the first circular template strand; or
  (b) the nucleic acid probe comprises two or more protector strands which form an envelope which is complementary to the first circular template strand and is hybridised thereto to form a double-stranded circular structure containing the first circular template strand inside the envelope, thereby inhibiting RCA of the first circular template strand, and wherein a protector strand further comprises at least a first single-stranded region which comprises at least an accessible part of the target binding site which allows the nucleic acid probe to bind to a complementary binding site in the target nucleic acid molecule, and optionally a protector strand, which may be the same or different, further comprises a second single-stranded region which comprises at least an accessible part of the binding site for the separate activator molecule, such that upon binding of the nucleic acid probe to the target nucleic acid molecule, the nucleic acid probe is able to undergo a strand displacement reaction mediated by the target nucleic acid molecule or by the separate activator molecule when bound to the target molecule, to allow RCA of the first circular template strand.

5. The nucleic acid probe of claim 3, wherein the activator for the RCA reaction is the target nucleic acid molecule.

6. The nucleic acid probe of claim 3, wherein the activator for the RCA reaction is a separate activator molecule and the nucleic acid probe comprises a second single-stranded region which comprises at least an accessible part of the activator binding site, and wherein the first and second single-stranded regions are separated spatially.

7. The nucleic acid probe of claim 6, wherein:
  (a) the first and second single-stranded regions are situated in the same protector strand; or
  (b) the first and second single-stranded regions are situated at different ends of a second protector strand; or
  (c) the nucleic acid probe comprises two or more protector strands, and the first and second single-stranded regions are situated in different protector strands; or
  (d) the second single-stranded region is situated at the 3' end of a second protector strand.

8. The nucleic acid probe of claim 3, wherein the target binding site, or if present the binding site for the separate activator molecule, lies at least partially within a loop region of the second protector strand and is at least partially hybridised to the first circular template strand.

9. The nucleic acid probe of claim 1, wherein the strand displacement reaction displaces part of a second protector strand from the double-stranded circular structure, thereby exposing a part of the first circular template strand to allow binding of a primer for the RCA reaction and wherein the 3' end region of the second protector strand comprises the RCA primer.

10. The nucleic acid probe of claim 1, wherein
   (a) the first single-stranded region is situated at an end of a second protector strand; and/or
   (b) the first single-stranded region is situated at the 5' end of a second protector strand; or
   (c) the first single-stranded region is situated at an intermediate position within the second protector strand.

11. The nucleic acid probe of claim 1, wherein a second protector strand comprises a primer sequence in the 3' end region thereof or in an intermediate region thereof, which is capable of acting as or providing a primer for RCA of the first circular template strand when the nucleic acid probe has been activated.

12. The nucleic acid probe of claim 1, wherein:
   (a) the nucleic acid probe comprises a single second protector strand and the 5' and 3' end regions of the second protector strand comprise mutually complementary regions which are hybridised to each other to form a stem-loop structure comprising a loop which is complementary to the first circular template strand and is hybridised thereto to form a double-stranded circular structure containing the first circular template strand inside the loop, and a partially double-stranded stem region comprising a duplex between the mutually complementary regions in the 5' and 3' end regions, and at least the first single-stranded region; or
   (b) the nucleic acid probe comprises two or more protector strands, which protector strands comprise 5' and 3' end regions which comprise complementary regions to end regions of another protector strand and which are hybridised thereto to form a double-stranded circle structure comprising portions of the second protector strands complementary to the first circular template strand and partially double-stranded stem regions comprising regions of duplex between the mutually complementary regions in the 5' and 3' end regions, and wherein one of the regions of duplex comprises at least the first single-stranded region.

13. The nucleic acid probe of claim 12, wherein:
   (a) the first single-stranded region is situated in a bulge in a strand of a said duplex; or
   (b) the first single-stranded region is situated in a bulge in the 5' end region of the single protector strand or in a bulge in the 5' end region of one of the two or more protector strands; or
   (c) the first single-stranded region lies at an end of a strand of a duplex; or
   (d) the first single-stranded region lies at the 5' end of the second protector strand 5' to the duplex.

14. The nucleic acid probe of claim 13, wherein in part (c) or (d), a second single-stranded region lies at the end of the other strand of the duplex.

15. The nucleic acid probe of claim 13, wherein in part (a) or (b) a first accessible domain of the target binding site, or if present, a binding site for a separate activator molecule is situated in the bulge and further target binding domains of the target binding site or if present, further binding domains for the separate activator molecule, are present in the stem, such that binding of the target nucleic acid molecule or separate activator molecule causes a strand displacement reaction which opens at least the stem of the stem-loop structure and releases the 3' or 5' end of the second protector strand.

16. The nucleic acid probe of 15, wherein binding of the target nucleic acid molecule or separate activator molecule causes a strand displacement reaction which opens at least the stem of the stem-loop structure and releases the 3' end of the second protector strand, and wherein the released 3' end of the second protector strand is (i) cleavable to provide a primer for RCA of the first circular template strand, or (ii) is able to bind to the first circular template strand following the strand displacement reaction, to prime RCA of the first circular template strand.

17. The nucleic acid probe of claim 1, wherein the first single-stranded region is situated at the 3' end of a second protector strand.

18. The nucleic acid probe of claim 1, wherein the nucleic acid probe comprises the double-stranded circular structure, a single-stranded 5' end region of the second protector strand comprising an accessible part of the target binding site, and a single-stranded 3' end region of the second protector strand comprising a primer for the RCA reaction.

19. The nucleic acid probe of claim 1, wherein the nucleic acid probe comprises:
   (i) a first circular template strand which is capable of acting as a template for RCA; and
   (ii) a second protector strand which protects the first circular template strand from RCA in the absence of the target nucleic acid molecule, and which comprises (a) in the 5' end region thereof the target binding site and a binding site for a separate activator molecule, said target binding site and said separate activator binding site each comprising first, second and third domains, the first domain of the target binding site being accessible for binding by the target nucleic acid molecule, thereby allowing the nucleic acid probe to bind to a complementary site in the target nucleic acid molecule and (b) in the 3' end region thereof a primer domain capable of hybridising to the first circular template strand to prime RCA thereof;
   wherein the 5' and 3' end regions of the second protector strand comprise mutually complementary regions which are hybridised to each other to form a first stem-loop structure comprising a first loop which is complementary to the first circular template strand and is hybridised thereto to form a double-stranded circular structure containing the first circular template strand inside the first loop, and a partially double-stranded stem region comprising
   (i) a first duplex between the mutually complementary regions,
   (ii) a 5' end region comprising a first single-stranded region which contains the accessible first domain of the target binding site at the end of the 5' strand of the first duplex and a second stem-loop structure comprising a second loop and a second duplex, and
   (iii) a single-stranded 3' end region comprising the primer domain at the end of the 3' strand of the first duplex; and
   wherein the second and third domains of the target binding site are contained in the second duplex and second loop, respectively, and the first, second and third domains of the separate activator binding site are contained in the second duplex, first duplex and first loop respectively, the second domain of the target binding site being complementary and hybridised to the first domain of the activator binding site within the second duplex, and the third domain of the activator binding site being hybridised to the first circular template strand;
   such that upon binding of the first accessible domain of the target binding site to its complementary site in the target nucleic acid molecule, strand displacement by the target nucleic acid molecule causes the second duplex to open, to allow the respective complementary sites of the target nucleic acid molecule to bind to the second and third domains of the target binding site, and thereby rendering accessible the first domain of the separate activator binding site, whereupon binding of the separate activator molecule to the first domain of its binding site displaces the sequences hybridised to the second and third domains of the separate activator binding site and causes the first duplex to open and the second protector strand at least partially to dissociate from the first circular template strand, allowing the single-stranded 3' end of the second protector strand to bind to the first circular template strand to provide a primer for RCA of the first circular template strand.

20. The nucleic acid probe of claim 1, wherein:
(a) the first circular template strand is less than 100 nucleotides in length; and/or
(b) the first circular template strand is at least 20 nucleotides in length; and/or
(c) the first circular template strand and the second and/or further protector strand(s) comprise one or more mismatches within a loop structure-; and/or
(d) the second and/or further protector strand(s) contains one or more base insertions relative to the first circular template strand, or wherein the first circular template strand contains one or more base insertions relative to the second and/or further protector strand(s).

21. The nucleic acid probe of claim 1, wherein the nucleic acid probe comprises two or more protector strands and at least one of the protector strands comprises a target binding site, wherein the two or more protector strands form an envelope which is complementary to the first circular template strand and is hybridised thereto to form a double-stranded circular structure containing the first circular template strand inside the envelope, thereby inhibiting RCA of the first circular template strand, and wherein a protector strand further comprises at least a first single-stranded region which comprises at least an accessible part of the target binding site which allows the nucleic acid probe to bind to a complementary binding site in the target nucleic acid molecule, such that upon binding of the nucleic acid probe to the target nucleic acid molecule, the nucleic acid probe is able to undergo a strand displacement reaction which allows RCA of the first circular template strand.

22. A method for detecting a target nucleic acid molecule by an RCA reaction, said method comprising:
(a) contacting the target nucleic acid molecule with a nucleic acid probe as defined in claim 1;
(b) if said nucleic acid probe is activated by a separate activator molecule, simultaneously or separately before or after step (a), contacting the target nucleic acid molecule with a separate activator molecule, said activator molecule comprising a binding site for the target nucleic acid molecule and a binding site complementary and capable of binding to a binding site for the separate activator molecule in the nucleic acid probe;
(c) allowing the target nucleic acid molecule to bind to the separate activator molecule, if present;
(d) allowing the target nucleic acid molecule and, if present, separately or simultaneously the separate activator molecule to bind to the nucleic acid probe, wherein binding of the target nucleic acid molecule, or if present the activator molecule, to the nucleic acid probe causes a strand displacement reaction which activates the nucleic acid probe to allow RCA of the first circular template strand of the nucleic acid probe;
(e) performing an RCA reaction using the first circular template strand as the RCA template; and
(f) detecting the RCA product from step (e), thereby detecting a sequence of the target nucleic acid molecule.

23. A kit comprising:
a) a nucleic acid probe as defined in claim 1, and one or more further components selected from:
b) a polymerase enzyme for rolling circle amplification;
c) a primer for RCA;
d) a separate activator molecule;
e) one or more reagents for performing an RCA reaction;
f) means for detecting an RCA product; and
g) an initiator oligonucleotide, or other means for introducing permissive conditions to allow the target nucleic acid molecule or a separate activator molecule to bind to the nucleic acid probe.

24. A method for detecting a target analyte in a sample, said method comprising:
(i) contacting the target analyte with at least a first proximity probe and a second proximity probe, wherein said proximity probes each comprise an analyte-binding domain and a nucleic acid domain and can simultaneously bind to the target analyte, wherein the nucleic acid domain of the first proximity probe is a nucleic acid probe as defined in claim 1, and wherein the nucleic acid domain of the second proximity probe is a target nucleic acid molecule comprising a binding site complementary and capable of binding to the target binding site in the nucleic acid probe;
(ii) allowing the nucleic acid domains of the proximity probes to interact with each other upon binding of the proximity probes to said target analyte, wherein said interaction causes a strand displacement reaction which activates the nucleic acid probe to allow RCA of the first circular template strand of the nucleic acid probe;
(iii) performing an RCA reaction using the first circular template strand as the RCA template; and
(iv) detecting the RCA product from step (c), thereby detecting the target analyte in the sample.

25. A method for detecting a target analyte in a sample, said method comprising:
(i) contacting the target analyte with
(a) a nucleic acid probe as defined in claim 1, and a separate activator molecule for the nucleic acid probe; and
(b) at least a first proximity probe and a second proximity probe, wherein said proximity probes each comprise an analyte-binding domain and a nucleic acid domain and can simultaneously bind to the target analyte, wherein the nucleic acid domain of the first proximity probe is a target nucleic acid molecule comprising a binding site complementary and capable of binding to the target binding site in the nucleic acid probe, and wherein the nucleic acid domain of the second proximity probe is an intermediary molecule comprising a binding site complementary and capable of binding to a binding site in the separate activator molecule;
wherein said nucleic acid probe and separate activator molecule contact the target analyte simultaneously with or after the at least first proximity probe and second proximity probe;
(ii) allowing the nucleic acid probe and separate activator molecule to bind to the nucleic acid domains of the proximity probes, wherein the nucleic acid probe and separate activator molecule interact with each other upon binding of the proximity probes to said analyte, wherein said interaction causes a strand displacement reaction which activates the nucleic acid probe to allow RCA of the first circular template strand of the nucleic acid probe;

(iii) performing an RCA reaction using the first circular template strand as the RCA template; and (iv) detecting the RCA product from step (iii), thereby detecting the target analyte in the sample.

26. A method for detecting a target analyte in a sample, said method comprising:

(i) contacting the target analyte with
 (a) a nucleic acid probe as defined in claim 1; and
 (b) at least a first proximity probe and a second proximity probe, wherein said proximity probes each comprise an analyte-binding domain and a nucleic acid domain and can simultaneously bind to the target analyte, wherein the nucleic acid domain of the first proximity probe is a target nucleic acid molecule comprising a binding site complementary and capable of binding to the target binding site in the nucleic acid probe, and wherein the nucleic acid domain of the second proximity probe is a separate activator molecule, said activator molecule comprising a binding site complementary and capable of binding to a binding site for the separate activator molecule in the nucleic acid probe;

wherein said nucleic acid probe contacts the target analyte simultaneously with or after the at least first proximity probe and second proximity probe;

(ii) allowing the nucleic acid probe to bind to the nucleic acid domains of the proximity probes, wherein the nucleic acid probe and separate activator molecule interact with each other upon binding of the proximity probes to said target analyte, wherein said interaction causes a strand displacement reaction which activates the nucleic acid probe to allow RCA of the first circular template strand of the nucleic acid probe;

(iii) performing an RCA reaction using the first circular template strand as the RCA template; and (iv) detecting the RCA product from step (iii), thereby detecting the target analyte in the sample.

\* \* \* \* \*